(12) United States Patent
Hathaway

(10) Patent No.: US 9,724,073 B2
(45) Date of Patent: Aug. 8, 2017

(54) BIOPSY DEVICE

(76) Inventor: Jeff M. Hathaway, Lebanon, WI (US)

( * ) Notice: Subject to any disclaimer, the term of this patent is extended or adjusted under 35 U.S.C. 154(b) by 35 days.

(21) Appl. No.: 14/394,702

(22) PCT Filed: Apr. 16, 2012

(86) PCT No.: PCT/US2012/033851
§ 371 (c)(1),
(2), (4) Date: Oct. 15, 2014

(87) PCT Pub. No.: WO2013/158072
PCT Pub. Date: Oct. 24, 2013

(65) Prior Publication Data
US 2015/0105690 A1    Apr. 16, 2015

(51) Int. Cl.
| A61B 10/02 | (2006.01) |
| A61B 19/00 | (2006.01) |
| A61B 10/04 | (2006.01) |
| A61B 90/00 | (2016.01) |

(52) U.S. Cl.
CPC ...... *A61B 10/0275* (2013.01); *A61B 10/0283* (2013.01); *A61B 10/04* (2013.01); *A61B 90/06* (2016.02); *A61B 2010/0208* (2013.01); *A61B 2090/062* (2016.02)

(58) Field of Classification Search
CPC ............... A61B 2010/0208; A61B 10/0275
See application file for complete search history.

(56) References Cited

U.S. PATENT DOCUMENTS

| 4,968,303 A | 11/1990 | Clarke et al. |
| 5,449,001 A | 9/1995 | Terwilliger |
| 5,797,907 A | 8/1998 | Clement |
| 6,626,849 B2 | 9/2003 | Huitema et al. |
| 6,656,133 B2 | 12/2003 | Voegele et al. |
| 6,712,773 B1 | 3/2004 | Viola |
| 6,712,774 B2 | 3/2004 | Voegele et al. |
| 6,730,044 B2 | 5/2004 | Stephens et al. |
| 6,758,848 B2 | 7/2004 | Burbank et al. |
| 6,792,305 B2 | 9/2004 | Rastorgoueff et al. |

(Continued)

FOREIGN PATENT DOCUMENTS

| CA | 2870694 | 10/2013 |
| EP | 2260767 A1 | 12/2010 |

(Continued)

OTHER PUBLICATIONS

The Right Biopsy Solution for Every Patient, HOLOGIC, catalog, Mar. 2011 (United States).

(Continued)

*Primary Examiner* — Michael C Stout
*Assistant Examiner* — Nicholas E Kolderman
(74) *Attorney, Agent, or Firm* — Jansson Munger McKinley & Kirby Ltd.

(57) ABSTRACT

Biopsy devices (10, 10') for acquiring tissue samples (59). In embodiments, exemplary biopsy devices include a cutter (127), a cannula (13) including a tissue-receiving cavity (42), a vacuum generating mechanism (17) and a tissue cutting mechanism (15). Vacuum generating mechanism draws tissue (47) into tissue-receiving cavity and tissue cutting mechanism cuts a tissue sample (59). Vacuum generating mechanism may provide positive air pressure for tissue sample ejection.

11 Claims, 47 Drawing Sheets

(56) References Cited

U.S. PATENT DOCUMENTS

| | | |
|---|---|---|
| 6,860,860 B2 | 3/2005 | Viola |
| 6,899,685 B2 | 5/2005 | Kermode et al. |
| 6,942,627 B2 | 9/2005 | Huitema |
| 6,945,942 B2 | 9/2005 | Van Bladel et al. |
| 6,976,968 B2 | 12/2005 | Ritchart et al. |
| 7,022,085 B2 | 4/2006 | Cooke et al. |
| 7,060,039 B2 | 6/2006 | Voegele |
| 7,063,672 B2 | 6/2006 | Schramm |
| 7,066,893 B2 | 6/2006 | Hibner et al. |
| 7,131,951 B2 | 11/2006 | Angel |
| 7,153,274 B2 | 12/2006 | Stephens et al. |
| 7,169,114 B2 | 1/2007 | Krause |
| 7,189,206 B2 | 3/2007 | Quick et al. |
| 7,189,207 B2 | 3/2007 | Viola |
| 7,229,439 B2 | 6/2007 | Burbank et al. |
| 7,252,641 B2 | 8/2007 | Thompson et al. |
| 7,276,032 B2 | 10/2007 | Hibner |
| 7,278,970 B2 | 10/2007 | Goldenberg |
| 7,311,672 B2 | 12/2007 | Van Bladel et al. |
| 7,390,306 B2 | 6/2008 | Mark |
| 7,419,472 B2 | 9/2008 | Hibner et al. |
| 7,449,000 B2 | 11/2008 | Adams et al. |
| 7,458,940 B2 | 12/2008 | Miller |
| 7,465,278 B2 | 12/2008 | Cicenas et al. |
| 7,470,237 B2 | 12/2008 | Beckman et al. |
| 7,481,775 B2 | 1/2009 | Weikel, Jr. et al. |
| 7,491,177 B2 | 2/2009 | Hibner |
| 7,497,833 B2 | 3/2009 | Miller |
| 7,507,210 B2 | 3/2009 | Hibner et al. |
| 7,517,321 B2 | 4/2009 | McCullough et al. |
| 7,517,322 B2 | 4/2009 | Weikel, Jr. et al. |
| 7,534,242 B2 | 5/2009 | Buehlmann et al. |
| 7,569,053 B2 | 8/2009 | Eggers et al. |
| 7,575,556 B2 | 8/2009 | Speeg et al. |
| 7,611,474 B2 | 11/2009 | Hibner et al. |
| 7,611,475 B2 | 11/2009 | Spero et al. |
| 7,635,340 B2 | 12/2009 | Vetter et al. |
| 7,645,239 B2 | 1/2010 | Heske et al. |
| 7,645,240 B2 | 1/2010 | Thompson et al. |
| 7,648,466 B2 | 1/2010 | Stephens et al. |
| 7,658,718 B2 | 2/2010 | Miller et al. |
| 7,662,109 B2 | 2/2010 | Hibner |
| 7,670,299 B2 | 3/2010 | Beckman et al. |
| 7,693,567 B2 | 4/2010 | Tsonton et al. |
| 7,717,861 B2 | 5/2010 | Weikel et al. |
| 7,740,594 B2 | 6/2010 | Hibner |
| 7,740,596 B2 | 6/2010 | Hibner |
| 7,740,597 B2 | 6/2010 | Cicenas et al. |
| 7,740,598 B2 | 6/2010 | Heske et al. |
| 7,753,857 B2 | 7/2010 | Hibner |
| 7,758,515 B2 | 7/2010 | Hibner |
| 7,762,961 B2 | 7/2010 | Heske et al. |
| 7,766,843 B2 | 8/2010 | Voegele |
| 7,794,410 B2 | 9/2010 | Mikulka et al. |
| 7,794,411 B2 | 9/2010 | Ritchart et al. |
| 7,806,834 B2 | 10/2010 | Beckman et al. |
| 7,806,835 B2 | 10/2010 | Hibner et al. |
| 7,819,819 B2 | 10/2010 | Quick et al. |
| 7,828,745 B2 | 11/2010 | McAlister et al. |
| 7,828,746 B2 | 11/2010 | Teague |
| 7,828,747 B2 | 11/2010 | Heske et al. |
| 7,828,748 B2 | 11/2010 | Hibner |
| 7,837,630 B2 | 11/2010 | Nicoson et al. |
| 7,837,632 B2 | 11/2010 | Stephens et al. |
| 7,846,109 B2 | 12/2010 | Parihar et al. |
| 7,850,620 B2 | 12/2010 | Miller et al. |
| 7,854,706 B2 | 12/2010 | Hibner |
| 7,854,707 B2 | 12/2010 | Hibner et al. |
| 7,858,038 B2 | 12/2010 | Andreyko et al. |
| 7,862,517 B2 | 1/2011 | Tsonton et al. |
| 7,862,518 B2 | 1/2011 | Parihar |
| 7,867,173 B2 | 1/2011 | Hibner et al. |
| 7,883,476 B2 | 2/2011 | Miller et al. |
| 7,895,725 B2 | 3/2011 | Beckman et al. |
| 7,896,817 B2 | 3/2011 | Garrison |
| 7,918,803 B2 | 4/2011 | Ritchart et al. |
| 7,918,804 B2 | 4/2011 | Monson et al. |
| 7,938,786 B2 | 5/2011 | Ritchie et al. |
| 7,959,580 B2 | 6/2011 | McCullough et al. |
| 7,963,928 B2 | 6/2011 | Krause |
| 7,981,049 B2 | 7/2011 | Ritchie et al. |
| 7,981,051 B2 | 7/2011 | Quick et al. |
| 7,988,642 B2 | 8/2011 | Hardin et al. |
| 8,002,713 B2 | 8/2011 | Heske et al. |
| 8,012,102 B2 | 9/2011 | McCullough et al. |
| 8,016,772 B2 | 9/2011 | Heske et al. |
| 8,016,844 B2 | 9/2011 | Privitera et al. |
| 8,038,627 B2 | 10/2011 | Hibner |
| 8,048,003 B2 | 11/2011 | Nicoson et al. |
| 8,052,614 B2 | 11/2011 | Heske et al. |
| 8,052,615 B2 | 11/2011 | Reuber et al. |
| 8,052,616 B2 | 11/2011 | Andrisek et al. |
| 2001/0011156 A1 | 8/2001 | Viola et al. |
| 2002/0156395 A1 | 10/2002 | Stephens et al. |
| 2003/0158521 A1 | 8/2003 | Ameri |
| 2003/0229292 A1 | 12/2003 | Hibner et al. |
| 2005/0027209 A1 | 2/2005 | Eggers |
| 2005/0065453 A1 | 3/2005 | Shabaz et al. |
| 2005/0101880 A1 | 5/2005 | Cicenas et al. |
| 2005/0203439 A1 | 9/2005 | Heske et al. |
| 2005/0203441 A1 | 9/2005 | Voegele |
| 2005/0212175 A1 | 9/2005 | Tsonton et al. |
| 2005/0215921 A1 | 9/2005 | Hibner et al. |
| 2005/0215922 A1 | 9/2005 | Tsonton et al. |
| 2006/0009712 A1 | 1/2006 | Van Bladel et al. |
| 2006/0074343 A1 | 4/2006 | Hibner |
| 2006/0074345 A1 | 4/2006 | Hibner |
| 2006/0173377 A1 | 8/2006 | McCullough et al. |
| 2006/0200041 A1 | 9/2006 | Weikel, Jr. et al. |
| 2007/0027407 A1 | 2/2007 | Miller |
| 2007/0032743 A1 | 2/2007 | Hibner |
| 2007/0055173 A1 | 3/2007 | DeLonzor et al. |
| 2007/0106176 A1* | 5/2007 | Mark ............ A61B 10/0275 600/566 |
| 2007/0149893 A1 | 6/2007 | Heske et al. |
| 2007/0185411 A1 | 8/2007 | Hibner |
| 2007/0208272 A1 | 9/2007 | Voegele |
| 2007/0219460 A1 | 9/2007 | Goldenberg |
| 2007/0255170 A1 | 11/2007 | Hibner et al. |
| 2008/0004545 A1 | 1/2008 | Garrison |
| 2008/0103413 A1 | 5/2008 | Cicenas et al. |
| 2008/0114264 A1 | 5/2008 | Weikel, Jr. et al. |
| 2008/0269683 A1 | 10/2008 | Bikovsky |
| 2008/0281226 A1 | 11/2008 | Peters |
| 2008/0281266 A1 | 11/2008 | Walton et al. |
| 2008/0306406 A1 | 12/2008 | Thompson et al. |
| 2009/0082696 A1 | 3/2009 | Nicoson |
| 2009/0087249 A1 | 4/2009 | Flagle et al. |
| 2009/0143698 A1 | 6/2009 | Janssens |
| 2009/0227893 A1 | 9/2009 | Coonahan et al. |
| 2009/0260755 A1 | 10/2009 | Beckman et al. |
| 2009/0326412 A1 | 12/2009 | Pakter |
| 2010/0030104 A1 | 2/2010 | Hardin |
| 2010/0030108 A1 | 2/2010 | Anderson et al. |
| 2010/0063416 A1 | 3/2010 | Cicenas et al. |
| 2010/0113971 A1 | 5/2010 | Hibner |
| 2010/0113973 A1 | 5/2010 | Hibner et al. |
| 2010/0114031 A1 | 5/2010 | Jarial et al. |
| 2010/0152610 A1 | 6/2010 | Parihar et al. |
| 2010/0152611 A1* | 6/2010 | Parihar ............ A61B 10/0275 600/566 |
| 2010/0160818 A1 | 6/2010 | Haberstich et al. |
| 2010/0160819 A1 | 6/2010 | Parihar et al. |
| 2010/0160820 A1 | 6/2010 | Weikel, Jr. et al. |
| 2010/0160826 A1 | 6/2010 | Parihar |
| 2010/0198066 A1 | 8/2010 | Voegele |
| 2010/0228146 A1 | 9/2010 | Hibner |
| 2010/0234760 A1 | 9/2010 | Almazan |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0021945 A1 | 1/2011 | Stephens et al. |

(56) References Cited

U.S. PATENT DOCUMENTS

| | | |
|---|---|---|
| 2011/0046513 A1* | 2/2011 | Hibner ............... A61B 10/0275 600/567 |
| 2011/0071431 A1 | 3/2011 | Speeg et al. |
| 2011/0071433 A1 | 3/2011 | Hibner et al. |
| 2011/0087173 A1 | 4/2011 | Sibbet, Jr. et al. |
| 2011/0112437 A1 | 5/2011 | Beckman et al. |
| 2011/0144532 A1 | 6/2011 | Monson et al. |
| 2011/0152715 A1 | 6/2011 | Delap et al. |
| 2011/0160611 A1 | 6/2011 | Ritchart et al. |
| 2011/0201964 A1 | 8/2011 | Speeg et al. |
| 2011/0208086 A1 | 8/2011 | Hibner et al. |
| 2011/0208088 A1 | 8/2011 | Leimbach et al. |

FOREIGN PATENT DOCUMENTS

| | | |
|---|---|---|
| EP | 2838435 | 10/2013 |
| WO | 2011/097494 A2 | 8/2011 |
| WO | 2013158072 A1 | 10/2013 |

OTHER PUBLICATIONS

Brian S. Englander, M.D., "An Evaluation of the Suros Celero Vacuum Assisted Handheld Device for Ultrasonic Guided Breast Biopsies," HOLOGIC, research overview, Mar. 2008 (United States).

Mammotome Biopsy System, Devicor Medical Products, Inc., website, 2011 (United States).

Mammotome platform, Devicor Medical Products, Inc., website, 2012 (United States).

Encor Enspire, C.R. Bard, Inc., catalog, 2008 (United States).

Comprehensive Solutions in Ultrasound-guided Breast Biopsy, HOLOGIC, catalog, Mar. 2011 (United States).

Vacora Breast Biopsy System, C.R. Bard, Inc., website, 2011 (United States).

International Search Report and Written Opinion, PCT/US2012/033851, Aug. 6, 2012.

Supplementary European Search report of related European Patent Application No. 12874394.5.

* cited by examiner

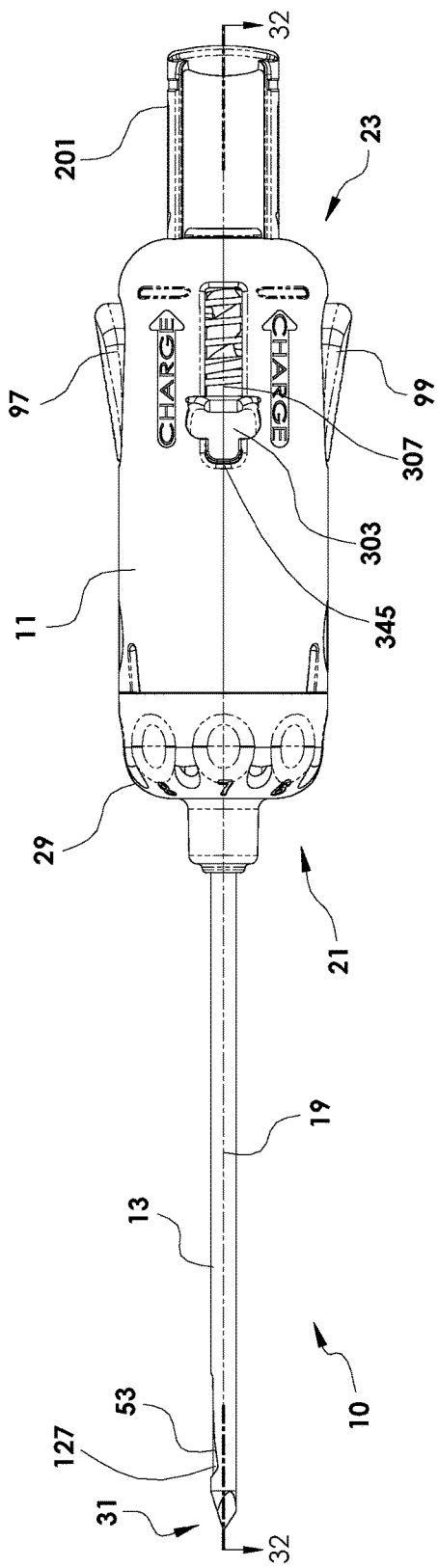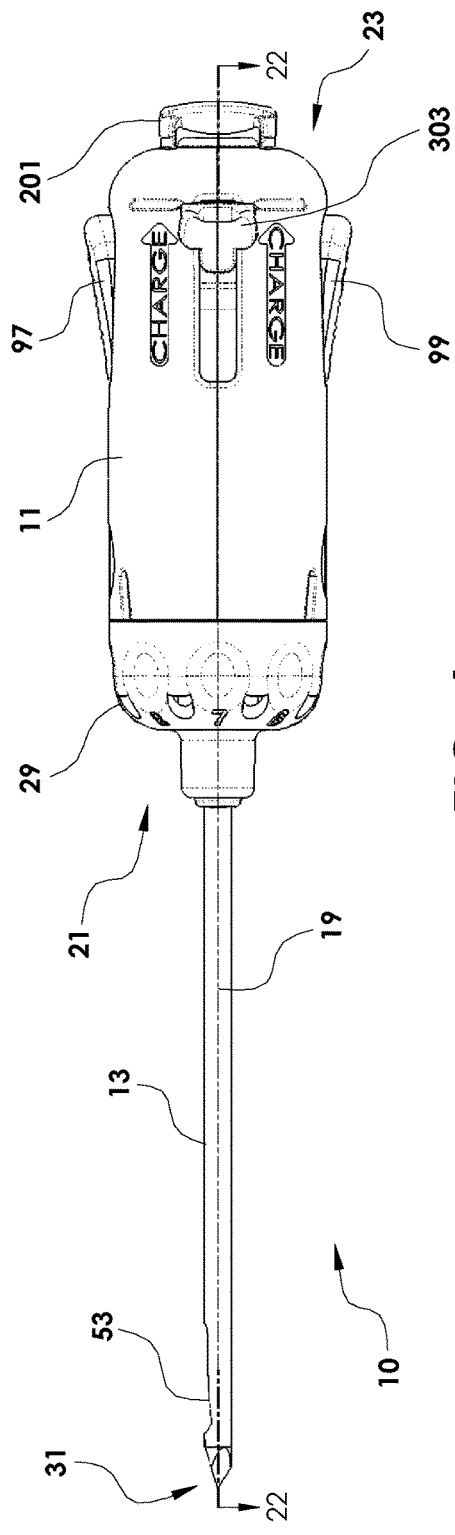

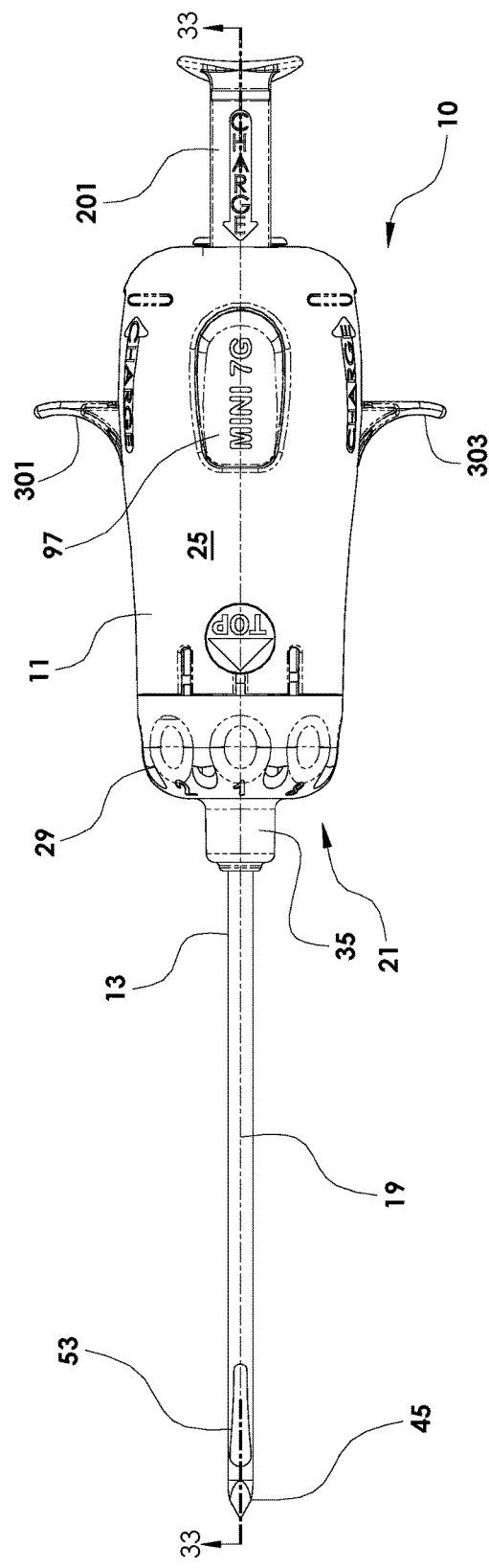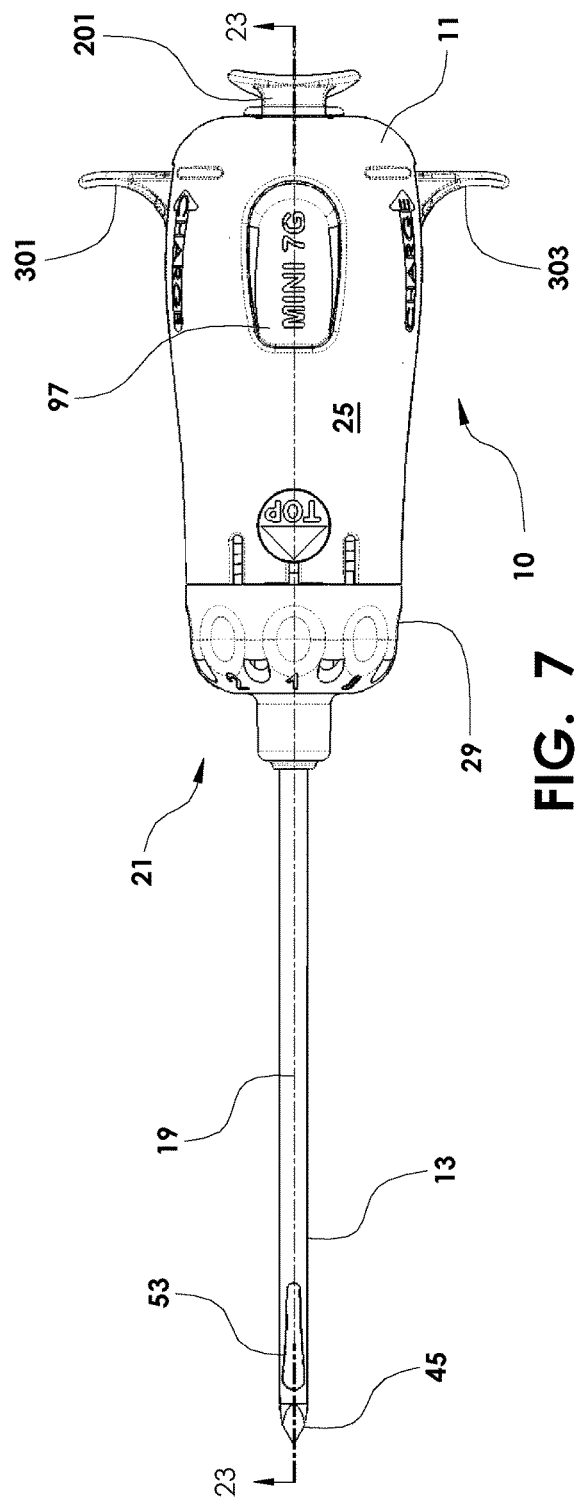
FIG. 6
FIG. 7

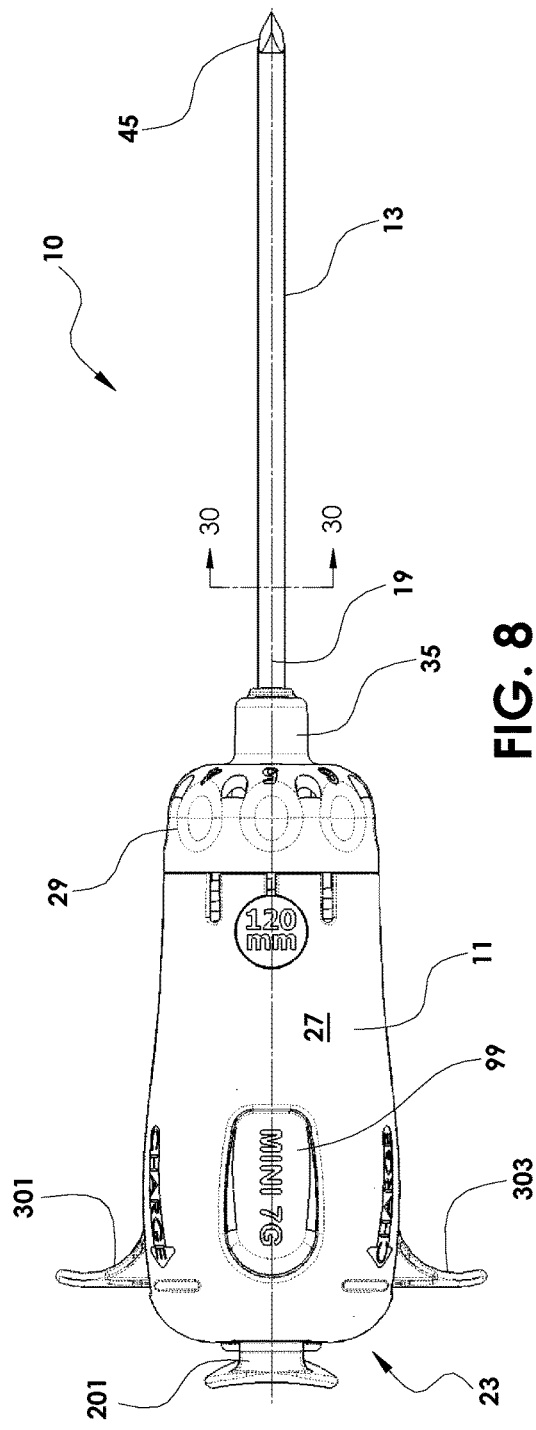
FIG. 8
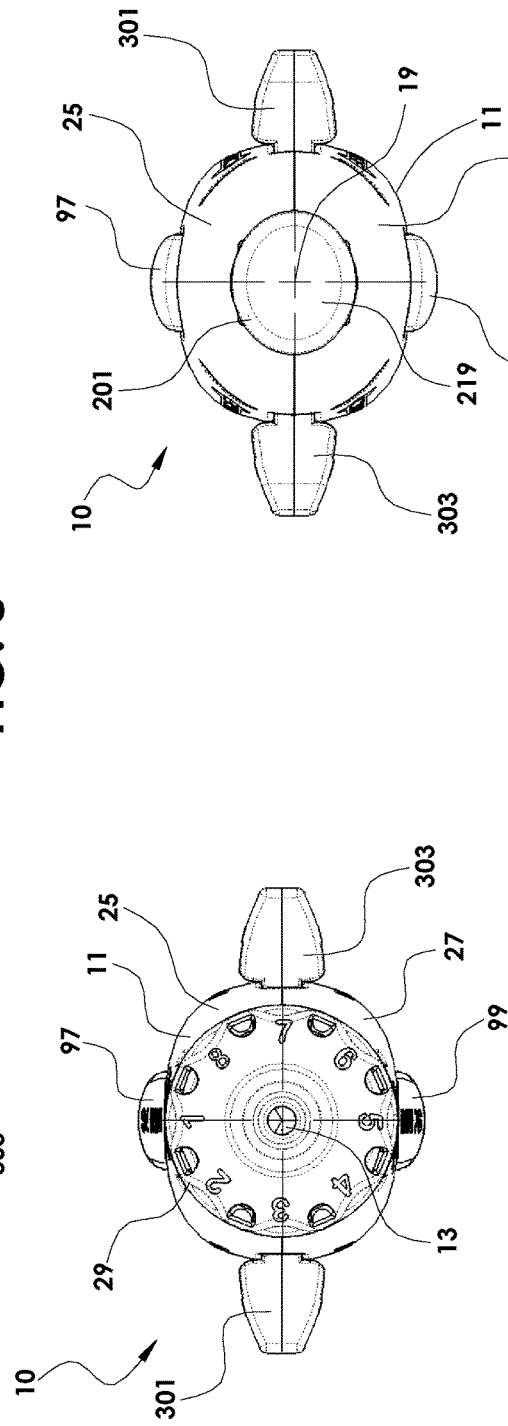
FIG. 9
FIG. 10

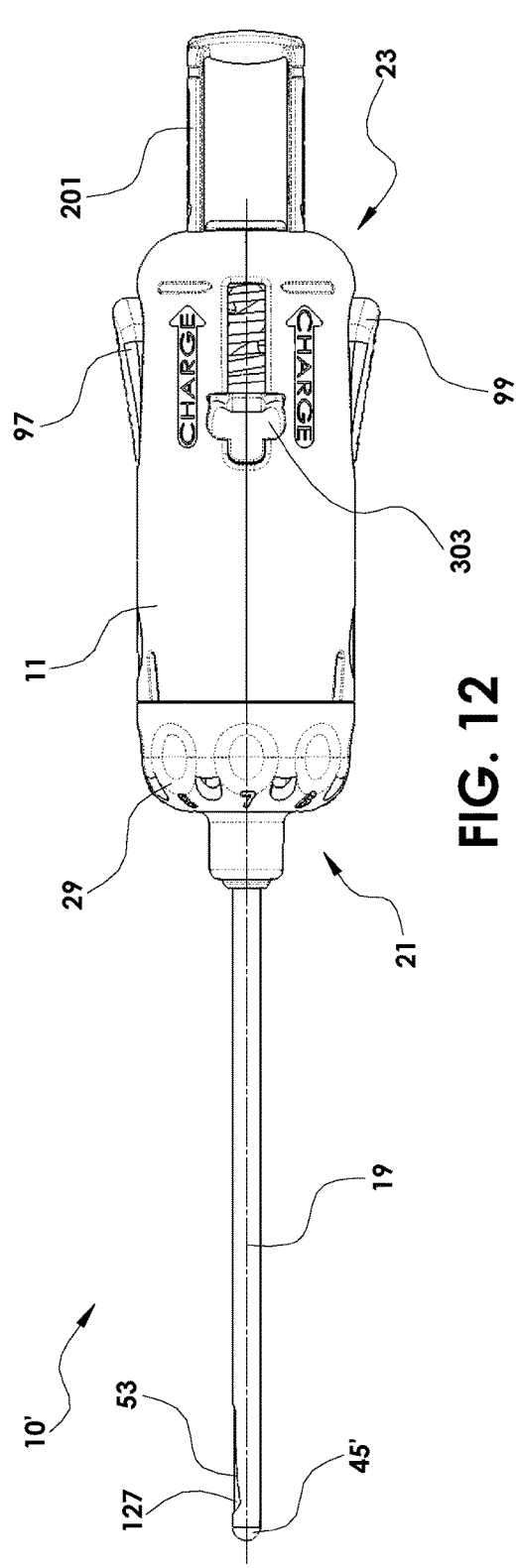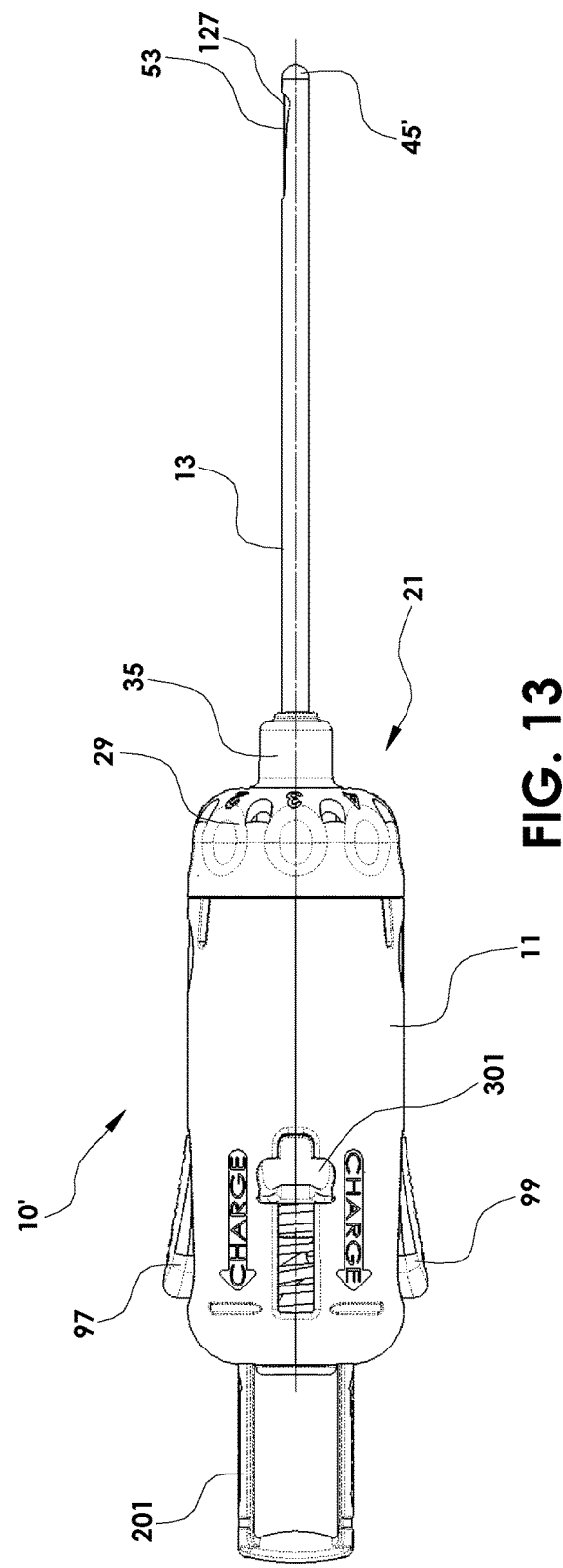

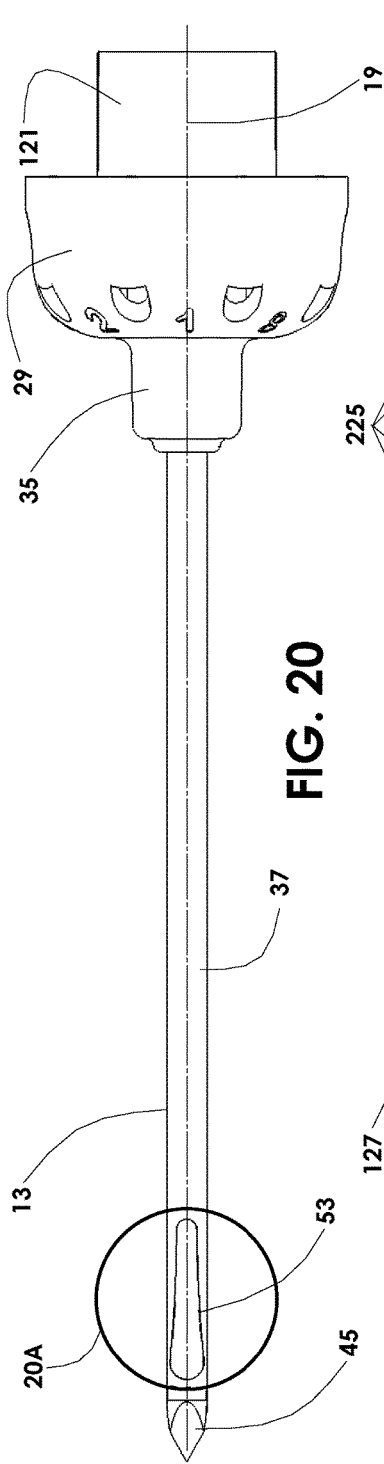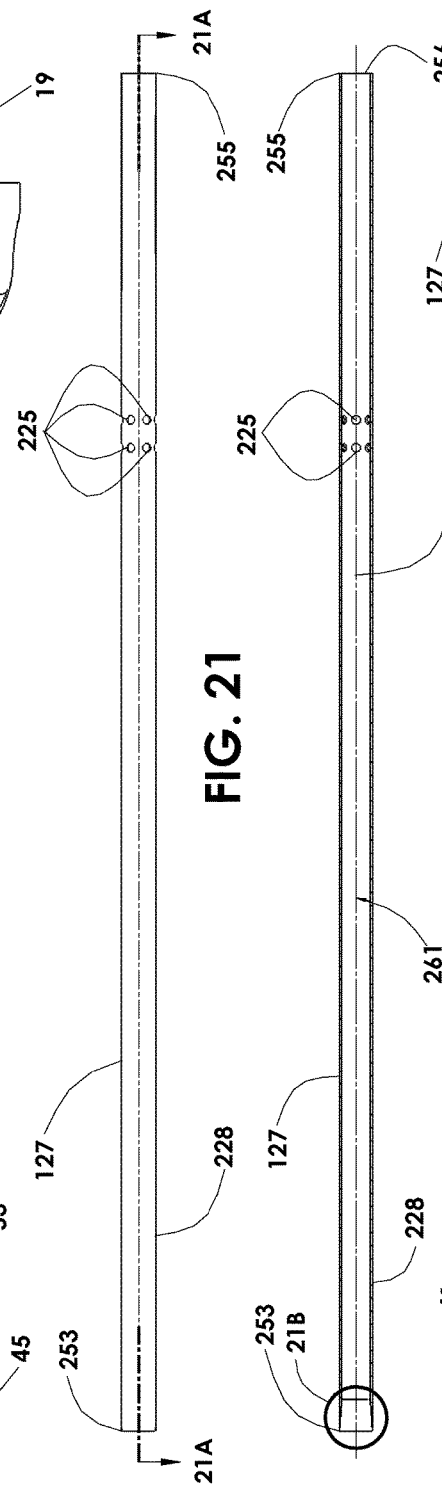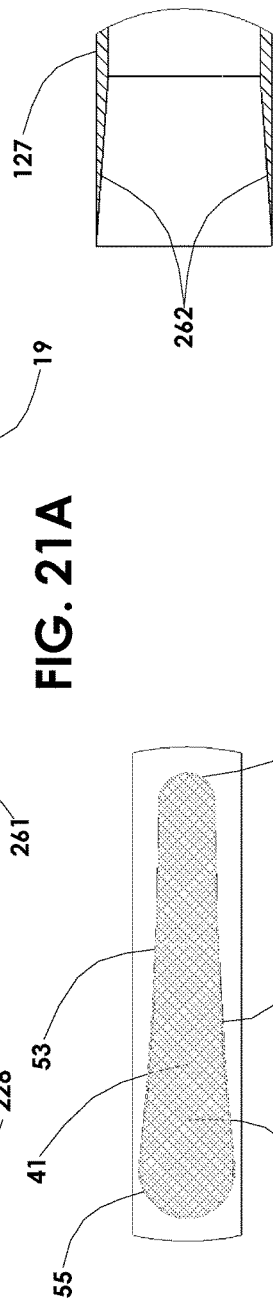
FIG. 20
FIG. 20A
FIG. 21
FIG. 21A
FIG. 21B

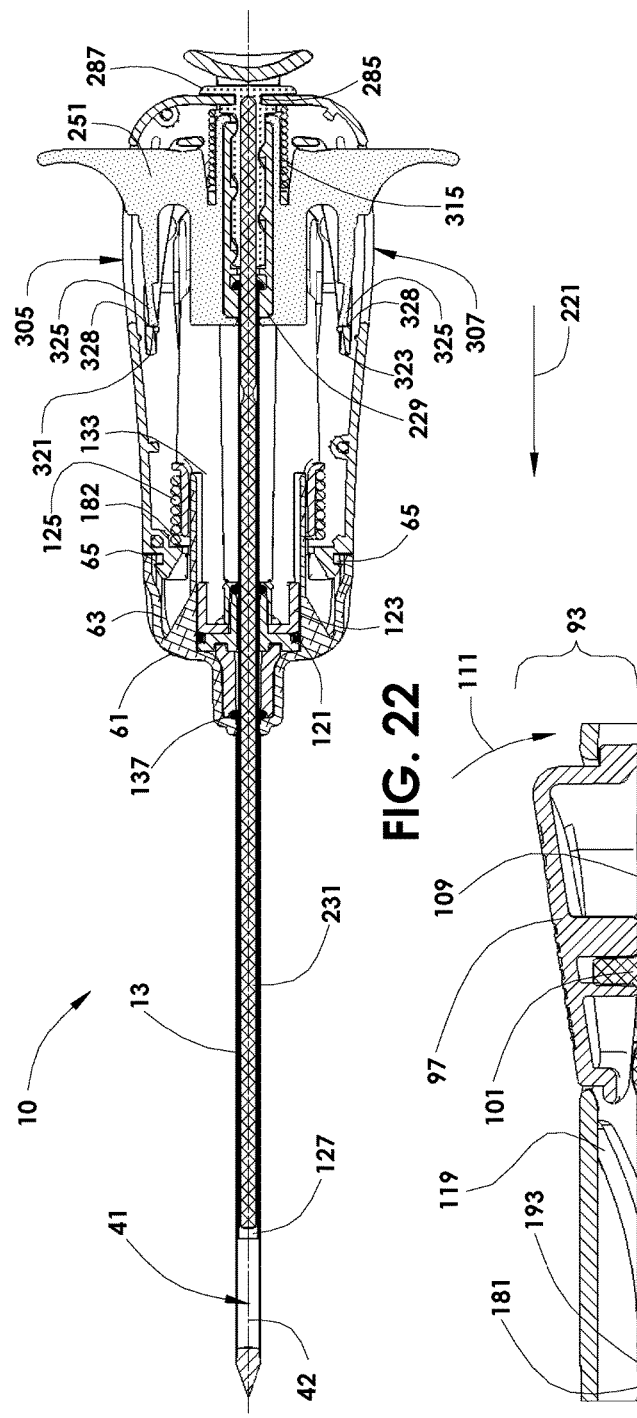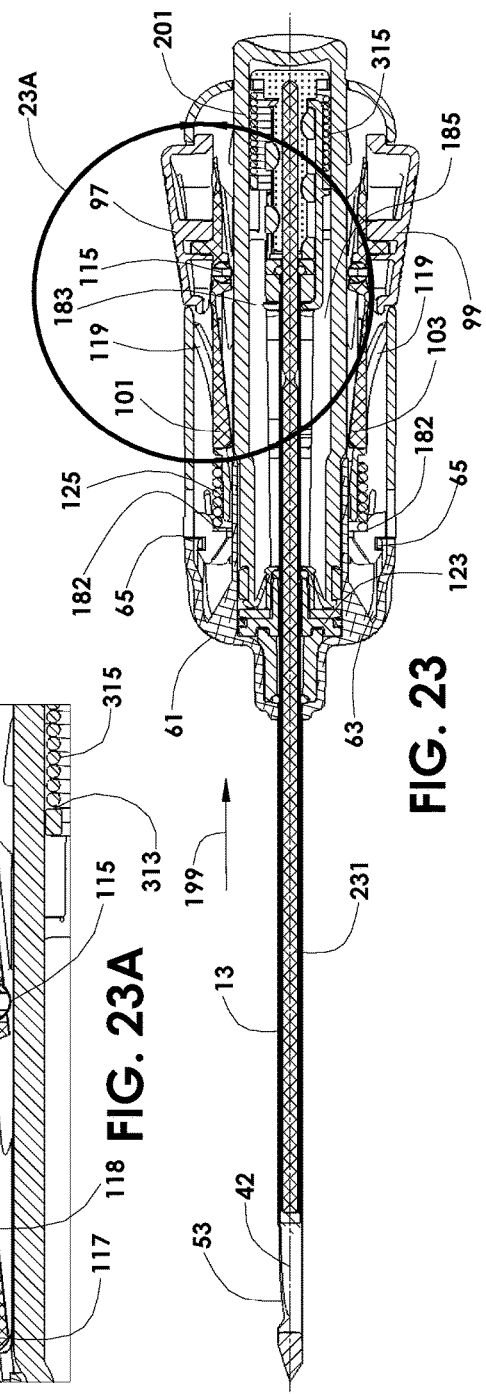

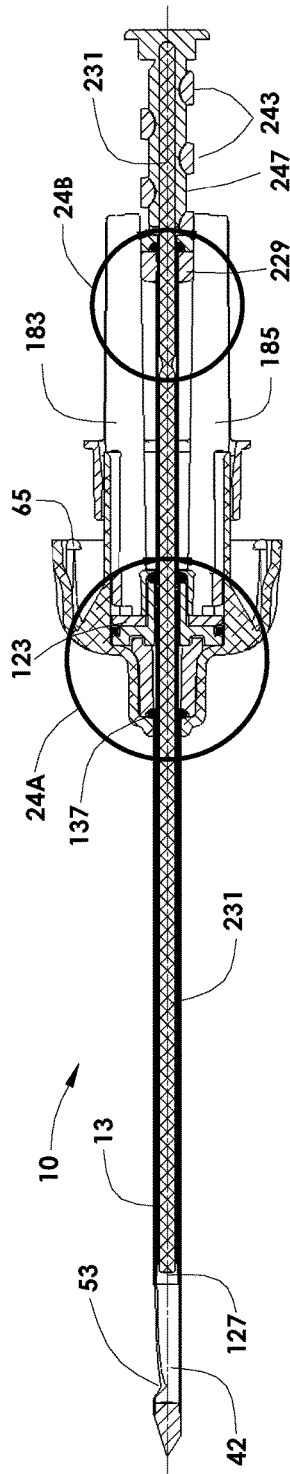
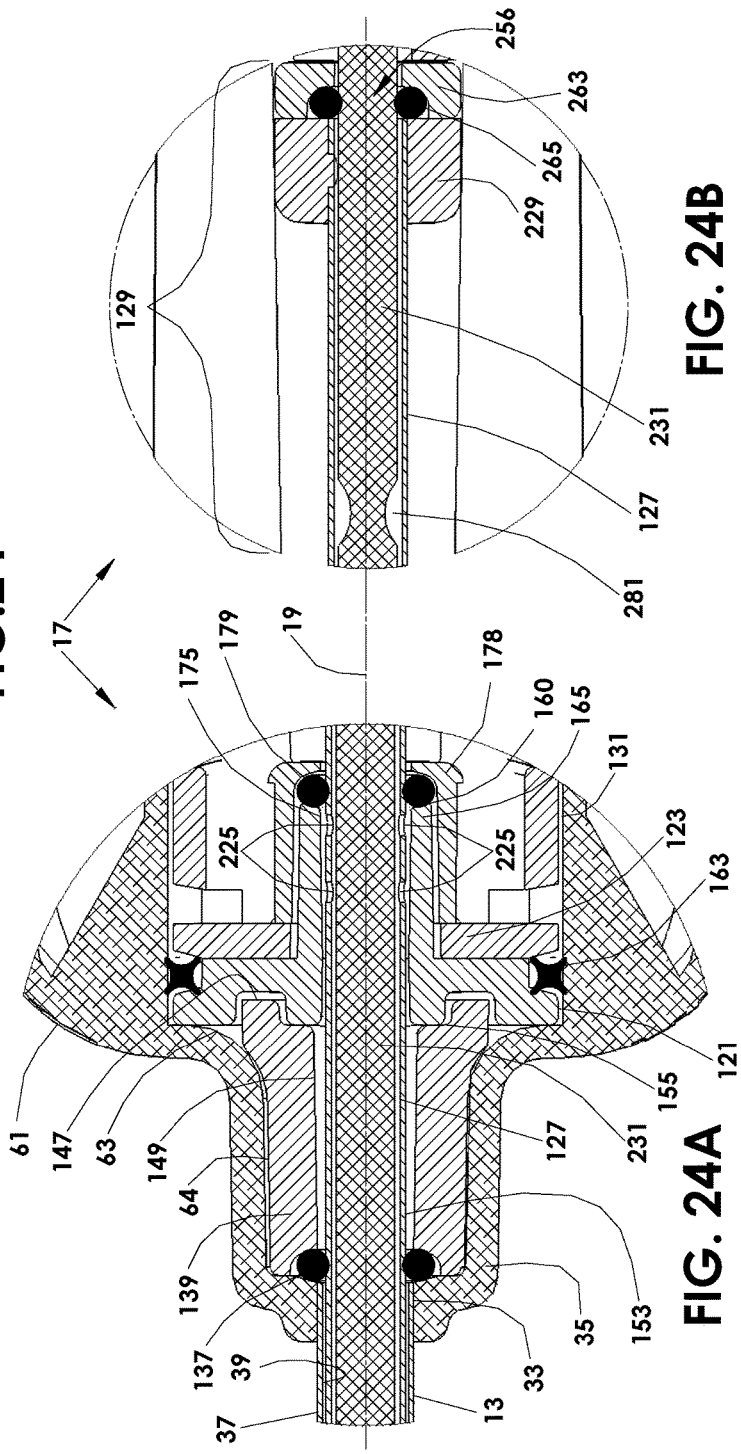
FIG. 24
FIG. 24A
FIG. 24B

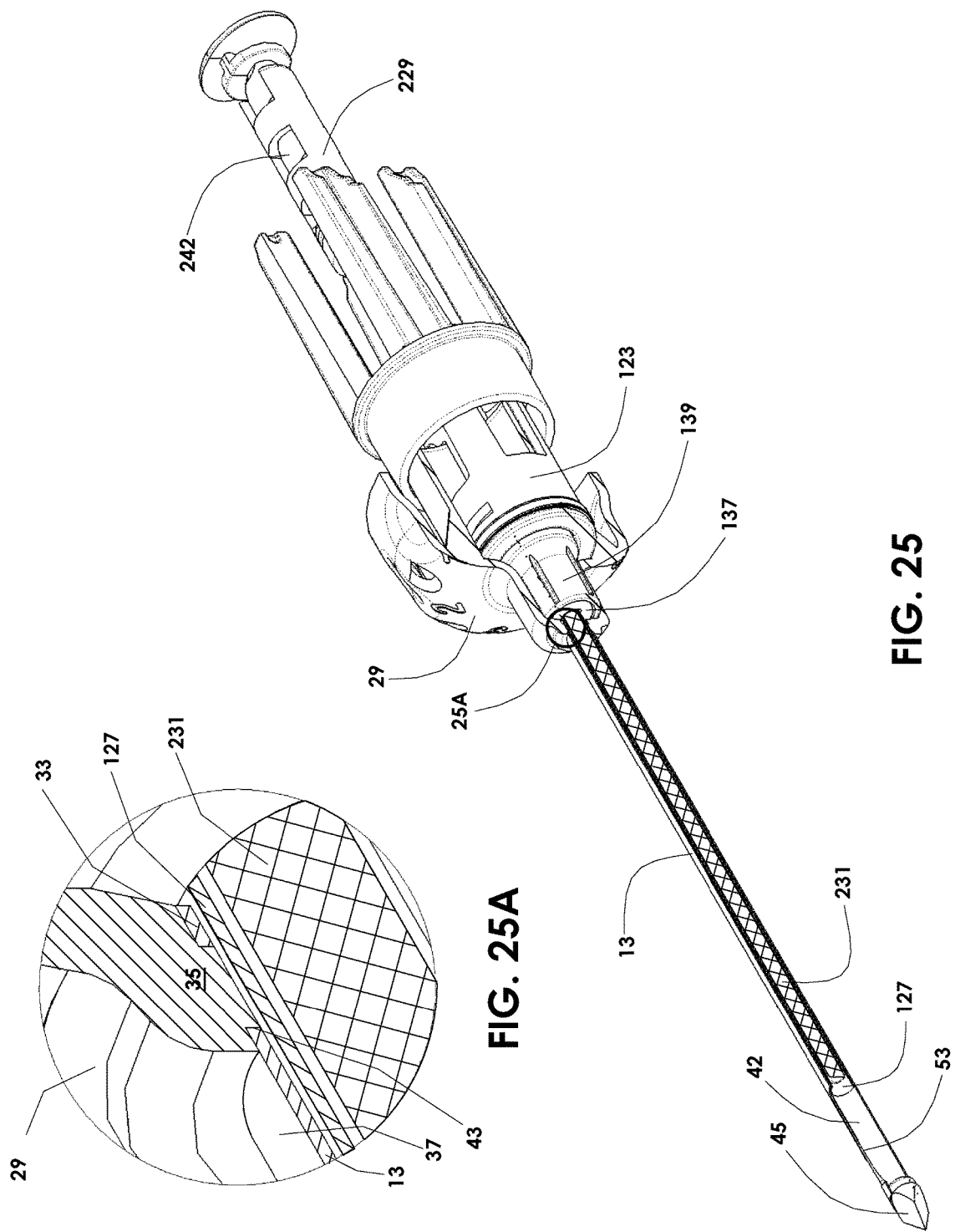

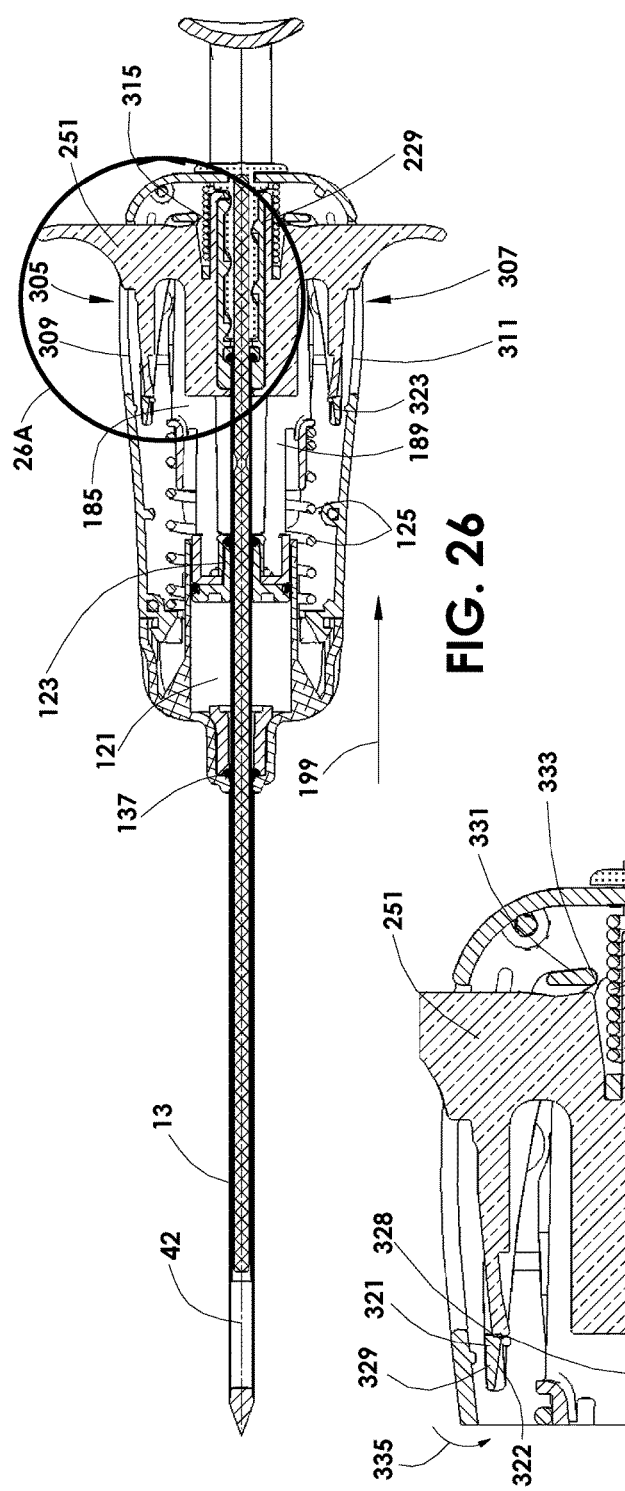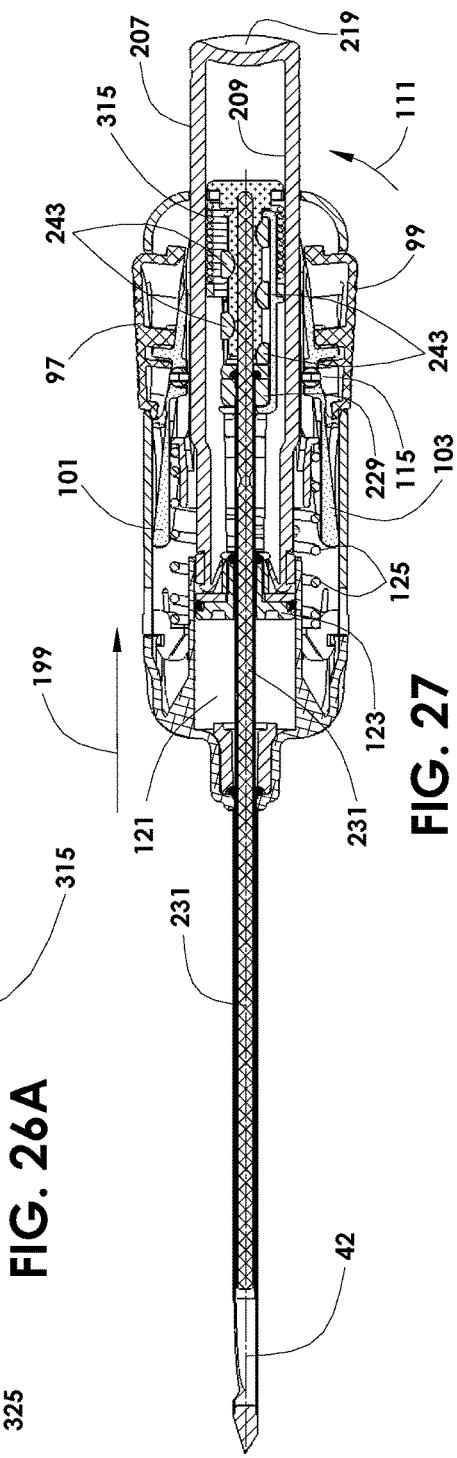

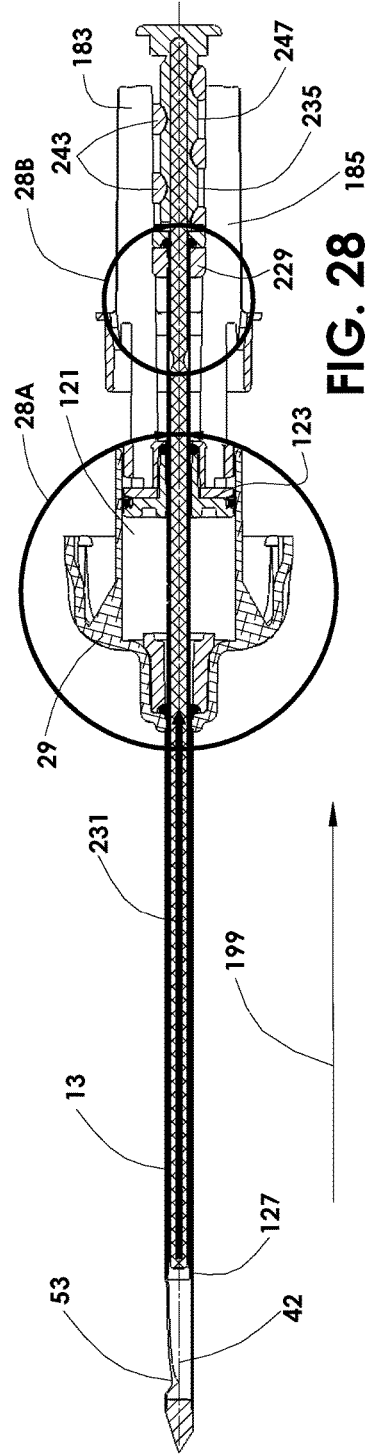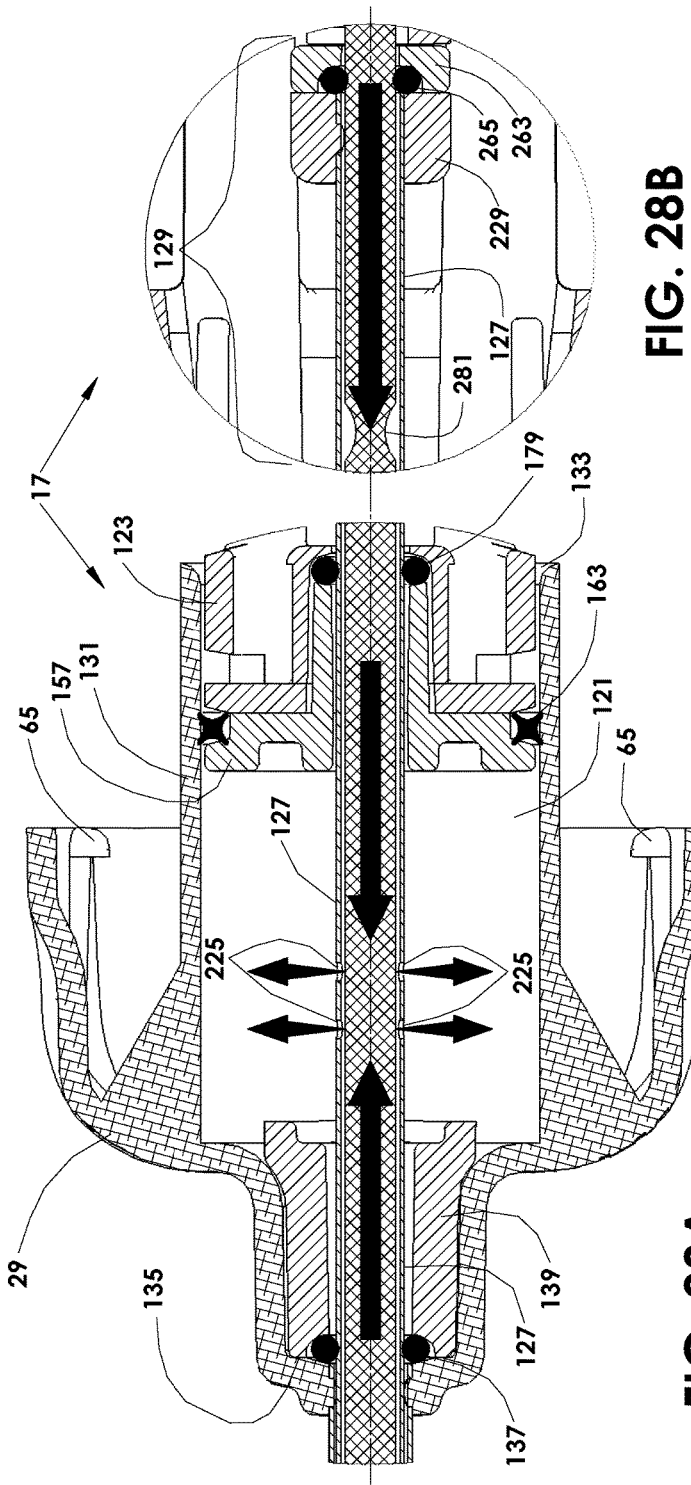
FIG. 28
FIG. 28A
FIG. 28B

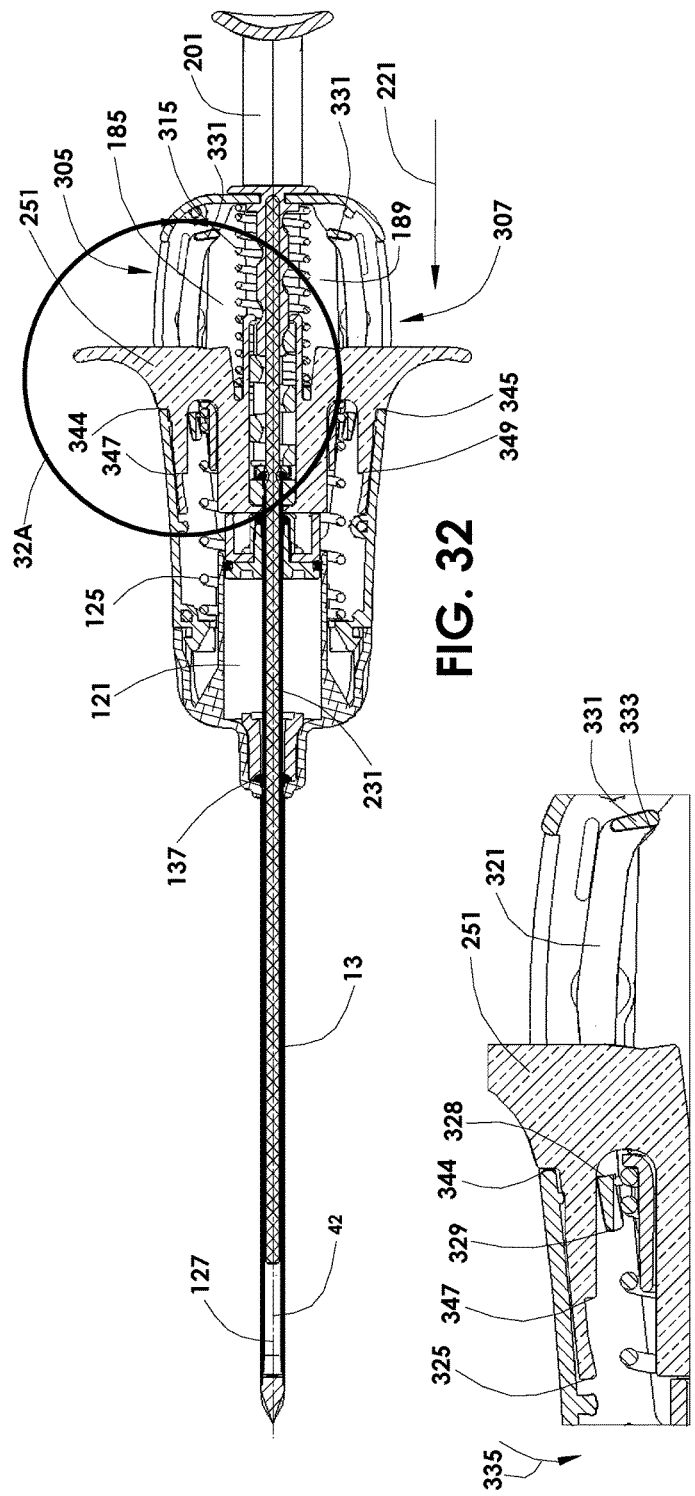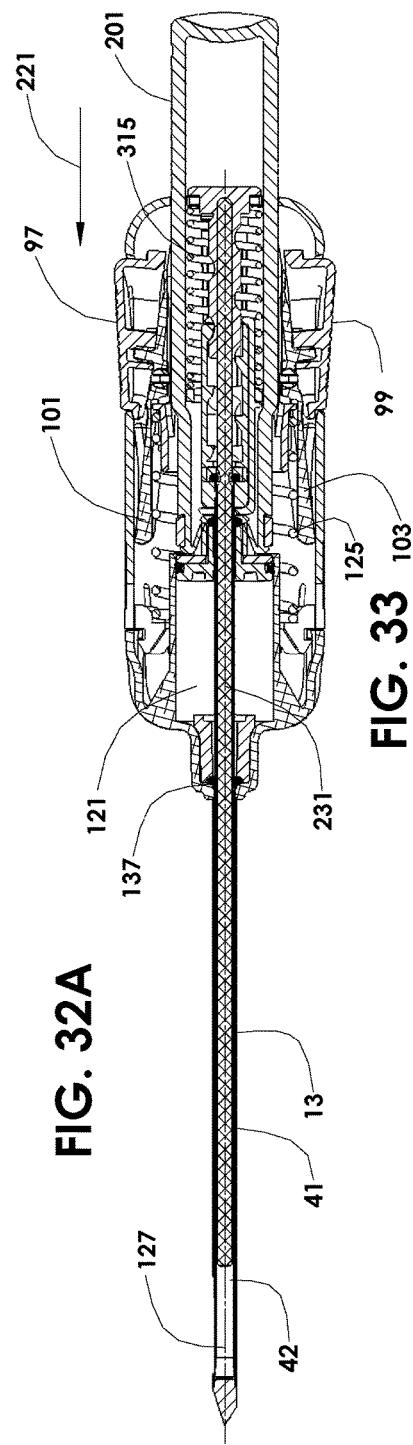

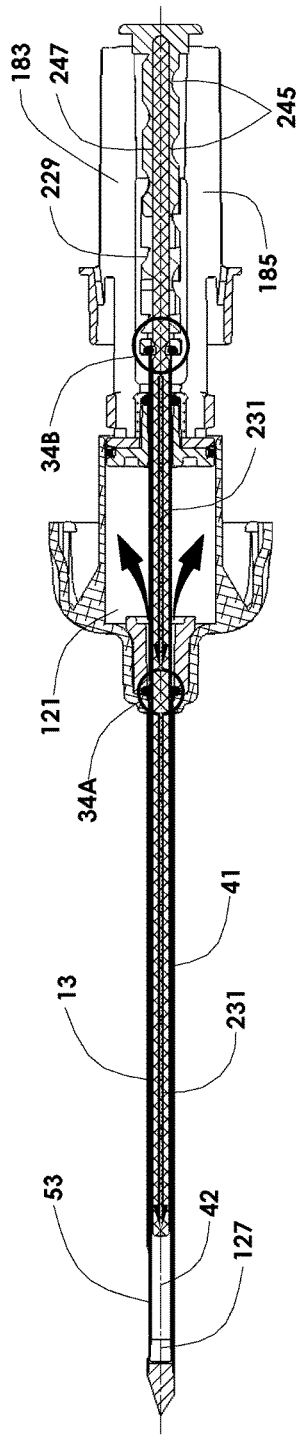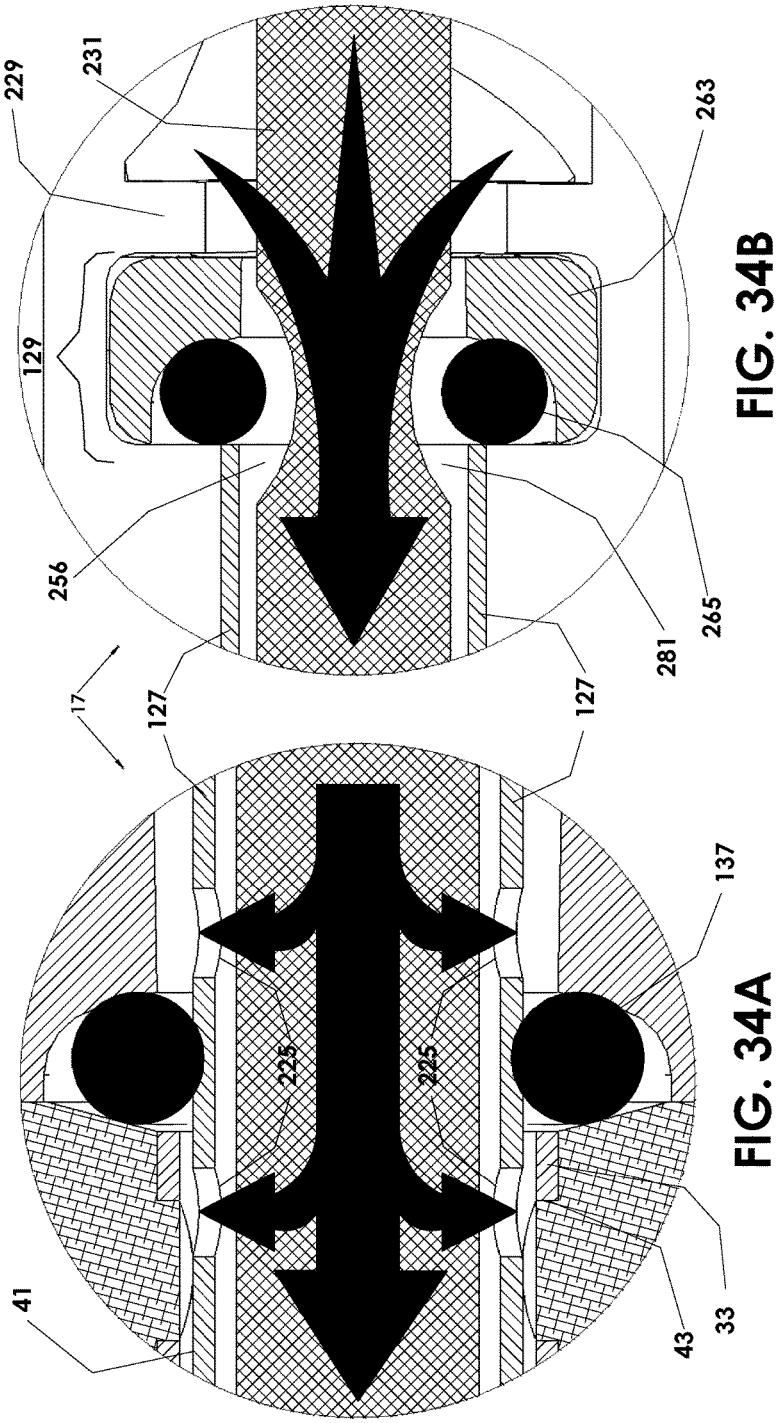

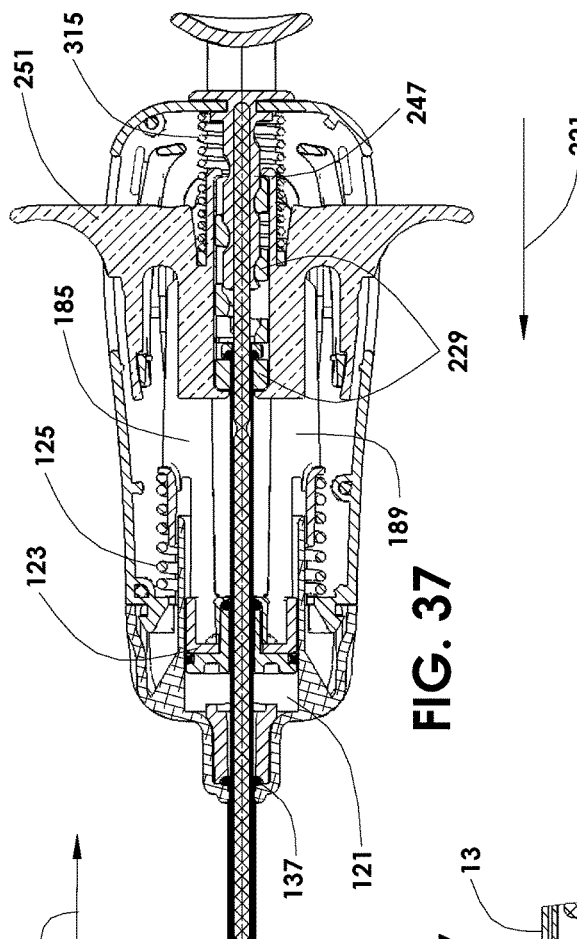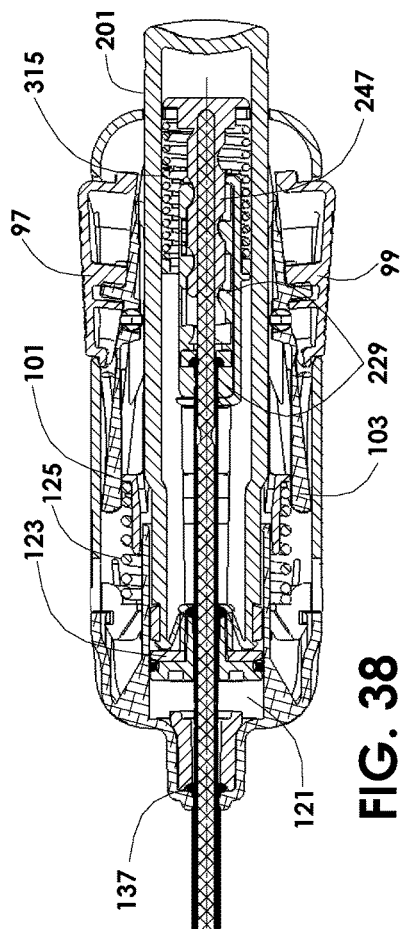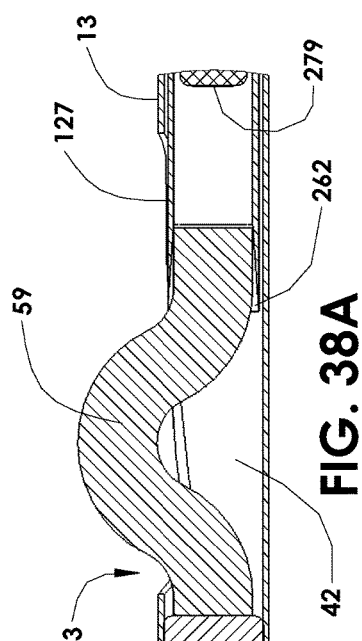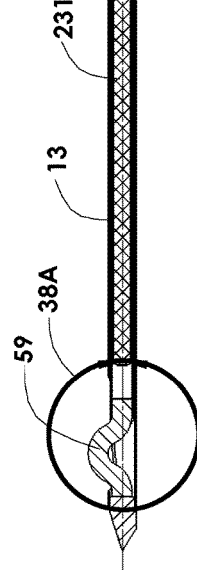

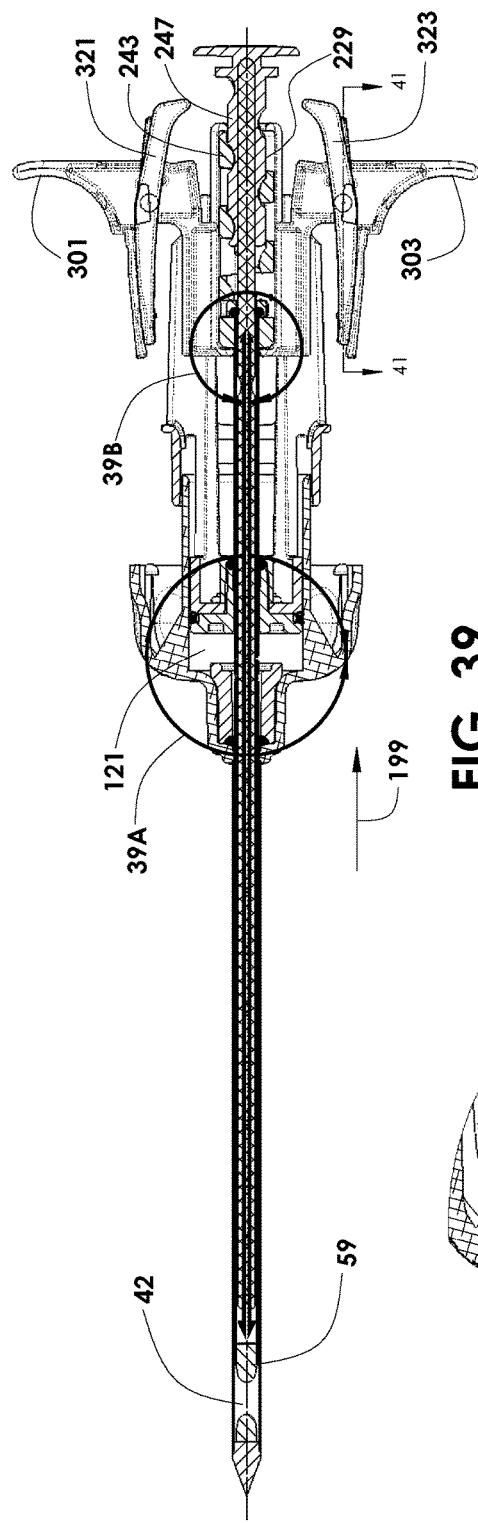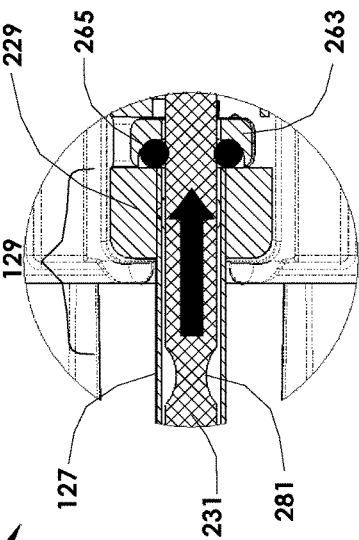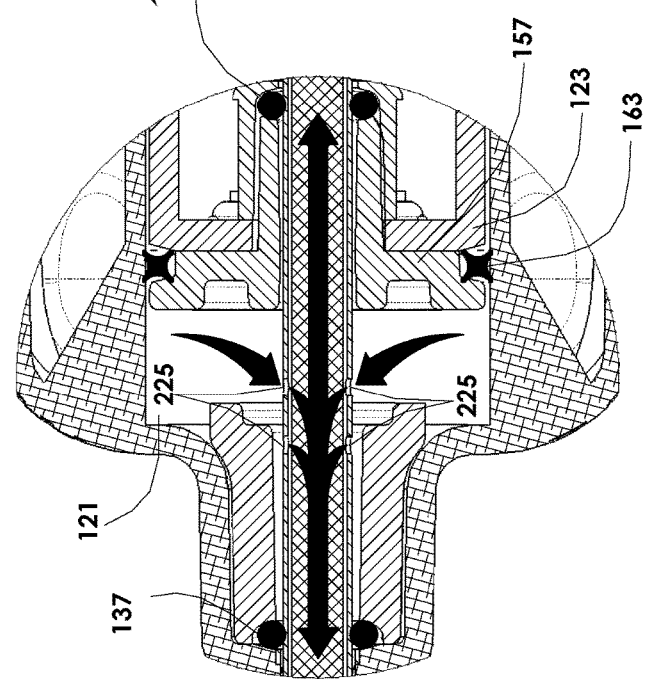

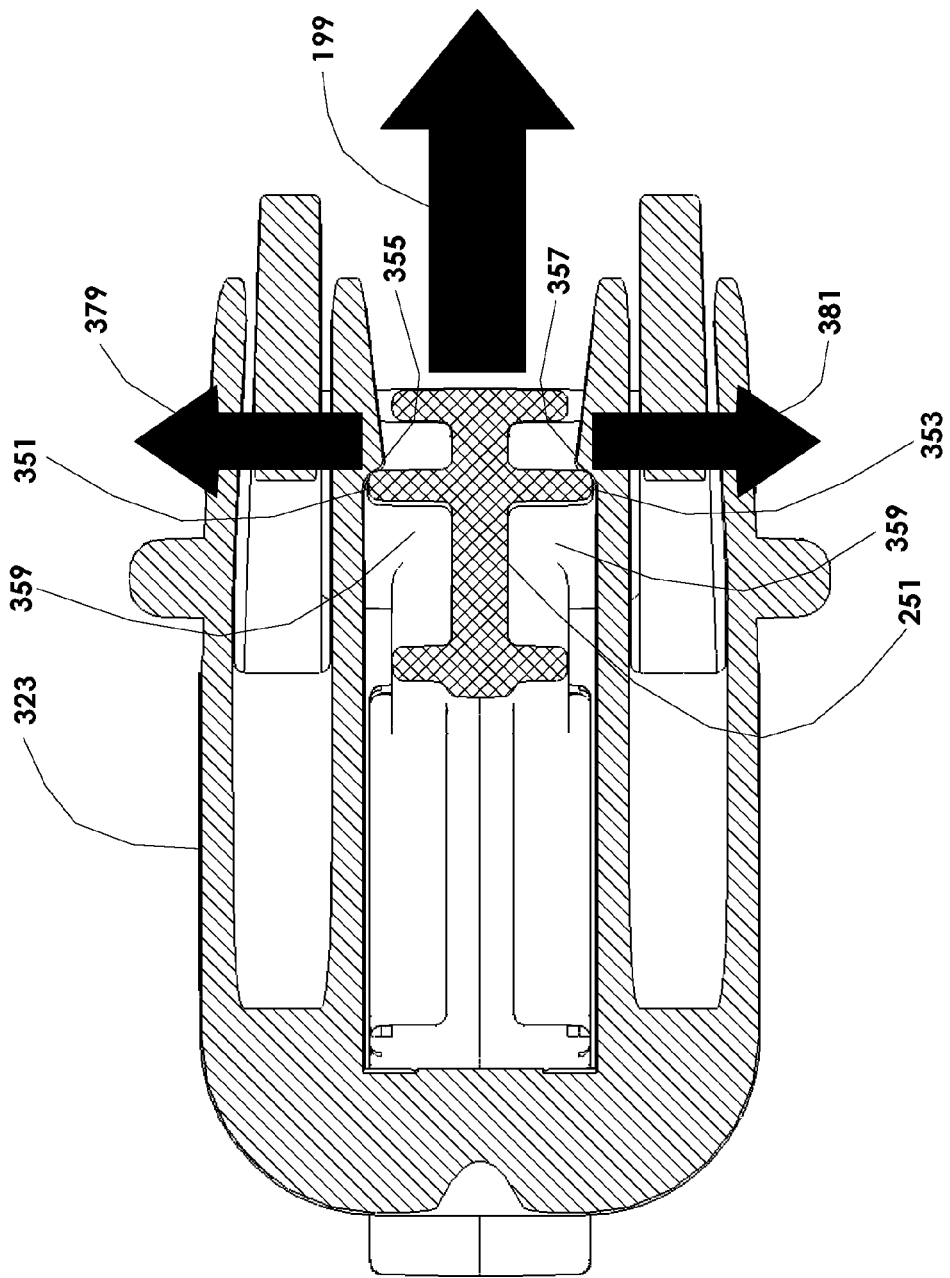

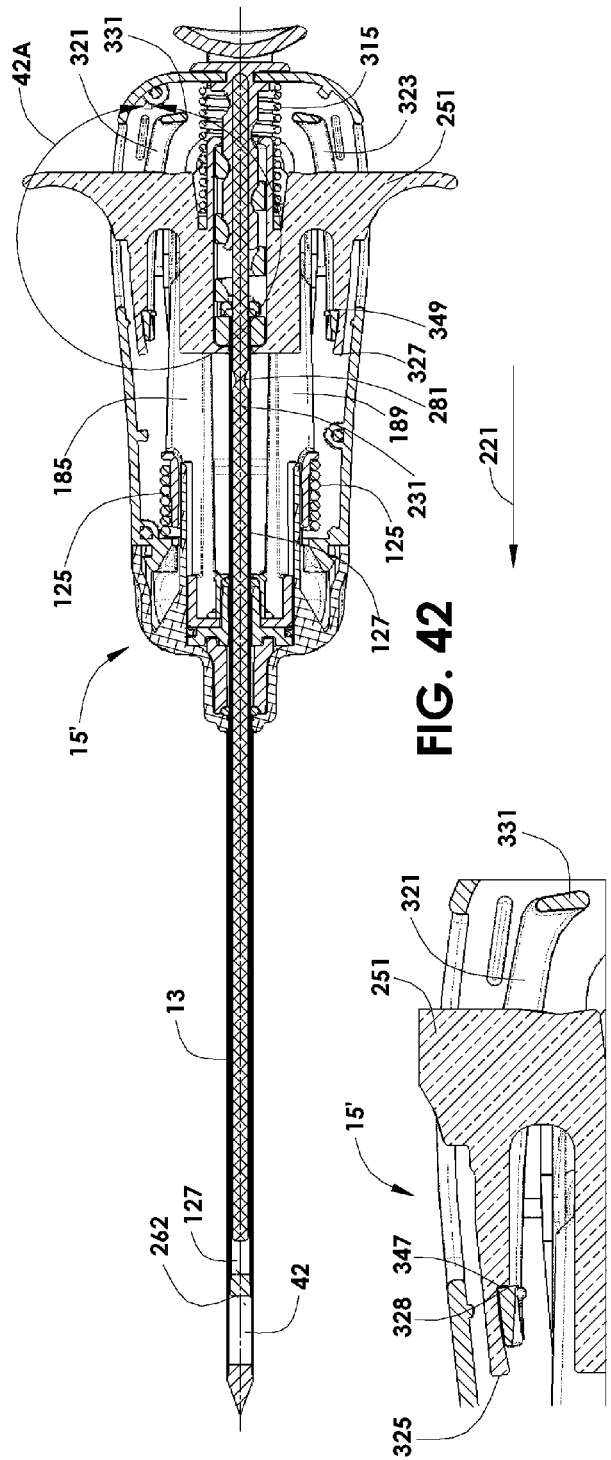

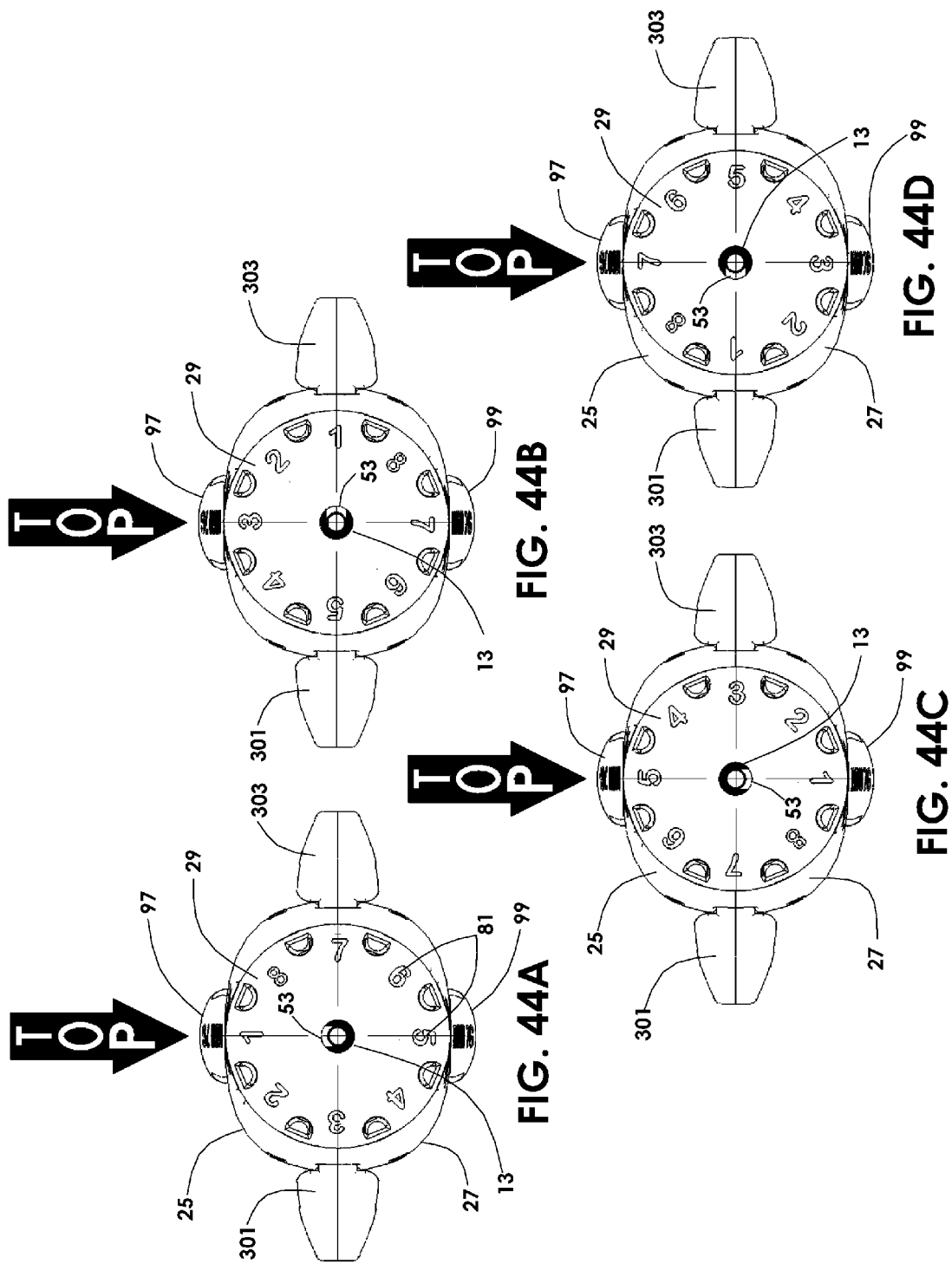

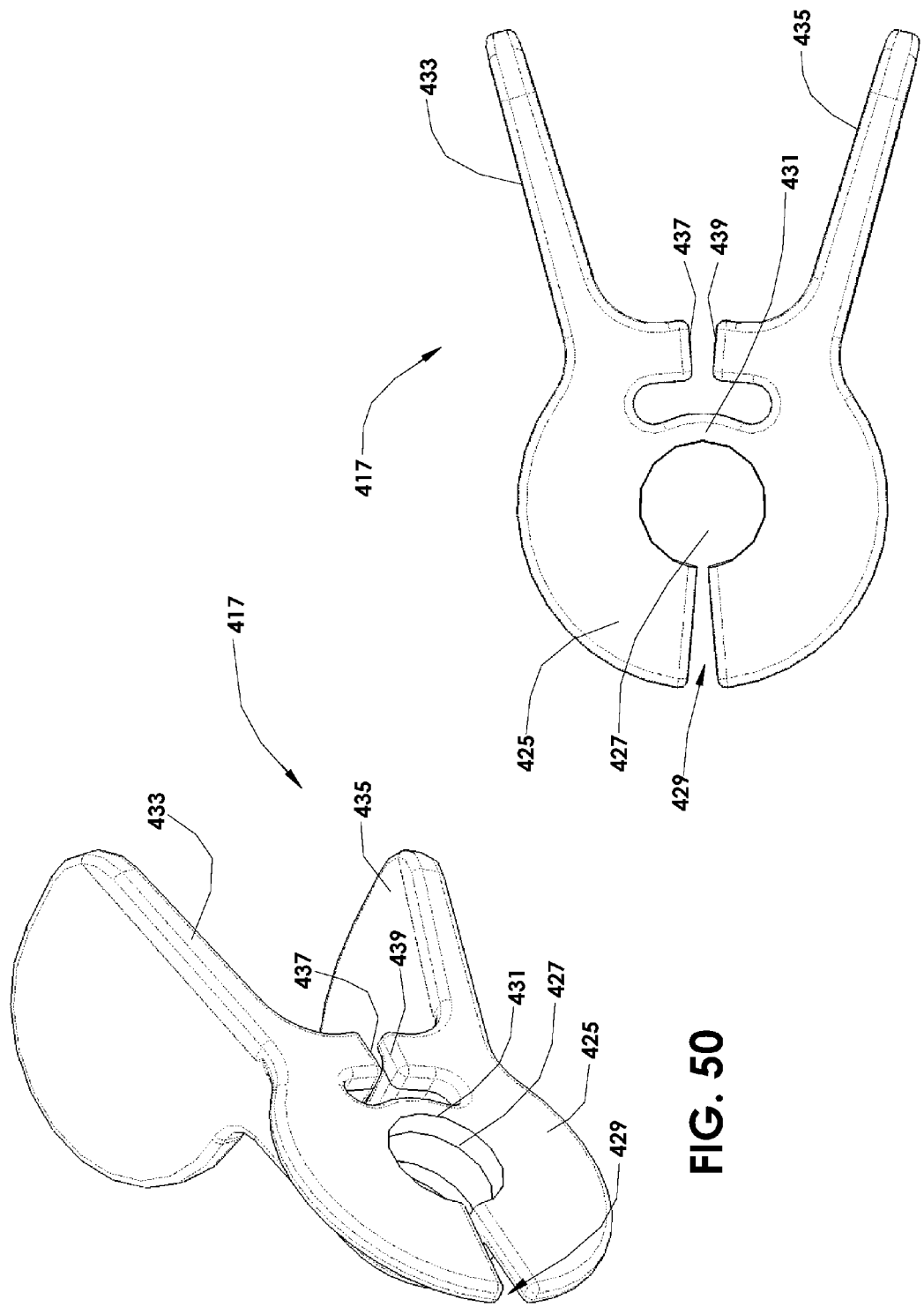

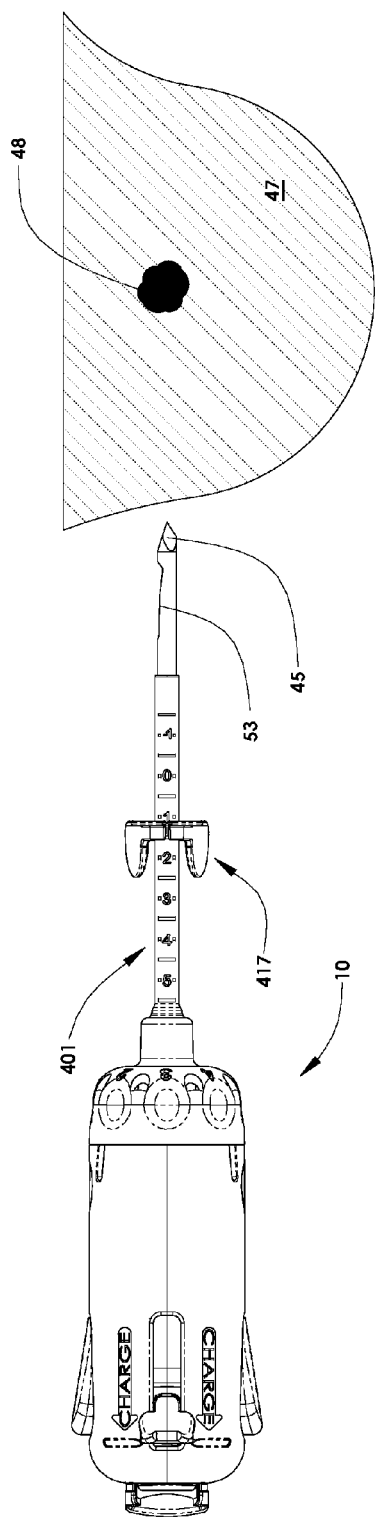
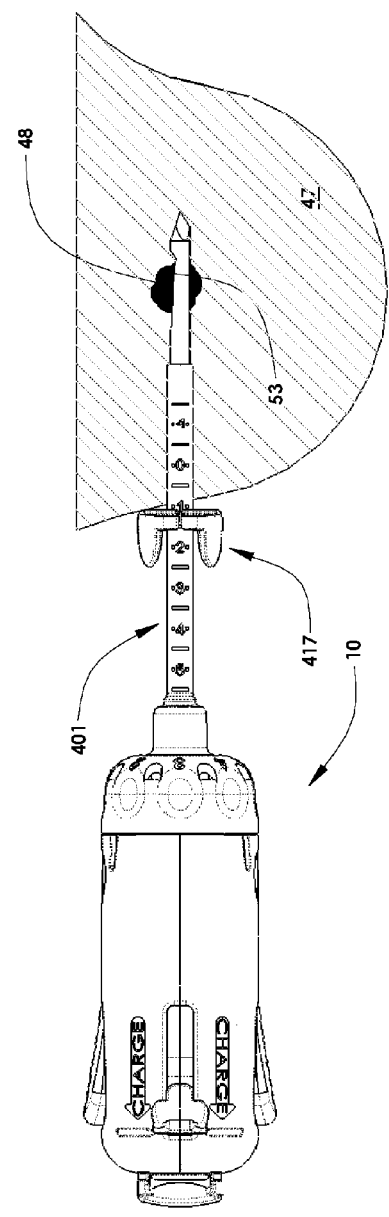
FIG. 54
FIG. 55

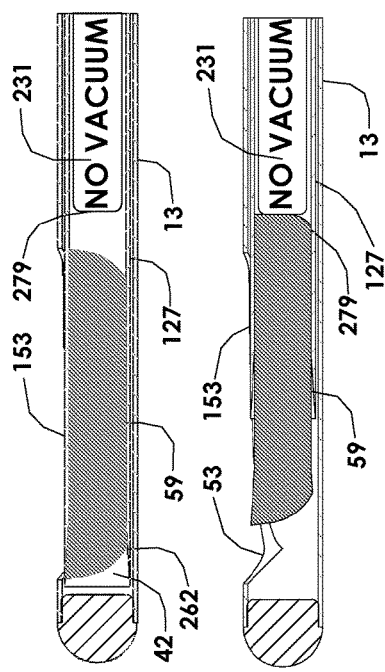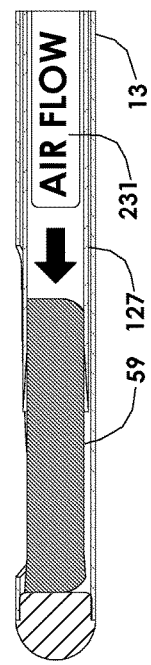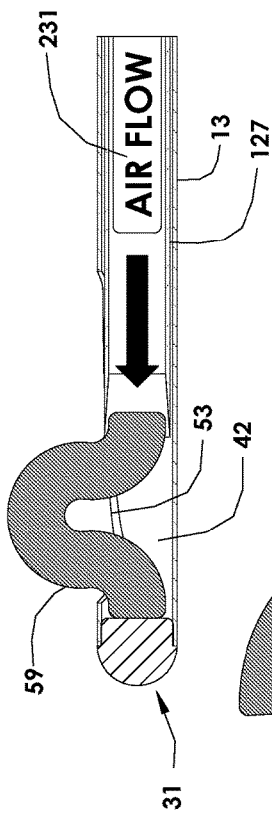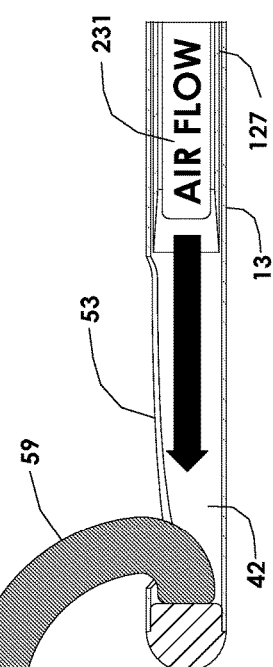
FIG. 60H  FIG. 60I  FIG. 60J  FIG. 60K  FIG. 60L

BIOPSY DEVICE

CROSS REFERENCE TO RELATED APPLICATIONS

This application is a national stage application under 35 U.S.C. §371 of International Application No. PCT/US12/33851, filed on Apr. 16, 2012. The entire disclosure and contents of this application are incorporated herein by reference in their entirety to provide continuity of disclosure.

FIELD

The field relates to surgical instruments and, more specifically, to surgical instruments for performing biopsy procedures.

BACKGROUND

In performing minimally invasive biopsy procedures, it is desirable to reduce the amount of time, trauma and cost associated with the biopsy procedure while simultaneously providing adequate sample tissue to ensure a correct histological assessment. Various biopsy devices have been developed as an alternative to surgery for purposes of implementing minimally invasive biopsy procedures. While suitable for their intended purposes, such biopsy devices have certain limitations.

For example, a persistent limitation of spring-loaded core biopsy devices and vacuum-assisted biopsy devices is that the tissue sample acquired by such devices may be insufficient or inadequate to make a proper histological assessment. Consequently, the physician or other user may be required to acquire an excessive number of tissue samples from the patient, increasing patient trauma and potentially requiring more invasive surgical procedures to acquire the necessary tissue samples.

By way of further example, certain biopsy devices require structure which can make the biopsy devices cumbersome and difficult to manipulate easily. Consequently, such devices may be difficult for the user to properly position within the patient's body. For example, certain vacuum-assisted biopsy devices exist which consist of a motorized hand-held unit tethered by cable and tubing to a control module. The control module supplies electrical power and vacuum to the hand-held unit through the cable and tubing. The cable and tubing can limit freedom of movement of the hand-held unit making it more difficult to position the hand-held unit and attached biopsy probe in proper position for the biopsy procedure. Biopsy devices which require a control module are also expensive and require a substantial capital investment in both training and equipment.

Certain biopsy devices exist which are hand held but do not require a separate control module. However, such biopsy devices include a design which dictates a relatively large and cumbersome biopsy device.

Certain other biopsy devices may function slowly and in a relatively time-consuming manner. For example, certain vacuum-assisted biopsy devices exist which consist of a reusable battery-powered motorized hand-held unit in combination with a disposable probe mounted on the hand-held unit. These types of vacuum-assisted biopsy devices are relatively slow in operation, thereby increasing the time and trauma associated with the biopsy procedure. These types of biopsy devices also tend to be relatively expensive.

Yet other biopsy devices exist which include features enabling the devices to be fully disposable. However, these types of devices can require manual charging with multiple charging strokes. Such multiple strokes can delay the time required for further operational cycles of the biopsy device if multiple tissue samples are to be acquired. These types of biopsy devices include complex parts and are relatively costly for a hand-held disposable product.

There is a need for a biopsy device which would acquire an adequate tissue sample in each use thereby improving the quality of histological assessment, which would minimize the quantity of tissue samples required and reduce the time and trauma associated with the biopsy procedure, which would operate rapidly and positively to acquire the tissue sample in each operational cycle, which could be constructed for ease of manipulation and use enabling better positioning of the biopsy device proximate the tissue to be acquired, which could be disposable thereby reducing risk of infection, which could be constructed in a cost-effective manner to provide an opportunity to control healthcare costs and which would generally improve the quality of patient care.

SUMMARY

Biopsy devices for acquiring a tissue sample together with accessory devices which may be used in conjunction with the biopsy devices are shown and described. The biopsy devices provide the opportunity to positively acquire a meaningful tissue sample, thus improving the quality of care.

One aspect of the present invention is a biopsy device which includes a cannula defining an axis and including a tissue-receiving cavity, a cutter movable along the axis relative to the cannula and the tissue-receiving cavity, a vacuum generating mechanism in air-flow communication with the cannula and tissue-receiving cavity, a first biasing device operating the vacuum generating mechanism to produce a vacuum in the tissue-receiving cavity, and a second biasing device advancing the cutter across the tissue-receiving cavity. It is preferred that the first biasing device operates the vacuum generating mechanism to draw tissue into the tissue-receiving cavity before the second biasing device advances the cutter to cut the tissue. The vacuum generating mechanism includes a vacuum chamber which is preferably concentric with the cutter.

Another aspect of the present invention is a biopsy device including a cannula defining an axis and including a tissue-receiving cavity, a cutter movable along the axis relative to the cannula and tissue-receiving cavity, and a vacuum generating mechanism around at least a portion of the cutter and in air-flow communication with the cannula and tissue-receiving cavity through the cutter to produce a vacuum in the tissue-receiving cavity by drawing air through the cannula and the cutter.

Still another aspect of the present invention is a biopsy device including a housing, a cannula extending from the housing along an axis and having a tissue-receiving aperture, a cutter coaxial with the cannula movable along the axis relative to the cannula, a fixed-position cam coaxial with the cutter and secured with respect to the housing, a rotatable follower coaxial with the cam and movable along the axis, and a cutter carrier movably secured with respect to the housing and supporting the rotatable follower along the axis such that movement of the cutter carrier toward the tissue-receiving aperture simultaneously rotates the cutter about the axis and moves the cutter along the axis across the tissue-receiving aperture to cut tissue when the tissue is received in the tissue-receiving aperture. The cam preferably has a spiral cam track disposed about the axis. It is preferred that the cutter extend from the follower along the axis and that the follower ride the spiral cam track such that the follower and the cutter rotate about the axis when the follower moves along the axis.

Another aspect of the present invention is a biopsy device configured for a subcutaneous tissue acquisition. Such inventive biopsy device includes a housing, a cannula extending from the housing and defining a tissue-receiving aperture, and a tissue cutting mechanism including a cutter coaxial with the cannula and movable along the axis relative to the cannula between an advanced position and a retracted position partially obstructing the tissue-receiving aperture. The tissue cutting mechanism preferably includes a biasing device moving the cutter toward the advanced position. The tissue cutting mechanism further preferably includes at least one releaseable stop which retains movement of the cutter in the retracted position partially obstructing the tissue-receiving aperture.

Some embodiments of the inventive biopsy device include a purge valve which automatically purges the vacuum once the cutter advances across the tissue-receiving cavity. In such embodiments, the cutter is a cutter cannula in air-flow communication with the tissue-receiving cavity and includes at least one air-flow port within a vacuum chamber during production of the vacuum. The purge valve operates between a closed position during the vacuum production and an open position allowing ambient air flow through the cutter cannula to purge the vacuum in the tissue-receiving cavity, preferably once the cutter advances across the tissue-receiving cavity. The purge valve preferably includes a seal concentric with the cutter cannula. The seal preferably moves with the cutter cannula along the axis. The purge valve further preferably includes an elongate member which is concentric with the cutter cannula and has a configuration which, when in alignment with the seal, allows the ambient air flow into the cutter cannula, preferably between the seal and the configuration.

Still another aspect of the present invention is a biopsy device in which the vacuum about an outer surface of the biopsy device at the tissue-receiving cavity can be purged to facilitate withdrawal of the biopsy device from a patient with a tissue sample therein. In such embodiments, the cannula is an outer cannula which includes the tissue-receiving cavity and the cutter cannula is within the outer cannula. In the open position of the purge valve, the at least one port of the cutter cannula allows ambient air flow into the outer cannula to purge the vacuum about the outer cannula at the tissue-receiving cavity. In an aspect, the cutter cannula may have an inscribed cutting edge.

Another aspect of the present invention is a biopsy device with a vacuum generating mechanism operable to force air from the vacuum chamber toward the tissue-receiving cavity to eject the tissue sample therefrom. In such biopsy device embodiment, the cutter cannula moves between advanced and retracted positions. In the retracted position, the purge valve is in a closed position with the air filled vacuum chamber in air-flow communication with the tissue-receiving cavity. During tissue ejection, air from the vacuum chamber can be forced into and through the cutter cannula and into the tissue-receiving cavity to eject the tissue therefrom before the cutter cannula is fully retracted and withdrawn from the tissue-receiving cavity thereby improving ejection of the tissue sample from the tissue-receiving cavity. The biopsy device of this type further preferably includes a delay mechanism interrupting retraction of the cutter cannula providing a further opportunity to force air from the vacuum chamber before complete retraction of the cutter cannula.

Yet another aspect of the present invention is a cannula for a biopsy device, the cannula including a tube having a closed end and an opposite open end. The inventive cannula includes a lateral tissue-receiving aperture through the tube adjacent the closed end, the tissue-receiving aperture narrowing in a direction away from the closed end. The tissue-receiving aperture preferably extends between first and second curved end edges, the first end edge being adjacent the closed end of the tube. It is preferred that the first end edge have a radius which is greater than a radius of the second end edge.

Still another aspect of the present invention is an introducer for making a tunneling opening in tissue so that a biopsy device cannula can be inserted into the opening after removal of the introducer. The inventive introducer includes a handle and a lance extending outward from the handle and defining an axis. The lance includes a shank extending outward from the handle and a sharp tip element extending outward from the shank. It is preferred that the lance have a length dimension identical to a length dimension of the biopsy device cannula used with the introducer. The sharp tip element preferably includes a locator region which has a length dimension identical to a length dimension of a tissue-receiving aperture of the cannula of the biopsy device such that the tissue-receiving aperture can be located at a position in the tissue identical to that of the locator region.

Another aspect of the present invention is a depth guide system for indicating a depth of insertion of a biopsy device into tissue. The inventive system includes a depth guide usable with a depth guide indicator. The depth guide includes first and second open ends, an outer surface including a depth scale and a tubular body having an inner surface defining a passageway for receiving a biopsy device cannula. Exemplary depth guide indicator includes a one-piece body. The one-piece body has a spreadable clamp portion defining a gripping aperture, an internal spring portion providing a clamping force to the clamp, and opposed spreader portions providing a force which spreads the clamp to receive the depth guide in the gripping aperture. It is preferred that the one-piece body further includes facing stop portions which limit spreading of the clamp portions. The depth guide indicator may be provided separate and apart from the depth guide.

BRIEF DESCRIPTION OF THE DRAWINGS

Exemplary biopsy devices may be understood by reference to the following description taken in conjunction with the accompanying drawings, in which like reference numerals identify like elements throughout the different views. For convenience and brevity, like reference numbers are used for like parts amongst the embodiments. The drawings are not necessarily to scale, emphasis instead being placed upon illustrating the principles of the invention. In the accompanying drawings:

FIG. 3 is a right side elevation view of the biopsy device of FIG. 1;

FIG. 4 is a right side elevation view of the biopsy device of FIG. 1, but in a fully charged state;

FIG. 6 is a top side plan view of the biopsy device of FIG. 1;

FIG. 7 is a top side plan view of the biopsy device of FIG. 1, but in a fully charged state;

FIG. 8 is a bottom side plan view of the biopsy device of FIG. 1, but in a fully charged state;

FIG. 9 is a front elevation view of the biopsy device of FIG. 1;

FIG. 10 is a rear elevation view of the biopsy device of FIG. 1;

FIG. 12 is a right side elevation view of the biopsy device of FIG. 11;

FIG. 13 is a left side elevation view of the biopsy device of FIG. 11;

FIG. 20 is top plan view of the exemplary cannula, cannula support and vacuum chamber subassemblies including an exemplary tissue-receiving aperture;

FIG. 20A is an enlarged view of the exemplary tissue-receiving aperture taken along section 20A of FIG. 20;

FIG. 21 is plan view of an exemplary cutter apart from the follower;

FIG. 21A is a section view of the cutter taken along section 21A-21A of FIG. 21;

FIG. 21B is an enlarged view of an exemplary cutter inscribed edge taken along section 21B of FIG. 21A;

FIG. 22 is a section view taken along section line 22-22 of FIG. 4;

FIG. 23 is a section view taken along section line 23-23 of FIG. 7;

FIG. 23A is an enlarged view of actuator mechanism components taken along section 23A of FIG. 23;

FIG. 24 is a fragmentary section view taken along section line 23-23 of FIG. 7, with certain parts removed to facilitate understanding;

FIG. 24A is an enlarged view of exemplary vacuum generating mechanism components taken along section 24A of FIG. 24;

FIG. 24B is an enlarged view of an exemplary purge valve in a closed position taken along section 24B of FIG. 24;

FIG. 25 is a perspective view of the biopsy device of FIG. 1 in a fully charged state with certain parts cut away and others removed to facilitate understanding;

FIG. 25A is an enlarged view taken along section 25A of FIG. 25;

FIG. 26 is a section view taken along section line 22-22 of FIG. 4, but showing the biopsy device in a partially discharged state;

FIG. 26A is an enlarged view of an exemplary sear and cutter carrier in a partially discharged state of the biopsy device taken along section 26A of FIG. 26;

FIG. 27 is a section view taken along section line 23-23 of FIG. 7, but showing the biopsy device in a partially discharged state;

FIG. 28 is a fragmentary section view taken along section line 23-23 of FIG. 7 including arrows to show air flow direction and with certain parts removed to facilitate understanding;

FIG. 28A is an enlarged view of exemplary vacuum generating mechanism components including arrows to show air flow direction taken along section 28A of FIG. 28;

FIG. 28B is an enlarged view of the exemplary purge valve including an arrow to show air flow direction taken along section 28B of FIG. 28;

FIG. 32 is a section view taken along section line 32-32 of FIG. 3;

FIG. 32A is an enlarged view of the exemplary sear and cutter carrier in a fully discharged state of the biopsy device taken along section 32A of FIG. 32;

FIG. 33 is a section view taken along section line 33-33 of FIG. 6;

FIG. 34 is a fragmentary section view taken along section line 33-33 of FIG. 6 including arrows to show air flow direction and with certain parts removed to facilitate understanding;

FIG. 34A is an enlarged view of exemplary ports including arrows to show air flow direction taken along section 34A of FIG. 34;

FIG. 34B is an enlarged view of the exemplary purge valve including arrows to show air flow direction taken along section 34B of FIG. 34;

FIG. 37 is a section view taken along section line 32-32 of FIG. 3, but during biopsy device charging and tissue sample ejection;

FIG. 38 is a section view taken along section line 33-33 of FIG. 6, but during biopsy device charging and tissue sample ejection;

FIG. 38A is an enlarged view of an exemplary tissue-receiving cavity and tissue sample being ejected therefrom taken along section 38A of FIG. 38;

FIG. 39 is a fragmentary top plan view with certain parts in section taken along section line 32-32 of FIG. 3 including arrows to show air flow direction, but during biopsy device charging and tissue sample ejection and with certain parts removed to facilitate understanding;

FIG. 39A is an enlarged view of exemplary vacuum generating mechanism components including arrows to show air flow direction taken along section 39A of FIG. 39;

FIG. 39B is an enlarged view of the exemplary purge valve including an arrow to show air flow direction taken along section 39B of FIG. 39;

FIG. 41 is a section view taken along section line 41-41 of FIG. 39 showing further delay mechanism components;

FIG. 42 is a section view showing a further exemplary biopsy device which may be used for subcutaneous biopsy procedures, in a fully charged state and taken along a section such as section line 22-22 of FIG. 4;

FIG. 42A is an enlarged view of an exemplary sear and cutter carrier in a fully charged state of the biopsy device taken along section 42A of FIG. 42;

FIG. 43 is a section view of the biopsy device of FIG. 42 taken along a section such as section line 23-23 of FIG. 7, in a fully charged state;

FIGS. 44A-44D are front elevation views of an exemplary tissue-receiving aperture, cannula and cannula support at four different positions;

FIG. 50 is a perspective view of an exemplary depth guide indicator;

FIG. 51 is a plan view of the exemplary depth guide indicator of FIG. 50;

FIG. 54 is a schematic illustration of the biopsy device of FIG. 1 including an optional depth guide before insertion into tissue, which is shown as breast tissue;

FIG. 55 is a schematic illustration of the biopsy device of FIG. 1 including the optional depth guide, after insertion into the tissue;

FIGS. 60H-60L are schematic illustrations showing the exemplary biopsy device of FIG. 11 during tissue sample ejection.

DETAILED DESCRIPTION

Figure 1:
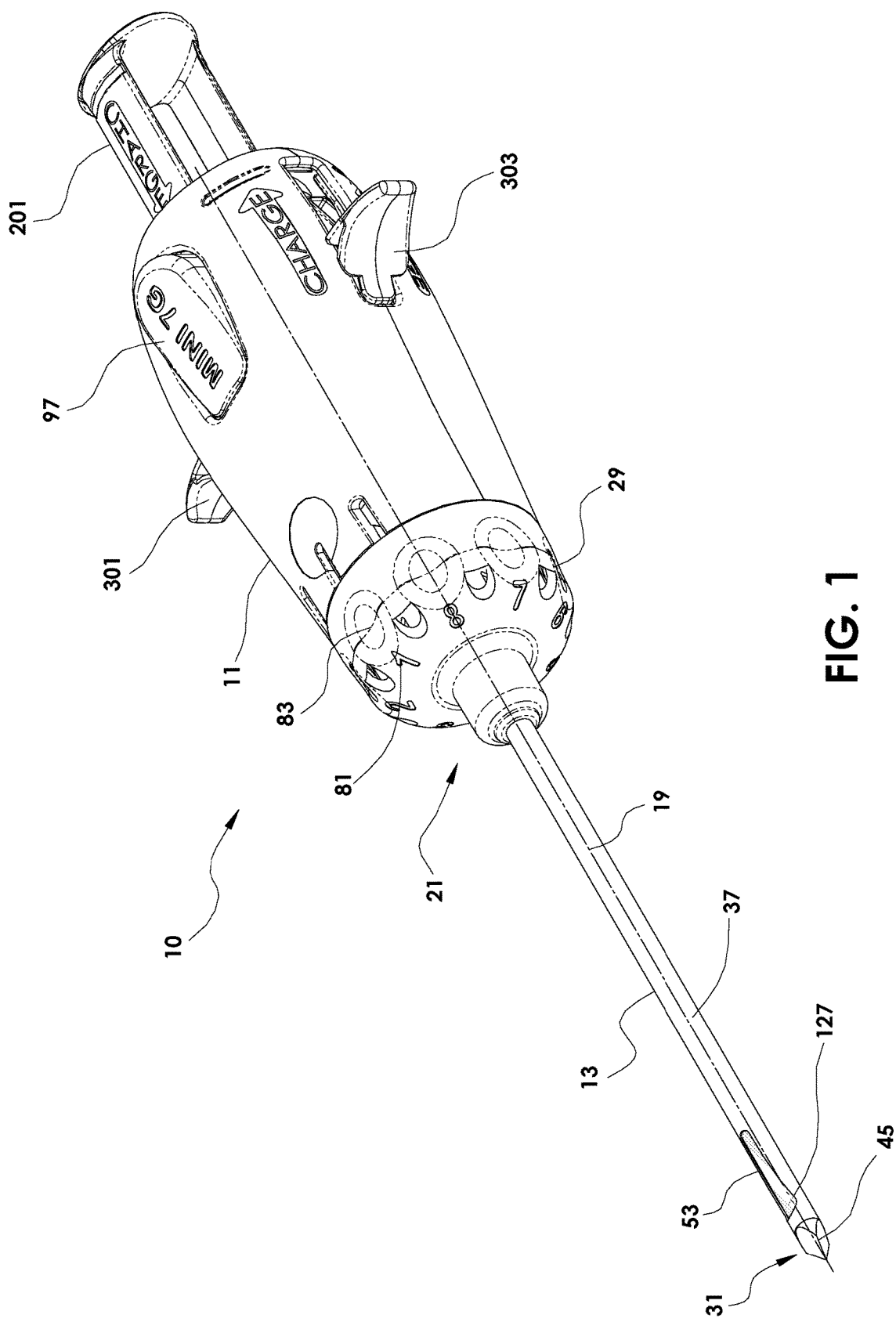
FIG. 1 is a front side perspective view of an exemplary biopsy device in a fully discharged state.

FIGS. 1-15 illustrate first and second exemplary biopsy device embodiments 10, 10' in accordance with the invention. FIGS. 1-10 illustrate exemplary biopsy device 10 and FIGS. 11-15 illustrate exemplary biopsy device 10'. Exemplary biopsy devices 10, 10' are preferably suitable for use in biopsy procedures wherein a tissue sample is acquired, collected, or taken, from surrounding tissue. Exemplary biopsy devices 10, 10' share the same structure and operation, except as noted herein. For convenience and brevity, common reference numbers are used to identify like parts and features of biopsy devices 10, 10'. While preferred biopsy device embodiments 10, 10' described and shown herein are self-contained hand-held devices, persons of skill in the art will appreciate that such embodiments are exemplary only and that the principles described herein can have application in other biopsy device embodiments.

In general, exemplary biopsy devices 10, 10' comprise a housing 11, a cannula 13, a tissue cutting mechanism 15 and a vacuum generating mechanism 17. Cannula 13 defines a longitudinal axis 19 which extends through housing 11 and, in the embodiments is an outer cannula for the reasons described below. In the embodiments, cannula 13, tissue cutting mechanism 15 and vacuum generating mechanism 17 are all preferably coaxial with axis 19. "Coaxial" means or refers to having or being mounted on the same axis. Coaxial parts may also be concentric to one another. "Concentric" means or refers to having a common axis. Such coaxial positioning and arrangement of such parts 13, 15 and 17 with the potential for concentric part relationships is referred to herein as "centerline construction." Centerline construction provides the opportunity for embodiments of the invention, such as exemplary biopsy devices 10, 10', to be compact, held in a single hand and to be entirely self contained. Compactness may be provided by arranging parts around each other along the common axis, rather than one after the other, thus decreasing the axial length required by the biopsy device 10, 10'. In effect, biopsy device embodiments may be designed for compactness with parts nested within other parts to conserve space.

These and other attributes permit embodiments of biopsy devices 10, 10' to be positioned easily by the physician or other user, hereinafter simply "user", to reliably acquire a tissue sample, resulting in a better quality of patient care. For example, biopsy devices 10, 10' can be implemented as self-contained, lightweight devices capable of being held in a single hand of a user without necessity for connection by cables and tubing to a remote module. In such embodiments, the biopsy devices 10, 10' would be easy to hold and manipulate by a user, permitting the biopsy devices 10, 10' to be more accurately positioned in the patient for tissue acquisition. Centerline construction further provides an opportunity to implement a biopsy device 10, 10' with fewer and less complex parts, thereby providing both a more robust product and a cost advantage as compared to other biopsy devices, again providing an opportunity for a better quality of patient care. Biopsy devices 10, 10' may be provided as single use devices which can be discarded after use because of the opportunity to control cost of manufacture.

Referring again to FIGS. 1-15, exemplary housing 11 comprises a front end 21 and a rear end 23. From the user's perspective, front end 21 of biopsy devices 10, 10' represents a distal end because such end is the end furthest from the user during use while rear end 23 represents a proximal end because such end is closest to the user during use.

Housing 11 is enclosed by first and second covers 25, 27 and by cannula support 29. Cannula 13 extends from housing 11 supported by cannula support 29 coaxial with axis 19. In the examples and as illustrated in FIGS. 44A-44D, cannula support 29 and cannula 13 supported thereby may be rotatable about axis 19 for the reasons described below.

As illustrated in the examples of FIGS. 1-15, exemplary housing 11 and exemplary covers 25, 27 and cannula support 29 of housing 11 may be symmetrical about axis 19 side to side and top to bottom. Such symmetry provides an opportunity for both an elegant design and cost savings through the use of identical covers 25, 27 and certain internal parts in construction of biopsy devices 10, 10'.

For hand-held embodiments and as illustrated in FIGS. 1-2, 6-9, 11 and 14-15, housing 11 may optionally include a taper, narrowing from rear end 23 proximal the user toward front end 21 distal from the user. Biopsy devices 10, 10' are preferably held by a user's hand toward rear end 23 and a slightly wider rear end 23 may be more ergonomic and comfortable for certain users.

Exemplary Cannula Portion

As shown for example in FIGS. 1-17, 20-21B, 22, 24, 25, 25A, 26 and 30, cannula 13 may be a cylindrical tube which extends from housing 11 to a closed distal end 31 furthest from housing 11. Cannula 13 may further include an open proximal end 33 secured to a neck 35 of cannula support 29 (FIG. 25A). Exemplary cannula 13 includes an outer surface 37 and an inner surface 39 which defines a hollow lumen 41 between distal and proximal ends 31, 33 as can be seen for example in FIG. 30.

Referring to FIGS. 24A, 25A, 28A, 34A and 39A, cannula 13 proximal end 33 may be secured to cannula support 29 neck 35 by means of an over-molding plastic injection molding process during manufacture of cannula support 29. In such over-molding process, plastic flows into the mold cavity and into one or more circumferential openings in cannula 13 (e.g., opening 43) to secure cannula 13 and cannula support 29 together with cannula 13 proximal end 33 closer to housing 11 rear end 23 and cannula 13 extending away from neck 35 and housing front 11 end 21 along axis 19. The over-molding process forms an air-tight barrier between neck 35 and cannula 13 outer surface 37 allowing air to pass through cannula support 29 only through cannula lumen 41 for the reasons described below.

Referring to FIGS. 1-10, 16-17, 20 and 52-55 and biopsy device 10, exemplary cannula distal end 31 terminates in a sharp end tip element 45, which may be a trocar-type end element as illustrated or another type of end element capable of self-tunneling of cannula 13 into tissue 47. The sharp end tip element 45 is a self-tunneling end which may be inserted directly into tissue 47 (e.g., breast or other tissue) without first making a tunnel 49 (FIG. 58) with an introducer, such as the exemplary introducers 51, 51' illustrated in FIGS. 45-49. Biopsy device 10 would be compatible with biopsy procedures in which biopsy device 10 is guided within tissue 47 by visualization techniques such as x-ray imaging and ultrasound imaging, to position the biopsy device 10 within tissue 47 proximate the lesion, tumor or other targeted tissue 48 to be acquired. Biopsy device 10 could also be used with magnetic resonance imaging (MRI) visualization procedures if constructed with materials which are not attracted to a magnet of the type utilized in MRI procedures.

Referring to FIGS. 11-15, and 58-60L, exemplary cannula distal end 31 of biopsy device 10' terminates in a blunt end tip element 45', which may be hemispherical as illustrated. Blunt end tip element 45' may be used in conjunction with a sharp tipped introducer, such as exemplary introducers 51 or 51'. Introducers 51, 51' produce a tunnel 49 (FIG. 58) in the tissue 47 into which cannula 13 is inserted after removal of introducer 51 or 51' to position tissue-receiving aperture 53 proximate the lesion, tumor or other targeted tissue 48 to be acquired as described below.

Introducers 51, 52 may be made of materials not attracted to a magnet permitting introducers 51, 52 to be guided within tissue 47 by visualization techniques such as MRI as well as x-ray imaging and ultrasound imaging. The biopsy device 10' can then be positioned without MRI within the tissue 47 at the position of the introducer 51, 51' as described below. It is further anticipated that biopsy devices 10, 10' may be used as stand alone devices without visualization, as well as with types of visualization other than x-ray imaging, ultrasound imaging and MRI, particularly as technology advances in the future.

Each tip element 45, 45' is preferably press fit and welded into distalmost end of cannula 13 during manufacture to close cannula 13 distal end 31, but may be provided in other ways. Other than the type of tip element 45, 45' biopsy devices 10, 10' are identical in structure and operation.

Tissue-receiving aperture 53 is provided through cannula 13 and cannula outer and inner surfaces 37, 39 (FIG. 24A) in a side of cannula 13 proximal from, or adjacent to, distal end 31. In the biopsy device embodiments 10, 10', exemplary tissue-receiving aperture 53 comprises a lateral aperture in cannula 13 because of the position of such aperture in the side of cannula 13. Tissue-receiving aperture 53 opens into lumen 41. Tissue-receiving aperture 53 and lumen 41 form a tissue-receiving cavity 42 within cannula 13 into which tissue 47 is drawn by a vacuum produced by vacuum generating mechanism 17 for cutting, severing, shearing and tissue sample 59 acquisition as described herein.

FIG. 20A is an enlarged view of an embodiment of a tissue-receiving aperture 53. Exemplary tissue-receiving aperture 53 of FIG. 20A has a widened distal end 55 which narrows, or tapers, in a direction away from closed distal end 31, through a medial portion 56 and toward a narrowed proximal end 57. Distal and proximal ends 55, 57 of tissue-receiving aperture 53 may include a radius as illustrated. In the embodiment, widened distal end 55 and narrowed proximal end 57 include curved end edges. Also in the embodiments, widened distal end 55 edge has a radius which is greater than a radius of the narrowed proximal end 57 edge.

Widened distal end 55 is representative of a cylindrical port with an axis transverse to axis 19 and a diameter approximately the same size as the inside diameter of cannula 13 lumen 41. Narrowed distal end 57 is representative of a second cylindrical port also with an axis transverse to axis 19 and a diameter approximately less than the inside diameter of the cannula 13 lumen 41. Both cylinders are joined together with a medial portion 56 that is tangential to the distal and proximal ports, resulting in a tapered opening that is wider at the distal end 55 and narrower at the proximal end 57.

The architecture of exemplary tissue-receiving aperture 53 is believed to provide for acquisition of a more substantial and uniform tissue sample 59. Without wishing to be bound by any particular theory, it is believed that the widened distal end 55, which is relatively larger than the narrowed distal end 57, provides less resistance to entry of tissue 47 through tissue-receiving aperture 53 and into the tissue-receiving cavity 42 preferentially toward widened distal end 55 as illustrated schematically in FIGS. 60B-60C. As illustrated schematically in FIGS. 60A-60L, preferential entry of tissue 47 into distal end 55 of tissue-receiving aperture 53 before entry of tissue 47 entry into proximal end 57 of tissue-receiving aperture 53 is believed to avoid blockage of lumen 41 before tissue 47 is fully received into tissue-receiving cavity 42, thereby avoiding potential loss of vacuum produced by vacuum generating mechanism 17 proximate tissue-receiving aperture 53 and within tissue-receiving cavity 42. As a result, a more substantial tissue sample 59 may be acquired reducing the number of tissue samples 59 required. Persons of ordinary skill in the art will appreciate that tissue-receiving aperture 53 may have configurations other than that illustrated in FIG. 20A.

Exemplary Housing Portion

Figure 19:
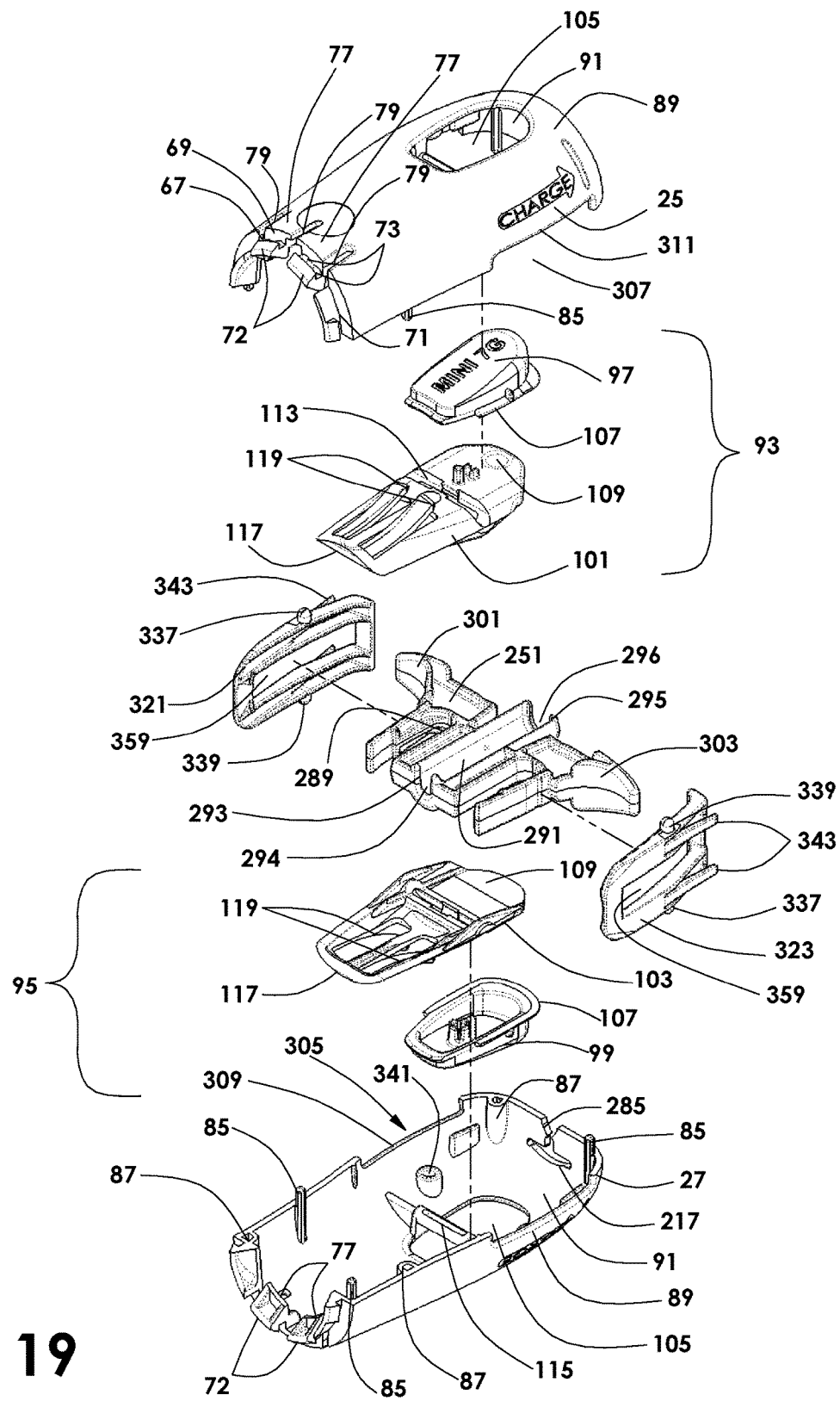
FIG. 19 is an exploded view of exemplary housing, actuator and cutter carrier subassemblies and related components for use in the biopsy device of FIG. 1.

Referring next to FIGS. 1-9, 11-17, 19, 22-24A and 44A-44D, exemplary cannula support 29 of housing 11 partially encloses the internal components of biopsy device 10, 10' and is coaxial with axis 19 and concentric with cannula 13. Cannula support 29 may include a generally convex outer side 61 which includes neck 35 and a concave inner side 63 which defines a cavity 64 within neck 35 (FIG. 24A). Cannula support 29 is preferably rotatably attached to housing 11 by means of pins 65 (FIGS. 22, 23 and 24) which extend radially inward from cannula support 29 inner side 63 and are seated between walls 67, 69 defining an annular groove 71 formed by joined-together covers 25, 27 (FIG. 19). Inclined walls 72 deflect slightly when abutted by pins 65 during assembly permitting cannula support 29 to be snap fit onto covers 25, 27. Pins 65 and walls 67, 69 limit axial movement of cannula support 29 while pins 65 and groove 71 permit cannula support 29 to rotate clockwise or counterclockwise (FIGS. 44A-44D).

Referring to FIGS. 19 and 44A-44D, exemplary cannula support 29 may be indexed between defined rotational positions relative to housing 11 by rotation of cannula support 29 so that a pin 65 is seated snugly between spaced-apart radially outward projecting ribs 73 in annular groove 71. In the examples, a pair of ribs 73 are provided on each deflectable cover portion 77 of covers 25, 27 facing cannula support 29 inner side 63. (Cover 27 includes ribs 73 identical to the pairs of ribs 73 illustrated on cover 25 in FIG. 19.) Each deflectable cover portion 77 is defined by a slot 79 in cover 25, 27. Slots 79 permit each deflectable cover portion to bend slightly inward so that a pin 65 can ride over a pair of the ribs 73 as cannula support 29 is rotated.

FIGS. 44A-44D show cannula support 29 and cannula 13 at four of eight indexed positions as indicated by the different position of tissue-receiving aperture 53 in each of FIGS. 44A-44D. In the examples, cannula support 29 is rotated to the desired position with a user's fingers while the user simultaneously holds covers 25, 27 of housing 11 in a constant position.

Referring for example to FIGS. 1, 11 and 44A-44D, indicia 81, such as numbers, may be provided on cannula support 29 outer side 61 to indicate each indexed position of cannula support 29 so that tissue-receiving aperture 53 can be rotated 360° and so that multiple tissue samples (e.g., tissue sample 59) can be taken from a single location within tunnel 49.

Figure 11:
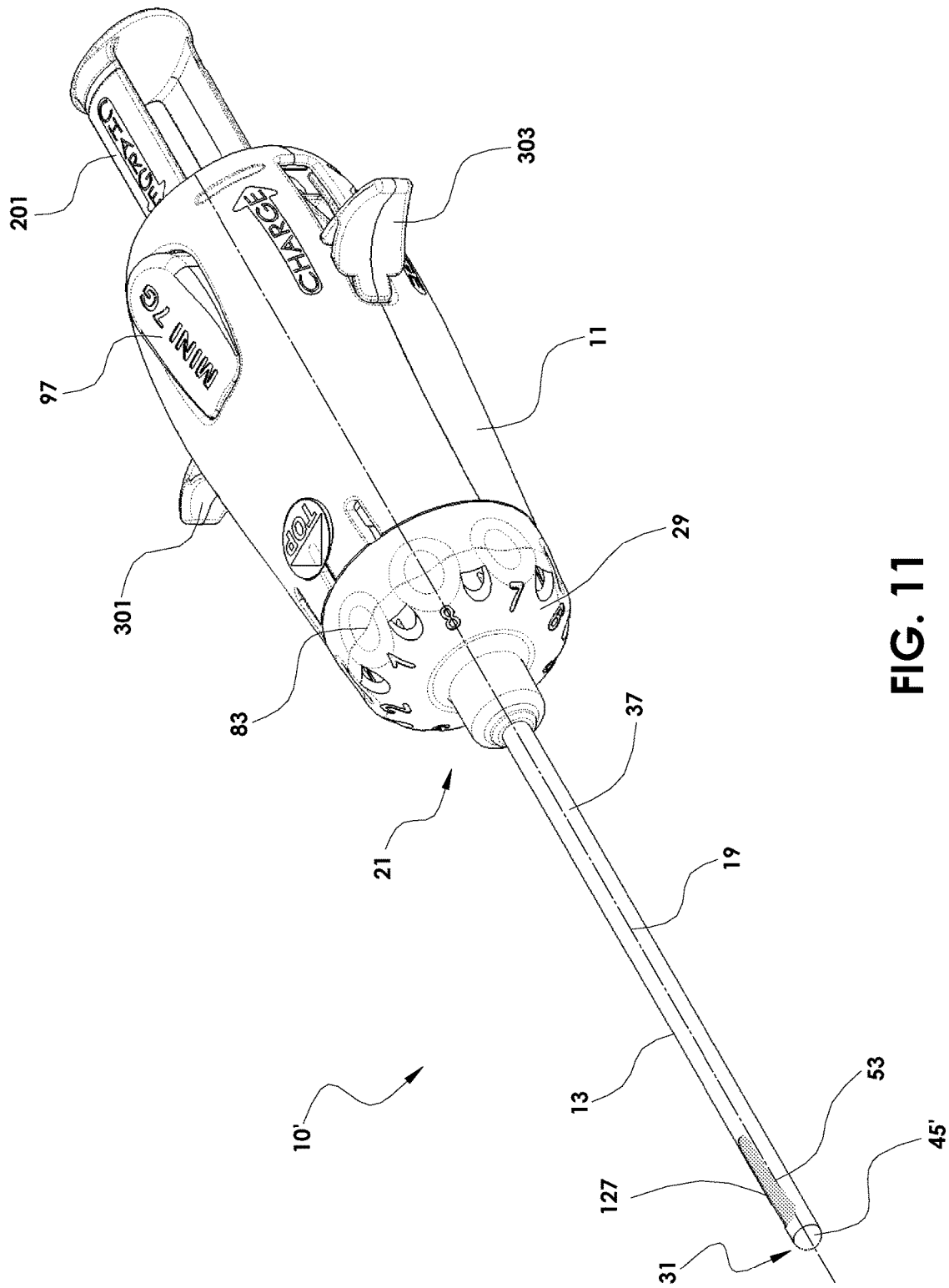
FIG. 11 is a front side perspective view of a further exemplary biopsy device, shown in a fully discharged state.
Figure 14:
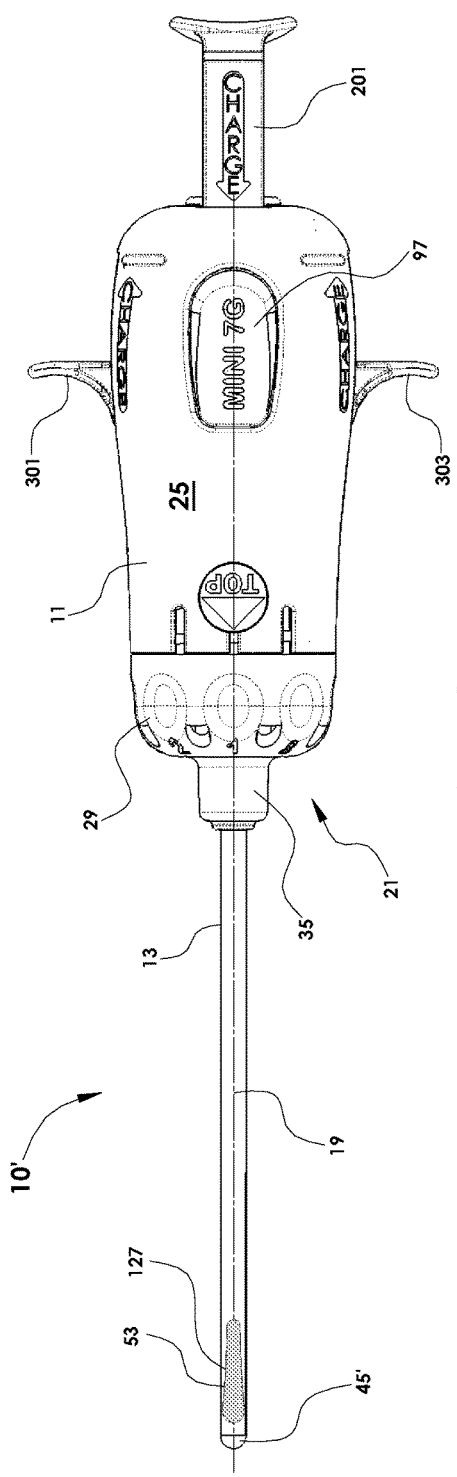
FIG. 14 is a top side plan view of the biopsy device of FIG. 11.
Figure 15:
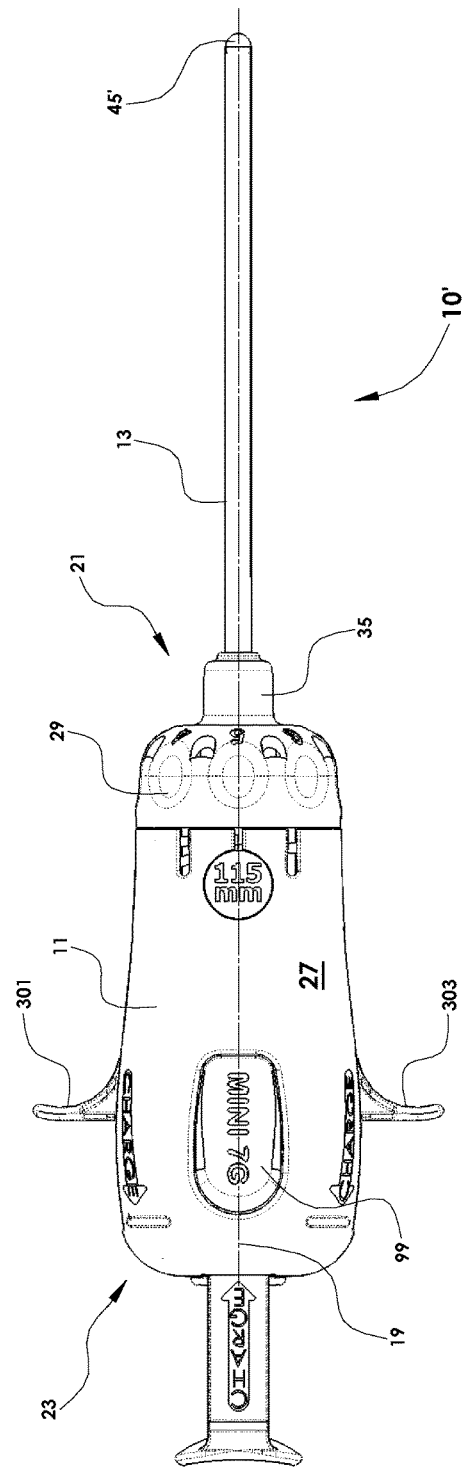
FIG. 15 is a bottom side plan view of the biopsy device of FIG. 11.
Figure 17:
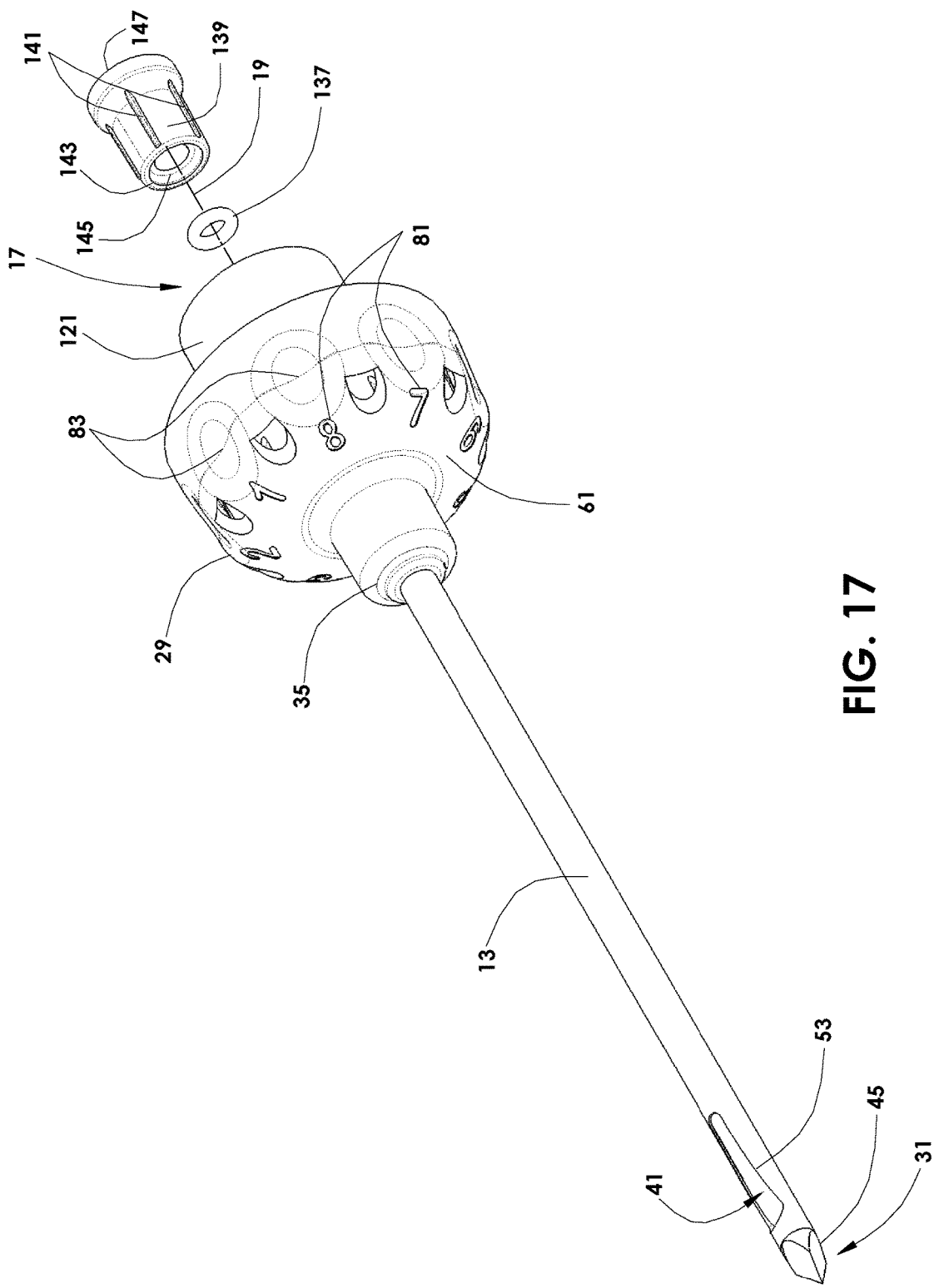
FIG. 17 is an exploded view of an exemplary cannula, cannula support and vacuum chamber subassembly for use in the biopsy device of FIG. 1.
Figure 18:
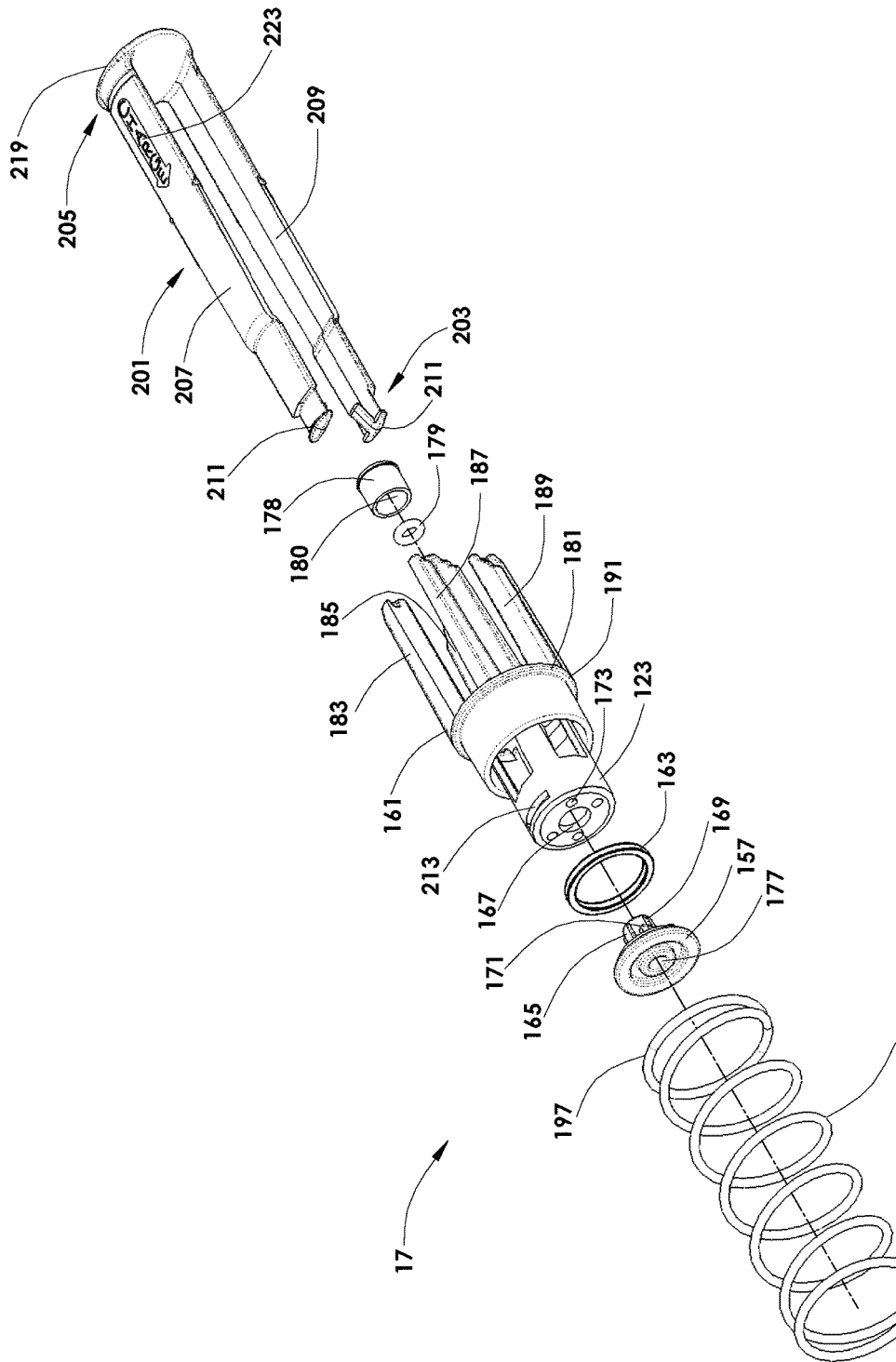
FIG. 18 is an exploded view of an exemplary piston subassembly and related components for use in the biopsy device of FIG. 1.

Also as illustrated in FIGS. 1, 11 and 17, a plurality of grips 83 may be provided around cannula support 29 for gripping with a user's fingers. In the examples, grips 83 are concave and are concentric with axis 19. The grips 83 permit the user to more firmly grip cannula support 29 with the user's hand so that cannula support 29 can be rotated relative to housing 11 to position tissue-receiving aperture 53 at one of the indexed positions.

Referring now to FIGS. 1-16 and 19, covers 25, 27, further enclose the internal components of each biopsy device 10, 10'. Covers 25, 27 are pressed together with alignment posts 85 seated in a corresponding alignment boss 87 (FIG. 19). Referring further to FIG. 19, each alignment post 85 preferably includes external crush ribs (not shown) that create an interference fit when received in the corresponding female alignment boss 87 to join the covers 25, 27 together. Each cover 25, 27 has an outer surface 89 and an inner surface 91. In the examples, covers 25, 27 are identical, thereby providing simplicity and an opportunity for cost reduction.

As illustrated in FIG. 19, a pair of trigger mechanisms 93, 95 are associated with each cover 25, 27 to trigger operation of biopsy device 10, 10.' Trigger mechanisms 93, 95 each serve as an actuator for triggering operation of vacuum generating mechanism 17 and biopsy devices 10, 10' generally. Exemplary trigger mechanisms 93, 95 are mirror images of each other and utilize identical parts providing an opportunity to reduce cost. Each trigger mechanism 93, 95 is actuated when pressed inward by a user's fingers toward a respective cover 25, 27. Two trigger mechanisms 93, 95 are provided as a safety feature. Both trigger mechanisms 93, 95 must be actuated (simultaneously or sequentially) to trigger operation of each biopsy device 10, 10'. The two trigger mechanism 93, 95 architecture prevents inadvertent operation of a biopsy device 10, 10'. A single trigger mechanism could be implemented.

Referring for example to FIGS. 1-16, 19, 23, 23A, 27, 33, 38 and 43, each exemplary trigger mechanism 93, 95 comprises a trigger button 97, 99 and a corresponding sear 101, 103. Each trigger button 97, 99 is identical and protrudes outward from a cover 25, 27 (e.g., FIGS. 3, 12) through a complementary opening 105 in cover 25, 27. A flange 107 on each trigger button 97, 99 contacts an inner surface 91 of a respective cover 25, 27 to limit outward movement of trigger buttons 97, 99.

Sears 101, 103 are each a pivoted part that holds a biopsy device 10, 10' in a charged state before operation. Each sear 101, 103 pivots when sear proximal end 109 is pressed by movement of a respective trigger button 97, 99 (FIGS. 23A, 27). Each sear 101, 103 proximal end 109 pivots inwardly and each distal end 117 pivots outwardly. FIG. 23A illustrates inward movement of sear 101 proximal end 109 in the direction of arrow 111. Sear 103 proximal end 109 moves inward in the same manner.

In the embodiments of FIGS. 16, 19, 23A and 27, each sear 101, 103 is identical and has an elongate slot 113 which is snap fit into an elongate pivot 115 which extends inwardly from a cover 25, 27 inner surface 91 to permit sears 101, 103 to pivot back and forth on a respective pivot 115. Sear 101, 103 distal ends 117 are biased inward by integral springs 119 which extend toward and contact a respective cover inner surface 91 to bias sear distal end 117 inward to hold a biopsy device 10, 10' in its charged state before operation as described below.

Exemplary Vacuum Generating Mechanism

Referring to FIGS. 16-18, 24-24B, 28-28B, 34-34B and 39-39B, exemplary vacuum generating mechanism 17 capable of use in biopsy devices 10, 10' comprises vacuum chamber 121, piston 123, spring 125, cutter 127, purge valve 129 and related components as described herein. In the examples, spring 125 comprises a first biasing device, the purpose of which is to bias piston 123 to create a vacuum, or negative air pressure, and to operate vacuum generating mechanism 17, preferably in a sequence before operation of tissue cutting mechanism 15 begins as described herein. The term "vacuum" as used herein refers to a negative air pressure. A vacuum is not required to be a complete vacuum and may comprise a partial vacuum in which, for example, vacuum chamber 121, cannula 13 lumen 41 or cutter 127 lumen 283 are partly exhausted of air.

Exemplary vacuum generating mechanism 17 serves as a type of pump capable of generating a vacuum and, alternatively, generating a positive air pressure at tissue-receiving aperture 53 and tissue-receiving cavity 42. The vacuum draws tissue 47 into tissue-receiving cavity 42 for tissue cutting, severing and shearing (FIGS. 22-36 and 60A-60G). Alternatively, the positive air pressure ejects the tissue sample 59 from tissue-receiving cavity 42 (FIGS. 37-40 and 60H-60L) after the tissue sample 59 has been acquired. Exemplary vacuum chamber 121, piston 123, spring 125, cutter 127, purge valve 129 and related components may be coaxial with axis 19 according to the preferred centerline construction of biopsy devices 10, 10'.

As shown in FIGS. 16-17, 20, 22, 24A, 27-28A, 32, 33 and 34, vacuum chamber 121 may be an integral part of cannula support 29. In the examples, vacuum chamber 121 is coaxial with axis 19 and concentric with cutter 127 because vacuum chamber 121 is around a portion of cutter 127. In the examples, indexing of cannula support 29 to position tissue-receiving aperture 53 at different radial positions about axis 19 would also rotate vacuum chamber 121. Vacuum chamber 121 is preferably defined by a cylindrical wall 131 (FIG. 24A) which has an open first end 133 (FIG. 22) facing housing 11 rear end 23 which is open to receive piston 123 within vacuum chamber 121. Piston 123 within vacuum chamber 121 is also concentric with cutter 127 and cutter 127 passes through piston 123. The concentric relationship of vacuum chamber 121, piston 123 and cutter 127 provides an opportunity for a more compact biopsy device 10, 10' with a minimized axial length because arrangement of vacuum chamber 121 around piston 123 and piston around cutter 127 can reduce axial length compared with arrangements in which such parts would be positioned one after the other.

Referring to FIGS. 24A and 28A, vacuum chamber 121 has a second end 135 (FIG. 28A) toward housing 11 front end 21 which is sealed where cannula 13 extends from cannula support 29 as previously described.

As shown in FIGS. 16-17, 24A and 28A, annular seal 137, forms an air-tight seal against cutter 127 sealing vacuum chamber 121 during vacuum generation and during generation of the positive pressure to eject tissue sample 59 (FIGS. 37-40). Annular seal 137 may be a resilient sealing O-ring, a rubber washer or some other material. Seal 137 is seated in a seal retainer 139. Exemplary annular seal 137 and seal retainer 139 are coaxial with axis 19 and are concentric with cutter 127.

Exemplary seal retainer 139 is preferably a generally cylindrically-shaped member and is received in the cavity 64 (FIG. 24A) defined by inner side 63 of cannula support 29 neck 35. Seal retainer 139 may have radial outward longitudinal ribs 141 (FIG. 17) tapered toward seal retainer distal end 143 to facilitate a tight frictional press fit against inner side 63 of cannula support 29 neck 35 within cavity 64. Seal retainer 139 distal end 143 abuts cannula support inner side 63 and includes an annular seat 145 in which annular seal 137 is retained. Seal retainer 139 further includes a proximal end 147 and an inner cylindrical wall 149 defining a cylindrical passageway 151 between the distal and proximal ends 143, 147 through which cutter 127 extends along axis 19. Seal retainer 139 proximal end 147 further includes annular seat 155 for receiving piston face 157.

As illustrated in FIGS. 16, 24A, 28A and 30, seal retainer 139 tightly seated in cavity 64 presses annular seal 137 against inner side 63 of cannula support 29 within cannula support 29 neck 35. Annular seal 137 forms an air tight seal against cutter 127 outer surface 153 preventing passage of air through gap 159 between cannula 13 inner surface 39 and cutter 127 outer surface 153 (FIG. 30) effectively sealing the vacuum chamber 121 proximate housing 11 front end 21 during vacuum generation and during generation of the positive pressure to eject tissue sample 59.

Figure 16:
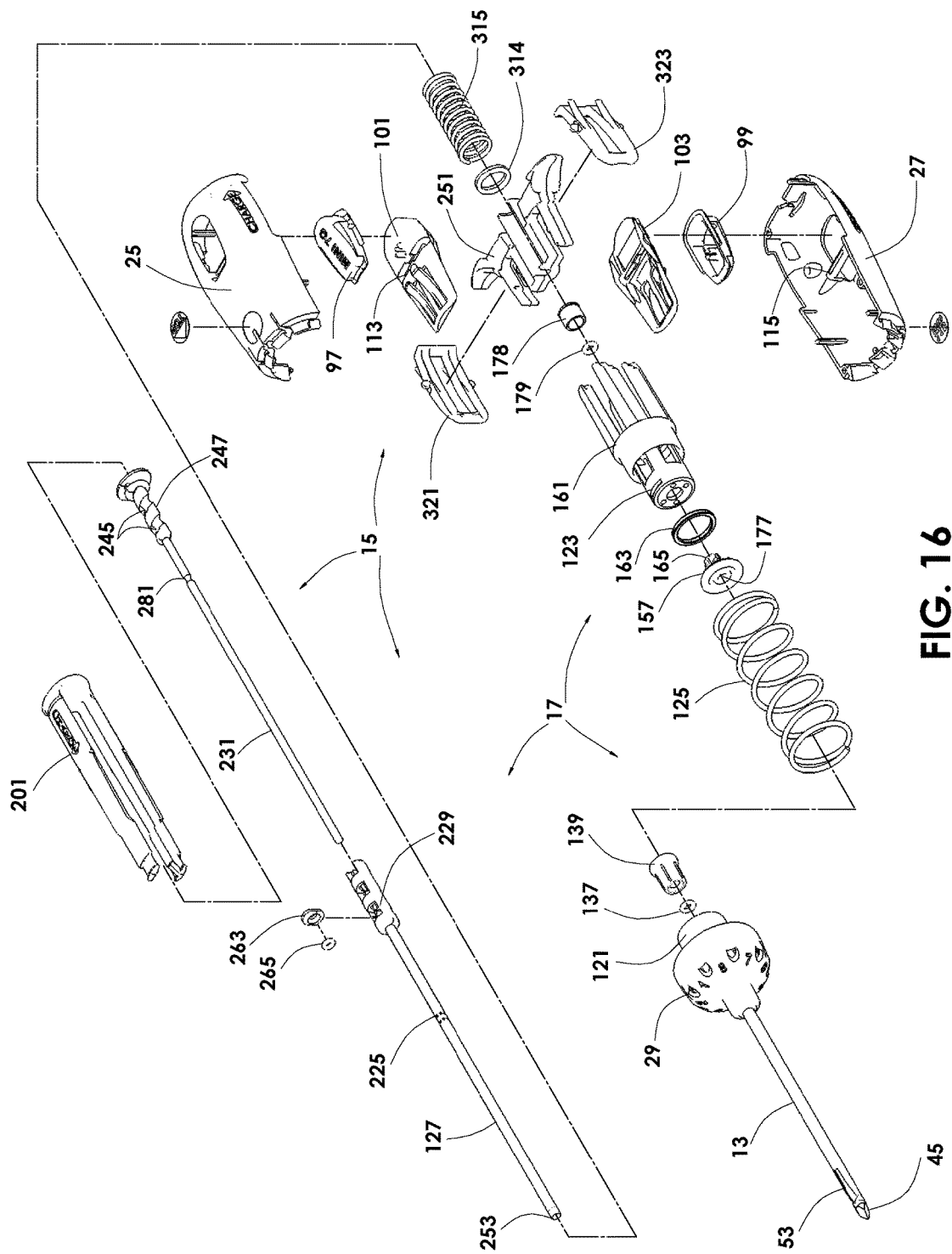
FIG. 16 is an exploded view of the biopsy device of FIG. 1.

Referring further to FIGS. 16, 24A and 28A, annular seal 137, together with seals 179, 265 described below, provide for support of cutter 127. In the embodiments, cutter 127 "floats" on such seals 137, 179, 265 to permit back and forth axial movement of cutter 127 along axis 19 (i.e. translating movement) to maintain an air tight seal during vacuum generation, to permit such air tight seal to be broken when the vacuum is purged and to maintain an air tight seal during generation of the positive pressure to eject tissue sample 59 as described below. Support of cutter 127 by seals 137, 179, 265 provides an opportunity for cost reduction by permitting less exacting tolerances between seal retainer 139, piston 123 and cutter 127 while maintaining the appropriate air tight sealing relationships.

Referring now to FIGS. 16, 18, 19B-19C, 24A, 28A and 39A, exemplary piston 123 may be an integral part of piston carrier 161. Preferably, piston 123 and piston carrier 161 are coaxial with axis 19 and are concentric about cutter 127 which passes through piston 123 as described below. Piston 123 is preferably cylindrical with an outside diameter slightly less than an inside diameter of vacuum chamber 121 cylindrical wall 131. In the examples, piston face 157 retains annular seal 163 against piston 123 by means of stem 165 seated in piston opening 167. Radially outward longitudinal ribs 169 on stem 165 are tapered toward piston opening 167 to facilitate a tight frictional press fit of piston face 157 against piston 123 with annular seal 163 held between piston face 157 and piston 123. In the examples, four alignment posts (one shown as 171) extend away from piston face 157 and into a respective opening 173 in piston 123 to provide a friction fit with piston 123 to further join piston face 157 to piston 123. Adhesive may also be used to secure piston face 157 to piston 123.

Annular seal 163 has an outside diameter slightly greater than that of piston 123 and piston face 157 and the inside diameter of vacuum chamber 121. Annular seal 163 is compressed against cylindrical wall 131 of vacuum chamber 121 when piston 123 is seated therein to provide a sliding air tight seal between piston 123 and cylindrical wall 131 as piston 123 moves axially (i.e., translates) along axis 19 within vacuum chamber 121. Annular seal 163 also maintains a sealing relationship with vacuum chamber 121 cylindrical wall 131 as vacuum chamber 121 is rotated by rotation of cannula support 29.

As shown in FIGS. 16, 18, 24A, 28A and 39A, stem 165 further includes a cylindrical inner wall 175 which defines a cylindrical passage 177 through which cutter 127 extends and passes through piston 123. Annular seal 179 is seated against a proximal end 160 of stem 165 by seal cap 178 (FIG. 24A) held on stem 165 by a friction press fit. Seal cap 178 also includes a passage 180 (FIG. 18) through which cutter 127 extends. Exemplary stem 165, cylindrical inner wall 175, passages 177 and 180, annular seal 179 and seal cap are coaxial with axis 19. Annular seal 179 has an inside diameter which is slightly less than an inside diameter of passage 177. Annular seal 179 forms an air tight seal against cutter 127 outer surface 153 (FIG. 24A) preventing passage of air through piston 123 so that piston 123 effectively seals vacuum chamber 121. Annular seal 179 (together with annular seals 137, 265) provides support for cutter 127 so that cutter 127 can "float" on such seals 137, 179, 265 to permit back and forth axial movement of cutter 127 along axis 19 (i.e. translating movement) to maintain an air tight seal during vacuum generation as previously described. Exemplary piston 123 functions much like the piston of a syringe because axial advancement of piston 123 in the direction of arrow 199 within vacuum chamber 121 (FIGS. 26, 27 and 28A) generates a vacuum at tissue-receiving aperture 53 to draw tissue 47 into tissue-receiving cavity 42 and axial movement of piston 123 the direction opposite arrow 199 within vacuum chamber 121 forces air out of the vacuum chamber 121 to generate a positive pressure at tissue-receiving cavity 42 to eject the tissue sample 59 as described below.

Referring now to FIGS. 16, 18, 19B-19C and 22-23A, exemplary piston carrier 161 further includes an annular spring seat 181 which receives spring 125 and further includes cam posts 183, 185, 187, 189 which extend away from piston 123 toward housing 11 rear end 23. Spring seat 181 may comprise a circular flange extending radially outward from piston carrier 161 with a distal side 191 and a proximal side 193 (FIG. 23A). Spring 125 is preferably a coiled compression spring which includes distal and proximal ends 195, 197. By way of example only, in certain embodiments, spring 125 may have a spring force in a range of approximately 5 to 20 lbs when fully loaded. The aforementioned range may vary depending on the biopsy device embodiment and is not intended to be limiting. Spring 125 proximal end 197 bears against spring seat 181 distal side 191 and spring 125 distal end 195 bears against annular spring seat 182 formed by covers 25, 27 (FIGS. 22-23).

Spring 125 is held in a compressed state between spring seats 181, 182 before operation by respective sear 101, 103 distal ends 117 which bear against spring seat proximal side 193. Spring 125 applies a force against spring seat 181 biasing piston carrier 161 toward housing 11 rear end 23. Operation of trigger mechanisms 93, 95 cause sears 101, 103 to release piston carrier 161 triggering operation of spring 125. The force provided by spring 125 moves piston 123 axially within vacuum chamber 121 in the direction of arrow 199 to produce the vacuum with the vacuum generation mechanism 17 and to trigger operation of the tissue cutting mechanism 15 as described below.

Figure 19A:
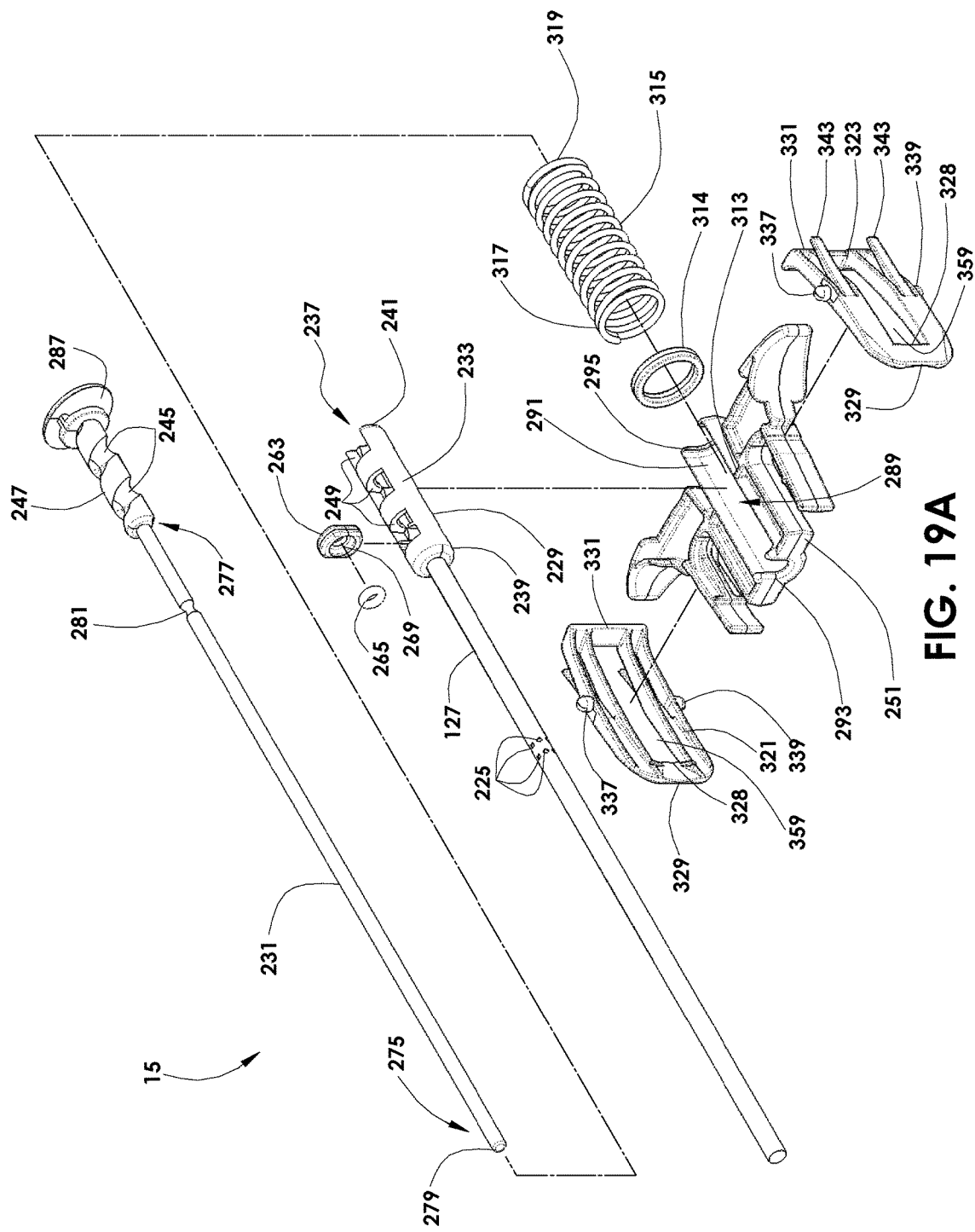
FIG. 19A is an exploded view of exemplary actuator, cutter carrier, follower, cutter, stripper pin and cam subassemblies and related components for use in the biopsy device of FIG. 1.
Figure 19B:
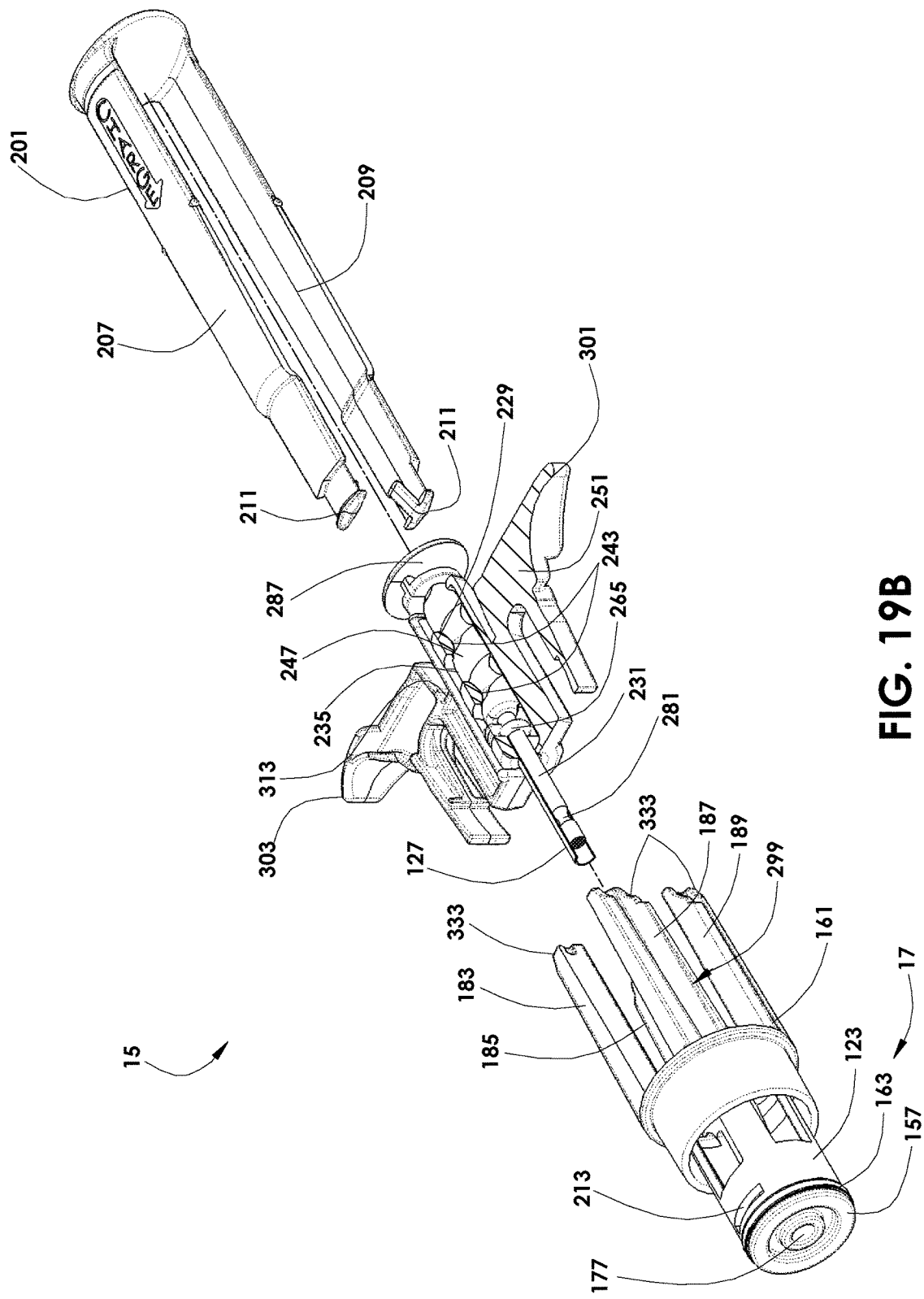
FIG. 19B is an exploded view of exemplary piston, handle, cutter carrier, follower, cutter and cam subassemblies and related components for use in the biopsy device of FIG. 1 with certain surfaces cut away to facilitate understanding.
Figure 19C:
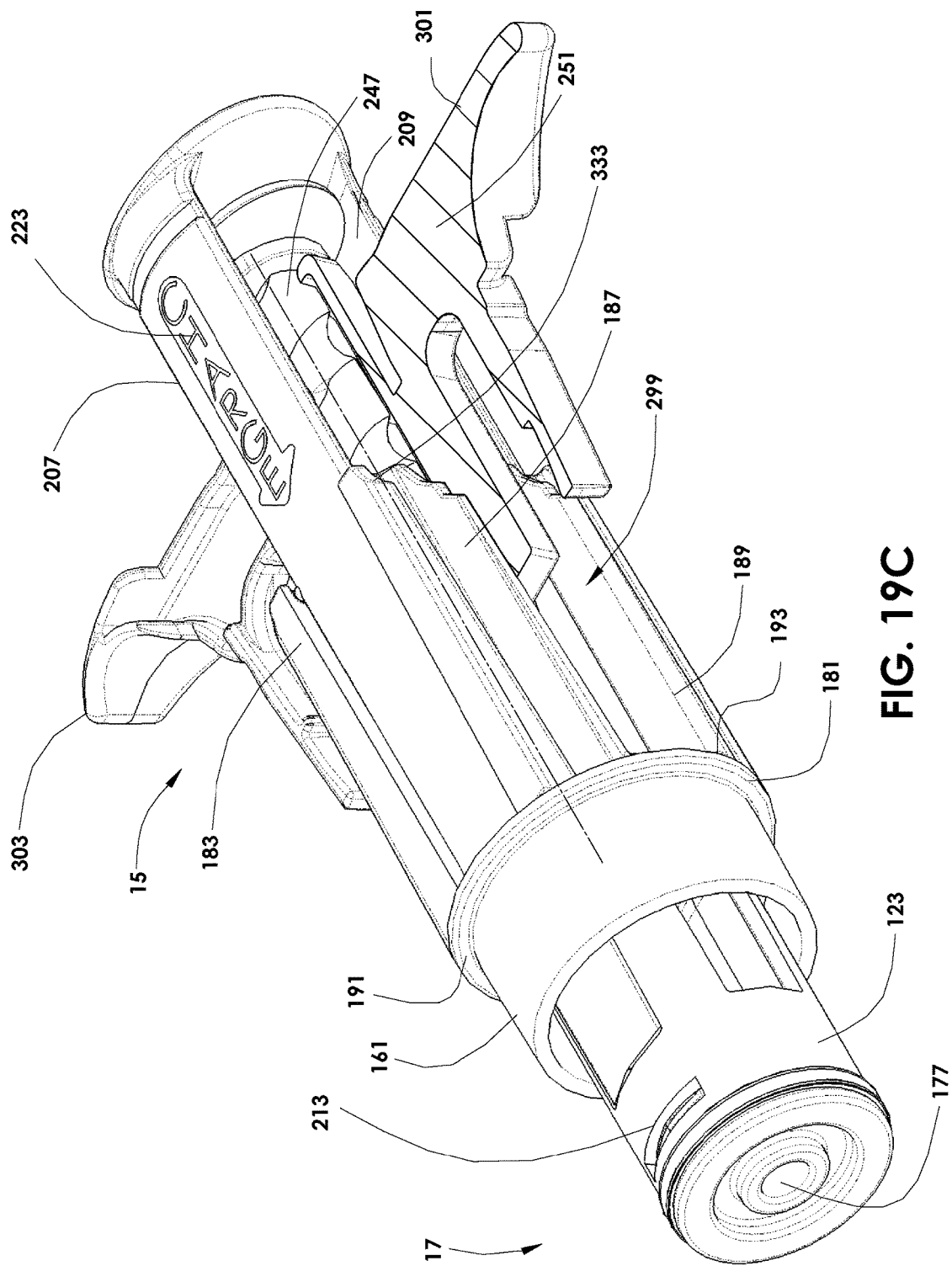
FIG. 19C is an assembly view of exemplary piston carrier, handle, cutter carrier, follower, cutter and cam subassemblies for use in the biopsy device of FIG. 1 with certain surfaces cut away to facilitate understanding.
Figure 29:
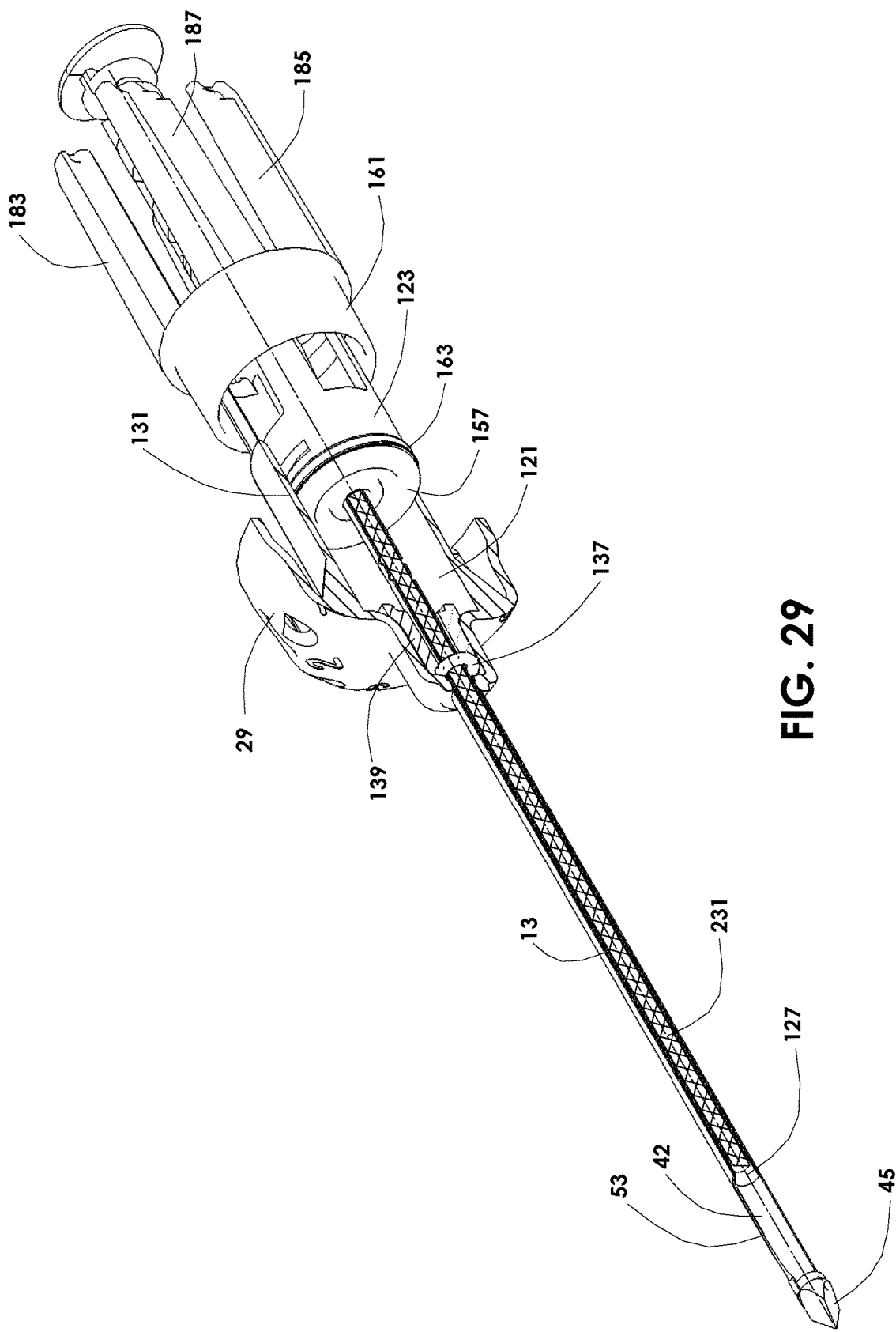
FIG. 29 is a perspective view of the biopsy device of FIG. 1, but in a partially discharged state with certain parts cut away and others removed to facilitate understanding.

Referring now to FIGS. 1-8, 10-11, 16, 18 and 19B-19C, exemplary piston carrier 161 further supports handle 201 which is provided to both compress spring 125 to partially charge biopsy devices 10, 10' and generate air pressure used to eject tissue sample 59 as described below. Handle 201 comprises a distal end 203, a proximal end 205 and a pair of rigid spaced apart runners 207, 209 between ends 203, 205. Referring to FIGS. 19A-19C, spacing of runners 207, 209 permits cutter 127 and other parts described below to be located between runners 207, 209 providing a type of nesting effect between parts and an opportunity for a more compact biopsy device 10, 10' design.

Handle 201 extends through annular spring seat 181 between cam posts 183, 185, 187, 189. Each runner 207, 209 has a flange 211 proximate distal end 203 which is snap fit into a slot (one shown as 213) of piston 123 such that piston seat 161 and handle 201 are joined and handle 201 moves axially with piston carrier 161 along axis 19.

Figure 2:
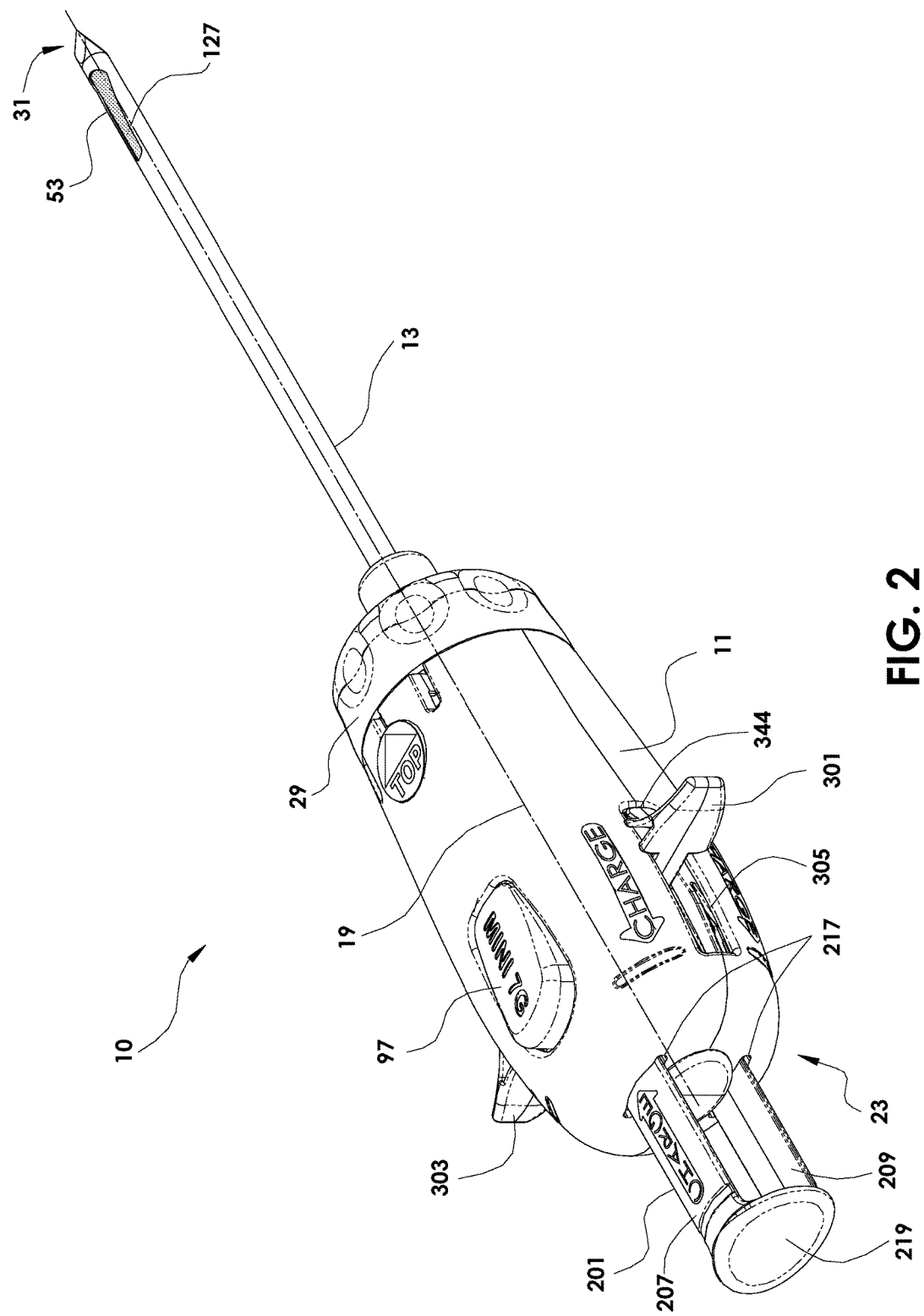
FIG. 2 is a rear side perspective view of the exemplary biopsy device of FIG. 1.
Figure 5:
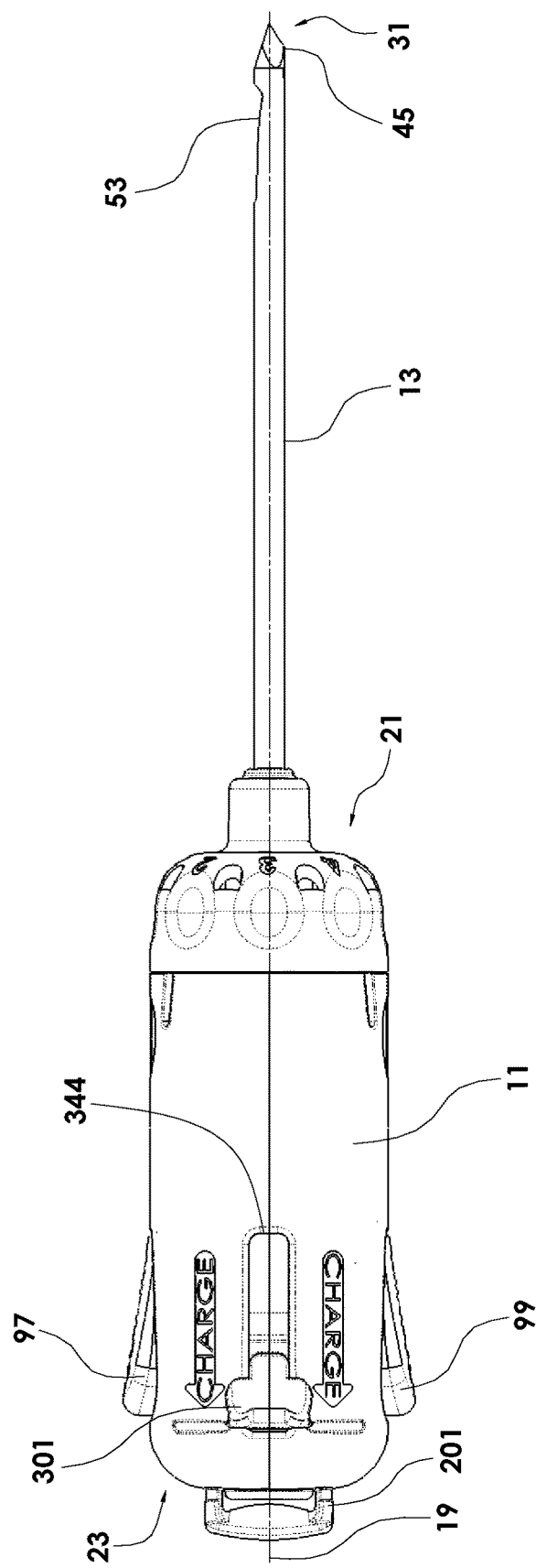
FIG. 5 is a left side elevation view of the biopsy device of FIG. 1, but in a fully charged state.

As shown in FIGS. 2 and 19B, runners 207, 209 travel in corresponding slots 217 provided in covers 25, 27 at rear end 23 of housing 11. Slots 217 act as guides for runners 207, 209 so that handle 201 moves axially along axis 19.

Handle 201 further comprises a push surface 219 (FIGS. 2, 10 and 18) outside of covers 25, 27 at handle 201 proximal end 205. A user pushes against push surface 219, preferably with the user's thumb, in the direction of arrow 221 (FIGS. 39, 42, 43) to apply a force which moves piston 123 distally within vacuum chamber 121 and simultaneously compresses spring 125 for the charging and positive pressure generation purposes (i.e., for tissue sample 59 ejection) as described herein. Indicia 223, such as an arrow and word "CHARGE" (FIG. 19C) may be provided to visually indicate to a user the direction of handle 201 pushing to charge biopsy devices 10, 10'.

Referring to FIGS. 16, 19A, 21-21A, 24-24B, 28-28B, 34-34B and 39-39B, exemplary vacuum generating mechanism 17 further comprises purge valve 129 and air-flow ports 225 which enable the vacuum to be purged during or after tissue sample 59 acquisition to equalize pressure within biopsy devices 10, 10'. In the examples, purge valve 129 comprises a component of both the vacuum generating 17 and tissue cutting 15 mechanisms. Purge valve 129 in its closed state and air-flow ports also contribute to ejection of the tissue sample 59 after acquisition (FIGS. 39A-39B).

Exemplary purge valve 129 comprises an annular seal 265 carried by rotatable follower 229, cutter 127, stripper pin 231 and related components as described herein. It is preferred that exemplary annular seal 265, rotatable follower 229, cutter 127, stripper pin 231 and the related components are each coaxial with axis 19 according to the preferred centerline construction of biopsy devices 10, 10'. Also in the examples, stripper pin 231 is concentric with, and within, cutter 127, seal 265 and rotatable follower 229.

As shown in FIGS. 19A-19B, rotatable follower 229 comprises a cylindrically-shaped outer surface 233, a cylindrically-shaped inner surface 235, a passage 237 through rotatable follower 229, a distal end 239 and a proximal end 241. Inner surface 235 includes inwardly-facing followers 243 oriented in a spiral path. Followers 243 mesh with a spiral cam track 245 of cam 247 for purposes of generating a rotational force (i.e., torque) which rotates rotatable follower 229 and cutter 127 as described below. Cam track 245 preferably comprises a recess while followers 243 are protrusions which ride within cam track 245. In embodiments, cam track 245 may comprise a concave radius with smooth surfaces while followers 243 may have a complementary convex radius, also with smooth surfaces. Persons of skill in the art will appreciate that followers 243 may, for example, comprise recessed (i.e., female) female followers while cam track 245 may comprise a protruding (i.e., male) cam track.

Follower 229 outer surface 233 may define alternating openings 249 to facilitate manufacture, particularly in a plastic injection molding process. Rotatable follower 229 is carried by cutter carrier 251 for axial movement back and forth along axis 19 and for simultaneous rotational displacement of rotatable follower 229 and cutter 127 as described below.

Referring to FIGS. 16, 19A, 21-21A, 22, 23, 24-26, 27-32, 33-40 and 42, 43, exemplary cutter 127 is shown as a "cutter cannula" and it is to be understood that cutter 127 may include a cutter cannula type cutter 127. Exemplary cutter 127 is supported by rotatable follower 229 and includes rotatable follower 229 fixedly joined thereto. Cutter 127, including rotatable follower 229, co-rotate for purposes of tissue cutting, severing, shearing and tissue sample 59 acquisition as described below.

Exemplary cutter 127 may comprise a cylindrical tube (i.e., a cannula) 228 (FIGS. 21-21A, 30) which extends from rotatable follower 229 to a cutter distal end 253. Cylindrical tube 228 of cutter 127 and cutter proximal end 255 extend into rotatable follower 229 in communication with passage 237 of rotatable follower 229. As illustrated in FIGS. 24B and 28B, rotatable follower 229 may be joined to cutter 127 to form a one-piece cutter cannula 127 by means of an over-molding process as described in connection with cannula support 29.

Figure 30:
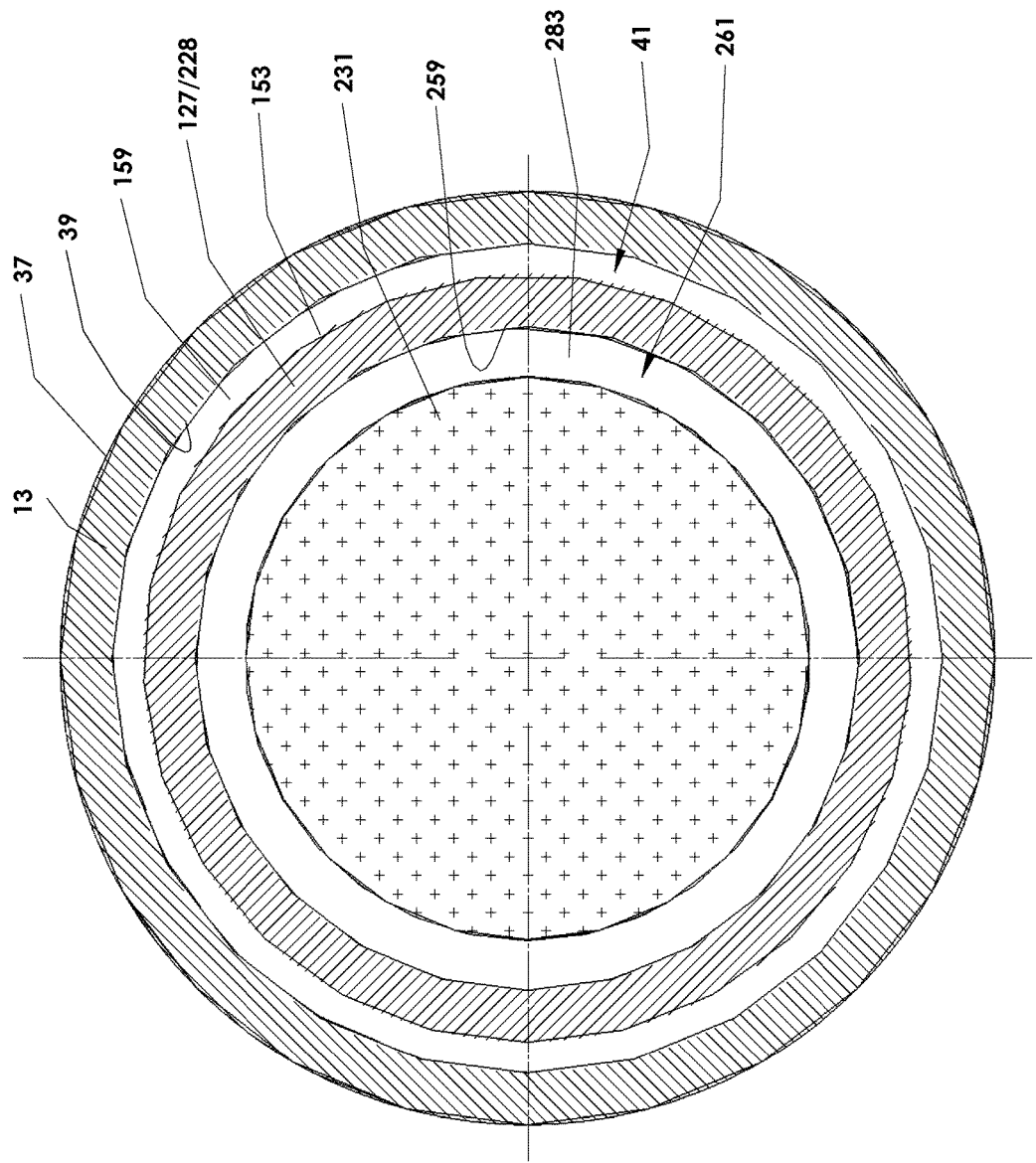
FIG. 30 is a section view taken along section 30-30 of FIG. 8.

As shown in FIG. 30, exemplary cutter 127 further comprises an outer surface 153 and an inner surface 259 which defines a hollow lumen 261 between distal and proximal ends 253, 255. In the examples, cutter 127 proximal end 255 is open and provides a purge port 256 permitting flow of ambient air within housing 11 through cutter lumen 261 and into vacuum chamber 121 and cannula 13 lumen 41 purging the vacuum produced by vacuum generating mechanism 17 as described herein.

As shown for example in FIGS. 1-2, 22, 29-30 and 35-36, exemplary cutter 127 extends distally within cannula 13 lumen 41 along axis 19 and is coaxial and concentric with cannula 13 in the examples. Cannula 13 provides an outer cannula for cutter cannula 127 in the examples.

As illustrated in FIGS. 21A and 21B, cutter distal end 253 preferably includes an inscribed cutter edge 262 entirely or partially around the tubular circumference of cutter 127 distal end 253. An inscribed cutter edge 262 is a sharpened knife-like edge (i.e., an inclined plane forming a cutting edge) in which the cutter inner surface 259 is machined or otherwise provided with a narrow extremely sharp cutter edge 262 which is highly-efficient in cutting, severing and shearing tissue 47. As illustrated in FIGS. 21, 21A and 21B, inscribed edge 262 is most preferably around the entire circumferential distal end 253 of cutter 127 tube 228. Other types of cutting, severing, cutting and/or shearing surfaces may be provided on cutter 127.

As shown in FIGS. 16, 19A, 24B, 28B, 34B and 39B, exemplary rotatable follower 229 further supports elements of purge valve 129. In the examples, rotatable follower 229 supports a seal trap 263 which supports an annular seal 265 which is part of purge valve 129. Annular seal 265 is preferably an O-ring, a rubber washer or some other material. Preferred seal trap 263 includes a seat 267 which receives and supports annular seal 265. Seal trap 263 further comprises an opening 269 permitting stripper pin 231 to be inserted through and within seal trap 263 and annular seal 265. Seal trap 263 and annular seal 265 supported therein is seated in rotatable follower 229 by means of a press fit between rotatable follower distal wall 271 and rotatable follower stop wall 273. Seal trap 263 is held in rotatable follower 229 such that annular seal 265 is coaxial with axis 19. Annular seal 265 inside diameter is slightly less than an outside diameter of stripper pin 231. As shown in FIGS. 24B, 28B and 39B, annular seal 265 forms an air tight seal against stripper pin 231 when purge valve 129 is in its closed state, or position, preventing purging of the vacuum, in vacuum chamber 121 until purge valve 129 is opened, permitting ambient air flow into purge port 256 to purge the vacuum as described below. Also in the closed state of purge valve 129, annular seal 265 provides support for follower 229 and cutter 127 extending distally from follower 229 which, along with seals 137 and 179 facilitates "floating" support of cutter 127. Contact between annular seal 265 and stripper pin 231 also provides support for stripper pin 231 distal cam 247.

Referring to FIG. 19A, exemplary stripper pin 231 preferably comprises an elongate cylindrical shaft, or member, having a distal end 275, a proximal end 277, a tissue stop surface 279 and an annular notch 281 distal from proximal end 277. Preferably, stripper pin 231 is a solid shaft because a lumen within stripper pin 231 is not needed. As shown in FIGS. 16, 19A-19C, 24, 24B 28, 28B, 31, 34, 34B, 36, 39 and 39B, stripper pin 231 is fixedly joined with cam 247 such that stripper pin 231 is in a fixed position coaxial with axis 19 and does not rotate or move axially along axis 19. Stripper pin 231 proximal end 277 extends into cam 247 and may be joined to cam 247 by means of an over-molding process as described in connection with cannula support 29 and rotatable follower 229.

As shown in FIGS. 34 and 34B, purge valve 129 is placed in an open state, or position, when cutter 127, rotatable follower 229 and annular seal 265 supported by rotatable follower 229 are advanced along axis 19 in the direction of arrow 221 causing seal 265 to align with notch 281 thereby breaking the air tight sealing contact between stripper pin 231 and annular seal 265. Breaking such air tight sealing contact allows ambient air to flow into purge port 256, between annular seal 265 and notch 281, through cutter 127 lumen 283, through air-flow ports 225 and into vacuum chamber 121, cannula 13 lumen 41 and tissue-receiving cavity 42 to immediately purge the vacuum therein.

FIG. 30 is a cross-sectional view which illustrates the relationship between cannula 13, cutter 127 and stripper pin 231 of the exemplary embodiments. Cannula 13, cutter 127 and stripper pin 231 are each coaxial with axis 19. Cannula 13 is concentric about both cutter 127 and stripper pin 231 and both cutter 127 and stripper pin 231 are within cannula 13 and cannula lumen 41. Cutter 127 is concentric about stripper pin 231 and stripper pin 231 is within cutter 127 and cutter lumen 261. A gap 159 exists between cannula 13 inner surface 39 and cutter 127 outer surface 153 and a gap 283 exists between cutter 127 inner surface 259 and stripper pin 231. Air can flow through gaps 159, 283 for purposes of generating a vacuum, at tissue-receiving aperture 53 and in tissue-receiving cavity 42 or purging the vacuum. Pressurized air can flow from vacuum chamber 121 and through gap 283 to eject a tissue sample 59 as described below.

Referring now to FIGS. 16, 19A, 21-21A, 24A, 28A, 34A and 39A, air-flow ports 225 preferably comprise plural ports through cutter 127 and the cylindrical tube 228 of the cutter cannula type cutter 127. In the examples, two spaced apart rows of air-flow ports 225 are provided around outer 153 and inner 259 surfaces of cutter 127. Air-flow ports 225 other than two spaced apart rows of air-flow ports 225 may be implemented. Air-flow ports 225 permit air to flow and be drawn through gap 283 between cutter 127 and stripper pin 231 and into vacuum chamber 121 during generation of the vacuum and further permit pressurized air to be forced from vacuum chamber 121 to eject tissue sample 59 through tissue-receiving aperture 53.

As described below, axial movement of cutter 127 and rotatable follower 229 along axis 19 (i.e., translating movement) during operation, positions air-flow ports 225 relative to vacuum chamber 121 to permit air flow though cutter 127 and, further, opens and closes purge valve 129 as described below.

FIGS. 24-24B show air-flow ports 225 positioned within vacuum chamber 121 and purge valve 129 in a closed state before vacuum generation.

FIGS. 28-28B show air-flow ports 225 positioned within vacuum chamber 121 and purge valve 129 in a closed state during vacuum generation.

FIGS. 34-34B show air-flow ports 225 in a position axially advanced toward housing 11 front end 21 in which the two rows of air-flow ports 225 straddle annular seal 137 with purge valve 129 in an open position, or state, enabling the vacuum in vacuum chamber 121 to be purged with ambient air movement through purge port 256 and into vacuum chamber 121 through air-flow ports 225. Opening of purge valve 129 further purges vacuum within gaps 159 and 283 and at tissue-receiving aperture 53 as air flows through air-flow ports 225 distal annular seal 137 to release forces holding tissue 47 against cannula 13 so that biopsy device 10, 10' can be freely removed from the patient's body, minimizing patient discomfort and improving the quality of care.

FIGS. 39-39A show air-flow ports 225 positioned within vacuum chamber 121 as cutter 127 is axially retracted in the direction of arrow 199 with purge valve 129 in a closed state during generation of a positive air pressure at tissue-receiving aperture 53 to eject the tissue sample 59 therefrom.

FIGS. 28-28B, 34-34B and 39-39B all include exemplary directional arrows indicating the locations and directions of air flow during operation of biopsy devices 10, 10'. Persons of skill in the art will appreciate that FIGS. 28-28B, 34-34B and 39-39B are all section views and that air movement in the directions indicated by the arrows is within cannula 13 lumen 41 and cutter 127 lumen 261 around cutter 127 and stripper pin 231 in the examples.

As illustrated in FIGS. 1-2, 11, 32, 33, 34, 35, cutter 127 is fully across tissue-receiving aperture 53 and closes such tissue-receiving aperture 53 with the acquired tissue sample 59 within lumen 261 of cutter 127. Movement of cutter 127 across tissue-receiving aperture 53 cuts, severs and shears tissue 47 to provide the tissue sample 59 in the examples. The cutting, severing and shearing action of the examples differ from an axial coring action.

A vacuum across tissue-receiving aperture 53 draws tissue 47 tightly against cannula 13 potentially making it difficult to remove cannula 13 from the patient without discomfort. Positioning of air-flow ports 225 straddling annular seal 137 enables the vacuum proximate tissue-receiving aperture 53 to be immediately purged after tissue 47 cutting, severing and shearing, thereby releasing forces drawing and holding tissue 47 surrounding cannula 13 against cannula 13 proximate the closed tissue-receiving aperture 53 after cutting.

As illustrated in FIGS. 37-40, retraction of cutter 127 back toward housing 11 rear end 23 in the direction of arrow 199 during charging of biopsy device 10, 10' and tissue sample 59 ejection following tissue cutting, severing and shearing returns air-flow ports 225 back toward housing 11 rear end 23 to a position between annular seal 137 and vacuum chamber 121 and closes purge valve 129 so that pressurized ambient air pushed out of vacuum chamber 121 flows through air-flow ports 225 and into gap 283 between cutter 127 and stripper pin 231 to eject tissue sample 59 from tissue-receiving cavity 42 through tissue-receiving aperture 53.

In the embodiments, a relationship between vacuum generating mechanism 15 and cutter 127 exists wherein vacuum generating mechanism 17 is around at least a portion of cutter 127. As a result of this relationship, vacuum generating mechanism 17 can be in air-flow communication with cannula 13 and tissue-receiving cavity 42 through cutter 127 to produce a vacuum in tissue-receiving cavity 42 by drawing air through cannula 13 and cutter 127. The vacuum can be purged by opening purge valve 129 which is also in air-flow communication with vacuum generating mechanism 15, cannula 13 and tissue-receiving cavity 42. And, air forced by vacuum generating mechanism 17 through cutter 127 can be used to eject a tissue sample 59 through tissue-receiving aperture 53 once purge valve 129 is closed.

Exemplary Tissue Cutting Mechanism

Referring now to FIGS. 1, 11, 16-21B, 30-31 and 32-40, exemplary tissue cutting mechanism 15 capable of use in biopsy devices 10, 10' comprises cannula 13, tissue-receiving aperture 53, cutter 127, rotatable follower 229, cutter carrier 251, stripper pin 231, cam 247, spring 315, sears 321, 323 and related components as described herein. Exemplary tissue cutting mechanism 15 serves to advance and, alternatively, retract cutter 127 axially (i.e, translating movement) along axis 19, while simultaneously rotating cutter 127 about axis 19. Advancement and retraction of cutter 127 enables both tissue 47 acquisition and operation of the vacuum generating mechanism 17 and purge valve 129 as described herein.

These alternative axial movements of cutter 127 are referred to herein as an advancement stroke and a retraction stroke. Cutter 127 is initially retracted during vacuum generation. During the advancement stroke, cutter 127 is advanced within cannula lumen 41 in the direction of arrow 221 to close tissue-receiving aperture 53 and to cut, sever and shear tissue 47 in tissue-receiving aperture 53 and tissue-receiving cavity 42. During the advancement stroke, the position of air-flow ports 225 and seal 265 permits immediate purging of the vacuum after tissue 47 is cut, severed and sheared.

During the retraction stroke, cutter 127 is retracted within cannula 13 lumen 41 in the direction of arrow 199 to open tissue-receiving aperture 53 for ejection of the tissue sample 59. During the retraction stroke, the position of air-flow ports 225 and seal 265 permits the vacuum generating mechanism 17 to force air through cutter 127 toward tissue-receiving aperture 42 for the tissue sample 59 ejection. Exemplary cannula 13, cutter 127, rotatable follower 229, cutter carrier 251, stripper pin 231, cam 247 and spring 259 are preferably coaxial with axis 19 according to the preferred centerline construction of biopsy devices 10, 10'.

Also in the examples, spring 315 comprises a second biasing device, the purpose of which is to operate tissue cutting mechanism 15. Preferably, operation of tissue cutting mechanism 15 is triggered in a sequence after operation of vacuum generating mechanism 17 has been triggered. In embodiments, operation of tissue cutting mechanism 15 is triggered as vacuum generating mechanism 17 approaches completion of its vacuum-generating cycle with piston 123 approaching proximal end 133 of vacuum chamber 121.

Referring to FIGS. 19A-19C, cam 247 is preferably seated in slot 285 formed by covers 25, 27. Cam 247 is keyed to fit in slot 285 so that cam 247 is supported with respect to covers 25, 27 in fixed position so that cam 247 and stripper pin 231 joined to cam 247 do not move axially or rotationally. Cam base 287 abuts cover outer surface 89 also to prevent axial movement of cam 247 and stripper pin 231 joined to cam 247.

As is shown, for example, in FIGS. 16, 19A-19C, cam 247 is preferably elongate and generally cylindrical in shape. Cam 247 further comprises a spiral cam track 245. In the examples, spiral cam track 245 is a female track coaxially disposed about axis 19. Spiral cam track 245 is preferably symmetrically disposed about axis 19 and may be a helical track.

Cam 247 is received within rotatable follower 229 inner passage 237 and rotatable follower 229 is driven to rotate by cam 247. In the examples, spirally-disposed followers 243 project inward from follower inner surface 235 and mesh with cam track 245. Cam 247 generates a rotational force (i.e., torque) on follower 229 as follower 229 carried by cutter carrier 251 moves axially to rotate follower 229 and cutter 127.

Figure 36:
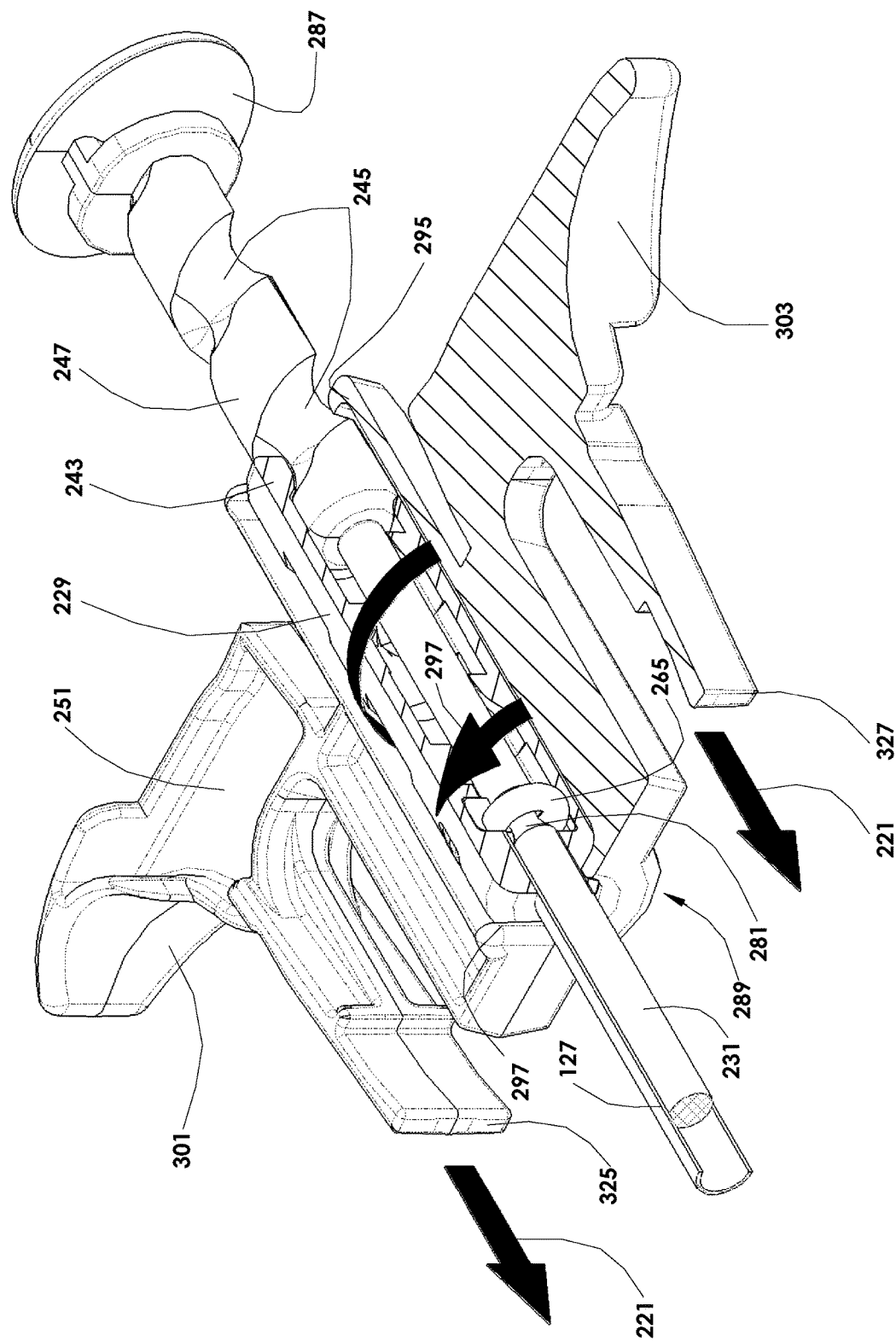
FIG. 36 is a perspective view of the exemplary cutter carrier, follower, cutter, stripper pin and cam subassemblies in the fully discharged state.

Referring to FIGS. 19-19C and 36, cutter carrier 251 moves along axis 19 and rotatably supports cutter 127 and rotatable follower 229 of cutter 127 enabling the advancement and retraction strokes along axis 19. Cutter carrier 251 includes an elongate cradle 289 defined by a half-cylinder wall 291, distal wall 293 and proximal wall 295. Distal wall 293 includes an opening 294 through which cutter 127 passes through distal wall 293 and proximal wall 295 includes an opening 296 through which cam 247 is received so that cam 247 and rotatable follower 229 are in meshed engagement.

Figure 35:
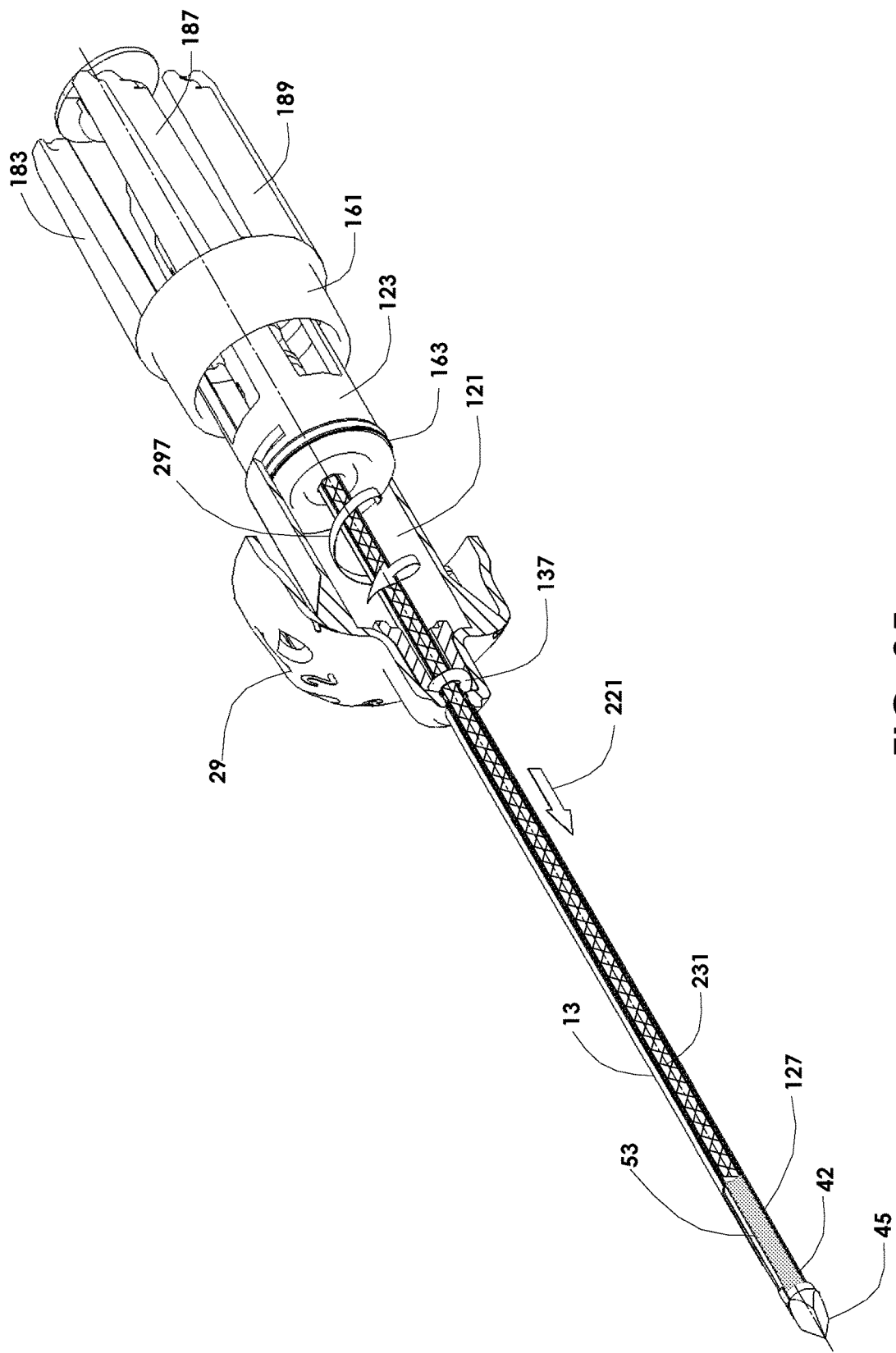
FIG. 35 is a perspective view of the biopsy device of FIG. 1 during operation toward a fully discharged state with certain parts cut away and others removed to facilitate understanding.

Half-cylinder wall 291 is complementary with rotatable follower 229 outer surface 233 and preferably is of a low-friction material permitting rotatable follower 231 to rotate within cradle 289 in the direction of arrow 297 (FIG. 36) during the advancement stroke when cutter carrier 251 and follower 229 move axially in the direction of arrow 221. Such follower 229 rotation also causes cutter 127 rotation in the direction of arrow 297 as shown in FIG. 35. Follower 229 and cutter 127 rotate in the direction opposite arrow 297 during the retraction stroke when cutter carrier 251 and follower 229 move in the direction of arrow 199. Distal and proximal walls 293, 295 limit axial movement of rotatable follower 229 within cradle 289 so that an axial force is applied to rotatable follower 229 during each of the advancement and retraction strokes. Thus, cutter 127 rotation occurs simultaneously with cutter 127 advancement or retraction.

Referring to FIGS. 19B and 19C, cutter carrier 251 is preferably located in a slot 299 existing between the pair of cam posts 183, 185 and the pair of cam posts 187, 189 and further between runners 207, 209 of handle 201. Cutter carrier 251 further includes a pair of charging handles 301, 303 which may have a hook-like configuration for ease of pulling with a user's fingers. Exemplary charging handles 301, 303 are mirror images of each other and extend out of housing 11 through slots 305, 307 defined by edges 309, 311. Charging handles 301, 303 may ride on edges 309, 311 to further support cutter carrier 251 with respect to housing 11. Cutter carrier 251 is supported indirectly (i.e., with respect to) housing 11 between cam post pairs 183, 185 and 187, 189. Cutter carrier 251 may float with respect to housing 11 and may be guided in part by contact between charging handles 301, 303 and edges 309, 311 forming slots 305, 307 (FIG. 19).

As shown in FIGS. 19-19C, exemplary cutter carrier 251 further includes a spring seat 313 which receives annular spring bearing 314 and spring 315 located partially around cradle 289. Annular spring bearing 314 is of a wear-resistant material which protects cutter carrier 251 from damage by spring 315. Spring 315 is preferably a coiled compression spring which includes distal and proximal ends 317, 319. Spring 315 may have a spring force which is less than that of spring 125 for the reasons described below. By way of example only, spring 315 may have a spring force in a range of approximately 1 to 5 lbs. when fully loaded. The aforementioned range may vary depending on the biopsy device embodiment and is not intended to be limiting. Differential spring forces of springs 125, 315 enables vacuum generating mechanism 17 to be preferentially charged after charging of tissue cutting mechanism 15, thereby enabling pressurized air from vacuum generating mechanism 17 to eject the tissue sample 59.

Spring 315 distal end 317 bears against cutter carrier 251 spring seat 313 and annular spring bearing 314 while spring proximal end 317 bears against cover inner surface 91 on housing 11 rear end 23 (FIG. 22). Spring 315 is further positioned around cam 247. Spring 315 is compressed between spring seat 313 and housing 11 and applies a force against spring seat 313 biasing cutter carrier 251 toward housing 11 front end 21. Such force moves cutter carrier 251 axially toward housing front end 21 in the direction of arrow 221.

While spring-type biasing devices 125, 315 are preferred, other types of biasing devices motion-generating devices may be utilized to produce motion consistent with the invention as will be appreciated by those of ordinary skill in the art. For example, spring-type devices other than springs 125, 315 may be utilized. By way of further example, springs 125, 315 could be replaced with pneumatic or hydraulic biasing devices. Such pneumatic or hydraulic biasing devices may be a dual-acting air cylinder or dual acting hydraulic cylinder with an appropriate source of pressurized air or liquid to bias piston 123 and cutter carrier 251 in the direction of arrow 199 and, alternatively, in the direction of arrow 221 for the purposes of operating tissue cutting mechanism 15 and vacuum generating mechanism 17 as described in connection with springs 125, 315. The source of pressurized air or liquid could be on board the biopsy device, remote from the biopsy device and supplied through suitable conduits or a combination of on board and remote sources.

As shown in FIGS. 19-19A, 26A, 31, 32A and 36, spring-biased movement of cutter carrier 251 in the direction of arrow 221 is controlled by sears 321, 323 which coact with cutter carrier stop surfaces 325, 327. Together with trigger mechanisms 93, 95, sears 321, 323 comprise an actuator which triggers sequential operation of the first and second biasing devices 125, 315. Sears 321, 323 are each a pivoted part that retains cutter carrier 251 in position against spring 315 before operation. Contact between sear stop surface 328 proximal sear distal end 329 and a respective cutter carrier stop surface 325, 327 prevents spring-driven movement of cutter carrier 251 in the direction of arrow 221. Each sear 321, 323 pivots when a respective sear proximal end 331 is contacted by a respective cam surface 333 on proximal end of each cam post 183-189. Each cam surface 333 contacts a sear proximal end 331 as a result of operation of trigger mechanisms 93, 95 causing spring 125 to move piston carrier 161 and cam posts 183-189 in the direction of arrow 199.

Pivoting movement of sears 321, 323 causes the respective sear stop surface 328 to respectively move inward and out of contact with the cutter carrier stop surfaces 325, 327. FIG. 26A arrow 335 illustrates the direction of inward pivoting movement of sear 321 distal end 329. (Sear 323 distal end 329 pivots inward in the same manner.) Movement of the respective sear stop surface 328 out of contact with the cutter carrier stop surfaces 325, 327 occurs simultaneously and enables spring 315 to advance cutter carrier 251 axially in the direction of arrow 221. Thus, a preferred operating sequence is for spring-driven (i.e., spring 125) movement of piston carrier 161 in the direction of arrow 199 to trigger operation of sears 321, 323 followed closely by spring-driven (i.e., spring 315) movement of cutter carrier 251 in the direction of arrow 221.

Each sear 321, 323 may be identical and has a pair of male coaxial pivot pins 337, 339 which are seated in coaxial female bosses in respective covers 25, 27, one of which 341 is illustrated in FIGS. 16 and 19. Pins 337, 339 in bosses (e.g., boss 341) permit respective sear 321, 333 distal end 329 to pivot inward (as illustrated by arrow 335 for sear 321 in FIG. 26A) and, alternatively, outward. Each sear 321, 323 distal end 329 is biased outward and rests against a respective inner surface 91 of one of the covers 25, 27 while each sear 321, 323 proximal end 331 is biased inward by integral springs 343 which extend toward and contact a respective cover inner surface 91 (FIG. 19) to retain cutter carrier 251 in its charged state before operation as described below.

Figure 31:
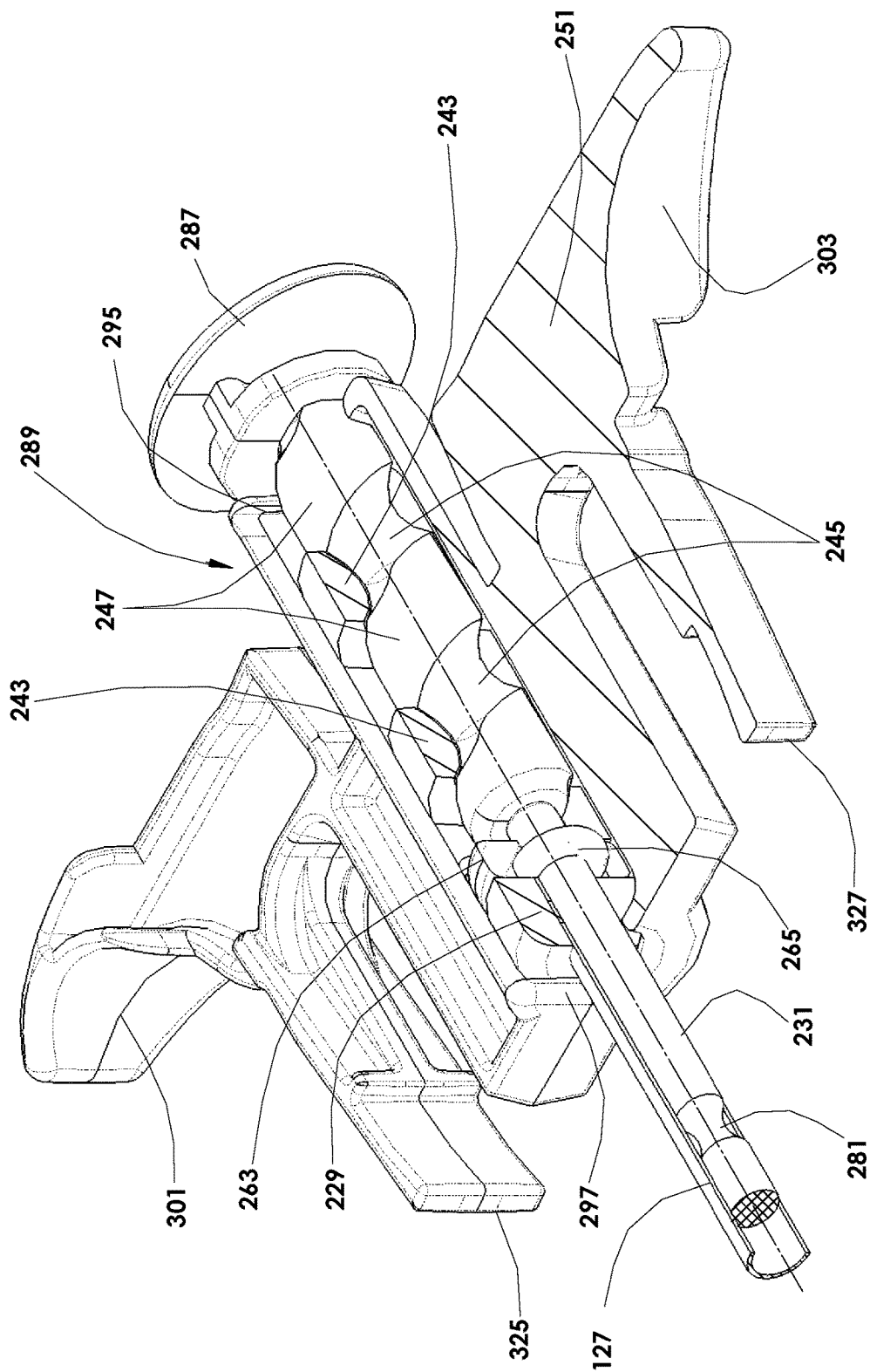
FIG. 31 is a perspective view of the exemplary cutter carrier, follower, cutter, stripper pin and cam subassemblies before operation of the exemplary tissue cutting mechanism.

Cutter carrier 251 advancement in the direction of arrow 221 is limited by stops 344, 345 (FIGS. 2-3). Cutter carrier 251 retraction in the direction of arrow 199 is limited by contact between cutter carrier 251 proximal wall 295 and cam base 287 (FIG. 31). Referring to FIGS. 23A and 26A, preferred sears 101, 103 and 321, 323 respectively include ramp structure 118 or 322 which facilitate automatic resetting of the respective sears 101, 103, 321, 323 during charging of biopsy devices 10, 10'. As described herein, exemplary biopsy devices 10, 10' may be reset to the fully charged state following an operational cycle by pushing, or advancing, handle 201 in the direction of arrow 221 while pulling, or retracting, charging handles 301, 303 in the direction of arrow 199.

For exemplary sears 101, 103, FIG. 23A illustrates exemplary ramp 118 of sears 101, 103 which facilitates charging of vacuum generating mechanism 17. To charge vacuum generating mechanism 17, piston carrier 161 is advanced in the direction of arrow 221 by pressing against handle 201 push surface 219. During advancement of piston carrier 161, inclined ramp 118 contacts and rides over spring seat 181 urging sears 101, 103 to pivot against the force of integral springs 119. Once spring seat 181 passes sear distal end 117, each spring 119 biases respective sear 101, 103 so that each distal end 117 of respective sear 101, 103 automatically engages spring seat 181 proximal side 193 preventing retraction, or rearward movement toward housing rear side 23, of piston carrier 161 in the direction or arrow 199 and retaining spring 125 in a compressed state as illustrated in FIG. 23A.

For exemplary sears 321, 323, FIG. 26A illustrates exemplary ramp 322 of sears 321, 323 which facilitates charging of tissue cutting mechanism 15 and automatic resetting of sears 321, 323. To charge tissue cutting mechanism 15, cutter carrier 251 is retracted in the direction of arrow 199 by user pulling of charging handles 301, 303 rearward toward housing rear end 23. During retraction of cutter carrier 251, inclined ramp 322 contacts and rides over a respective cutter carrier 251 stop surface 325, 327 urging sears 321, 323 to pivot against the force of integral springs 343. Once respective cutter carrier stop surface 325, 327 passes sear stop surface 328, each spring 343 biases respective sear 321, 323 so that each stop surface 328 of respective sear 321, 323 automatically engages a cutter carrier stop surface 325, 327 preventing advancement of cutter carrier 251 in the direction of arrow 221 and retaining spring 315 in a compressed state as illustrated in FIG. 26A.

Cutter carrier 251 may be held in a position such that cutter 127 (supported by cutter carrier 251) is fully retracted and does not obstruct tissue-receiving aperture 53 as illustrated in FIGS. 22 and 23. Such a retracted position of cutter 127 would leave tissue-receiving aperture 53 fully open to receive a maximum amount of tissue 47 therethrough. Once sears 101, 103 and 321, 323 are fully engaged, biopsy device 10, 10' is in the fully charged state.

Further Exemplary Tissue Cutting Mechanism Embodiment

FIGS. 42-43 illustrate a further tissue cutting mechanism embodiment 15' in which cutter 127 can be positioned partially across tissue-receiving aperture 53 when biopsy devices 10, 10' are in a fully charged state. Partial obstruction of tissue-receiving aperture 53 by cutter 127 could be advantageous for a use in a biopsy procedure in which a tissue sample 59 of a lesser volumetric size would be desired. An example of such a biopsy procedure may be a subcutaneous biopsy procedure in which tissue 47 of interest is situated in close proximity to the patient's skin making a tissue sample 59 of a lesser volumetric size necessary or more desirable. Partial obstruction of tissue-receiving aperture 53 limits the amount of tissue 47 that can be inducted through tissue-receiving aperture 53.

Partial obstruction of tissue-receiving opening 53 by cutter 127 results from the position in which cutter carrier 251 is stopped when in the fully charged state of biopsy devices 10, 10'. As shown in FIGS. 42-43, cutter carrier 251 may optionally include a further pair of cutter carrier stop surfaces 347, 349 proximal from stop surfaces 325, 327. Stop surfaces 347, 349 are stopped by a respective sear stop surface 328 as described in connection with cutter carrier 251 stop surfaces 325, 327. However, the position of stop surfaces 347, 349 proximal from stop surfaces 325, 327 causes cutter carrier 251, rotatable follower 229 and cutter carrier 127 supported thereby, to be held at a partially advanced, or intermediate, position whereby cutter 127 and cutter 127 distal end 253 are partially across tissue-receiving aperture 53 while in a fully charged state of biopsy devices 10, 10'. In such partially advanced position and as illustrated in FIGS. 42-43, cutter 127 distal end 253 could obstruct a portion of tissue-receiving aperture 53, leaving the remainder of tissue-receiving aperture 53 unobstructed to receive tissue 47 therethrough.

In the examples of FIGS. 42-43, cutter carrier 251 is held in a charged state by contact between cutter carrier stop surfaces 347, 349 and sear stop surfaces 328 such that cutter 127 partially obstructs tissue-receiving aperture 53 by approximately 40%, leaving the remaining portions of tissue-receiving aperture 53 unobstructed. However, cutter carrier stop surfaces 347, 349 may be located at multiple other positions on cutter carrier 251 permitting cutter 127 to partially obstruct tissue-receiving aperture 53 within an exemplary range of between about 5% to about 75% obstruction.

Exemplary Operation of the Tissue Cutting Mechanism

Referring to FIGS. 19-19C, 31 and 36 and as described below, spring-driven axial movement of cutter carrier cannula 127 and rotatable follower 229 along axis 19 (i.e., translating movement) during operation causes simultaneous advancement and rotational movement of cutter 127 during the advancement stroke and retraction and rotational movement of cutter 127 during the retraction stroke. During the advancement stroke, axial movement of cutter carrier 251 in the direction of arrow 221 causes cutter carrier proximal wall 295 to apply an axial force against rotatable follower 229 proximal end 241 moving rotatable follower 229 in the direction of arrow 221. Simultaneously, spiral cam track 245 applies a rotational force (i.e., a torque-generating force) against followers 243 riding in cam track 245 of the fixed position elongate cam 247. Because rotatable follower 229 is free to rotate in cradle 289, the rotational force applied by cam 247 causes rotatable follower 229 to rotate in the direction of rotational arrow 297 simultaneously with advancement of rotatable follower 229 in the direction of arrow 221. Advancement of cutter carrier 251 and advancement of rotatable follower 229 carried by cutter carrier 251, causes advancement and rotation of cutter 127 for tissue 47 cutting, severing and shearing and tissue sample 59 acquisition.

The process of cutter 127 axial movement and rotation is reversed during the retraction stroke. The retraction stroke loads spring 315 and partially charges biopsy devices 10, 10' for operation as described below. During the retraction stroke, movement of cutter carrier 251 in the direction of arrow 199 is caused by user pulling of charging handles 301, 303 toward housing 11 rear end 23. Indicia 223 (e.g., the word "CHARGE" in FIGS. 1-8, 11-15) may be provided to indicate to a user the direction in which charging handles 301, 303 should be pulled.

During the retraction stroke, cutter carrier distal wall 293 applies the axial force against rotatable follower distal end 239. Simultaneously, spiral cam track 245 applies the rotational force against followers 243 riding in cam track 245 of the fixed position elongate cam 247 in the opposite manner as during the advancement stroke causing rotatable follower 229 and cutter 127 to simultaneously rotate in the direction opposite that of rotational arrow 297. The retracting axial and rotational movement of cutter 127 continues during charging until the respective sear stop surface 328 again engages a cutter carrier stop surface 327, 329 (or 347, 349) compressing spring 315 and retaining cutter carrier 251 in place against the force applied by spring 315.

Thus, exemplary cutter 127, stripper pin 231 and the related components serve as both elements of tissue cutting mechanism 15 and as elements of vacuum generating mechanism 17, as a type of valve which regulates air flow. As illustrated in FIGS. 22-24B, with cutter 127 initially in the retracted or first position and tissue-receiving aperture 53 fully or partially open, the valve is open toward tissue-receiving cavity 42 but is closed at purge port 256 between cutter 127 and stripper pin 231 by purge valve 129. Air is drawn through cutter 127 and tissue-receiving cavity 42 to produce a vacuum drawing tissue 47 through tissue-receiving aperture 53.

As illustrated in FIGS. 34-35, with cutter 127 next in the advanced or second position to cut, sever and shear tissue 47, the valve is opened toward both the tissue-receiving cavity 42 and purge port 256 by automatic operation of purge valve 129. Ambient air flow through purge port 256 between cutter 127 and stripper pin 231 into vacuum chamber 121 and tissue-receiving cavity 42 equalizes pressure throughout.

As illustrated in FIGS. 37-40, with cutter 127 back to the retracted or first position and tissue-receiving aperture 53 again fully or partially open, the valve returns to being open only toward tissue-receiving cavity 42 as purge port 256 is closed by purge valve. A pulse of air is forced through cutter 127 and tissue-receiving cavity 42 to eject tissue sample 59 through tissue-receiving aperture 53.

Exemplary Tissue Ejection and Delay Mechanism

In the examples, tissue sample 59 ejection occurs after operation of tissue cutting mechanism 15 and with biopsy devices 10, 10' removed from the patient. As previously described, user pulling of charging handles 301, 303 in the direction of arrow 199 retracts cutter 127 partially or fully from tissue-receiving aperture 53 and closes purge valve 129. Coordinated user pushing of handle 201 in the direction of arrow 221 advances piston 123 in vacuum chamber 121 to force air to flow from vacuum chamber 121, through air-flow ports 225 into cutter 127 lumen 261 into tissue-receiving cavity 42 toward tissue-receiving aperture 53 to generate a pulse of air which ejects tissue sample 59 through the fully or partially open tissue-receiving aperture 53. This coordinated user pulling and pushing may be facilitated by providing a first spring 125 which has a greater spring force than the spring force of second spring 315. The difference in spring forces allow cutter 127 to retract partially against the greater spring force of first spring 125 to open tissue-receiving aperture 53 while piston 123 can be advanced more fully to compress second spring 315 and to generate the air pulse at tissue-receiving cavity 42. This arrangement allows the air pulse to be generated before the tissue-receiving aperture 53 is opened fully.

Figures 40, 40A:
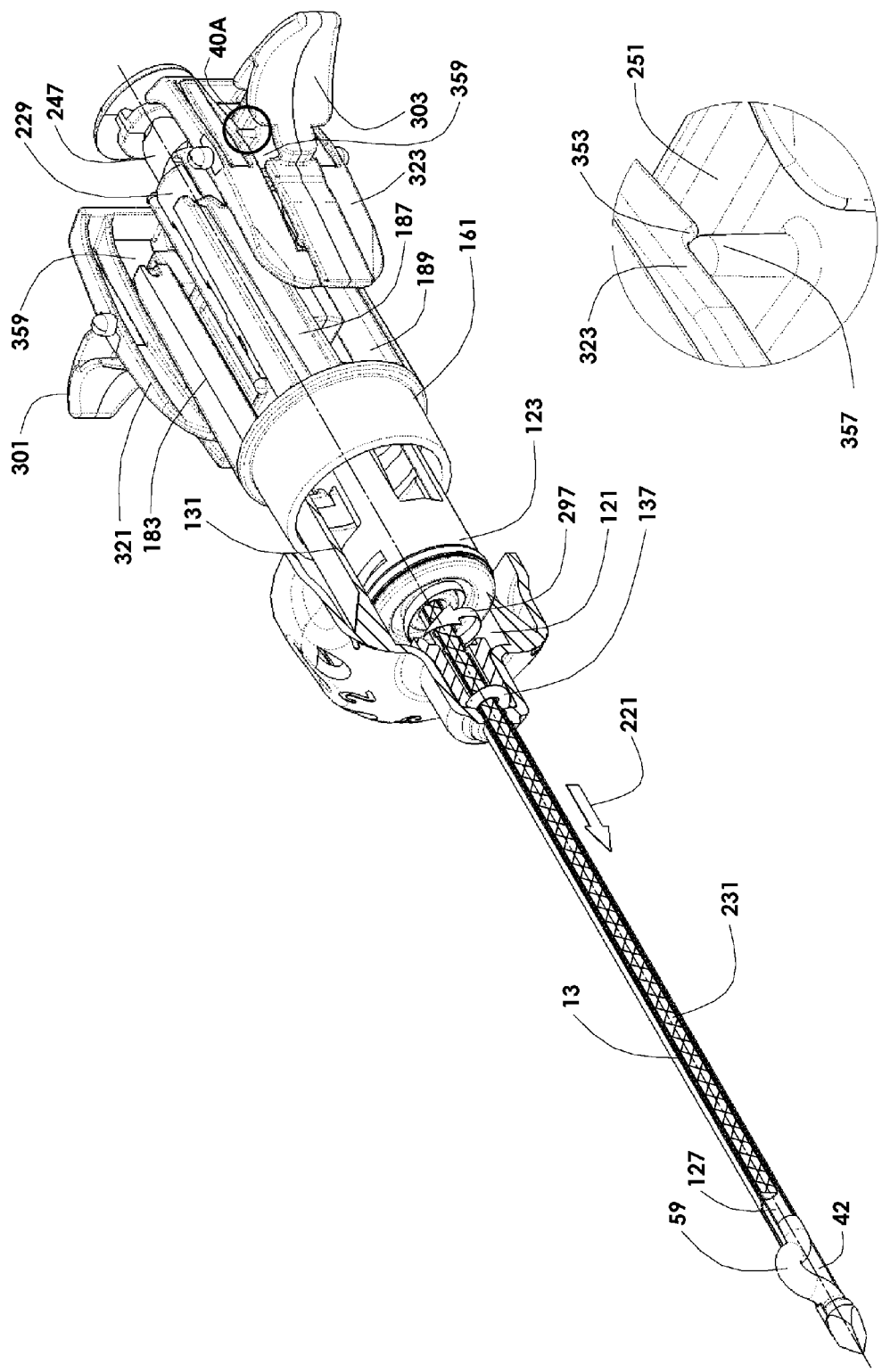
FIG. 40 is a perspective view of the biopsy device of FIG. 1, but during biopsy device charging and tissue sample ejection with certain parts cut away and others removed to facilitate understanding.
FIG. 40A is an enlarged view of exemplary delay mechanism components taken along section 40A of FIG. 40.
Figure 45:
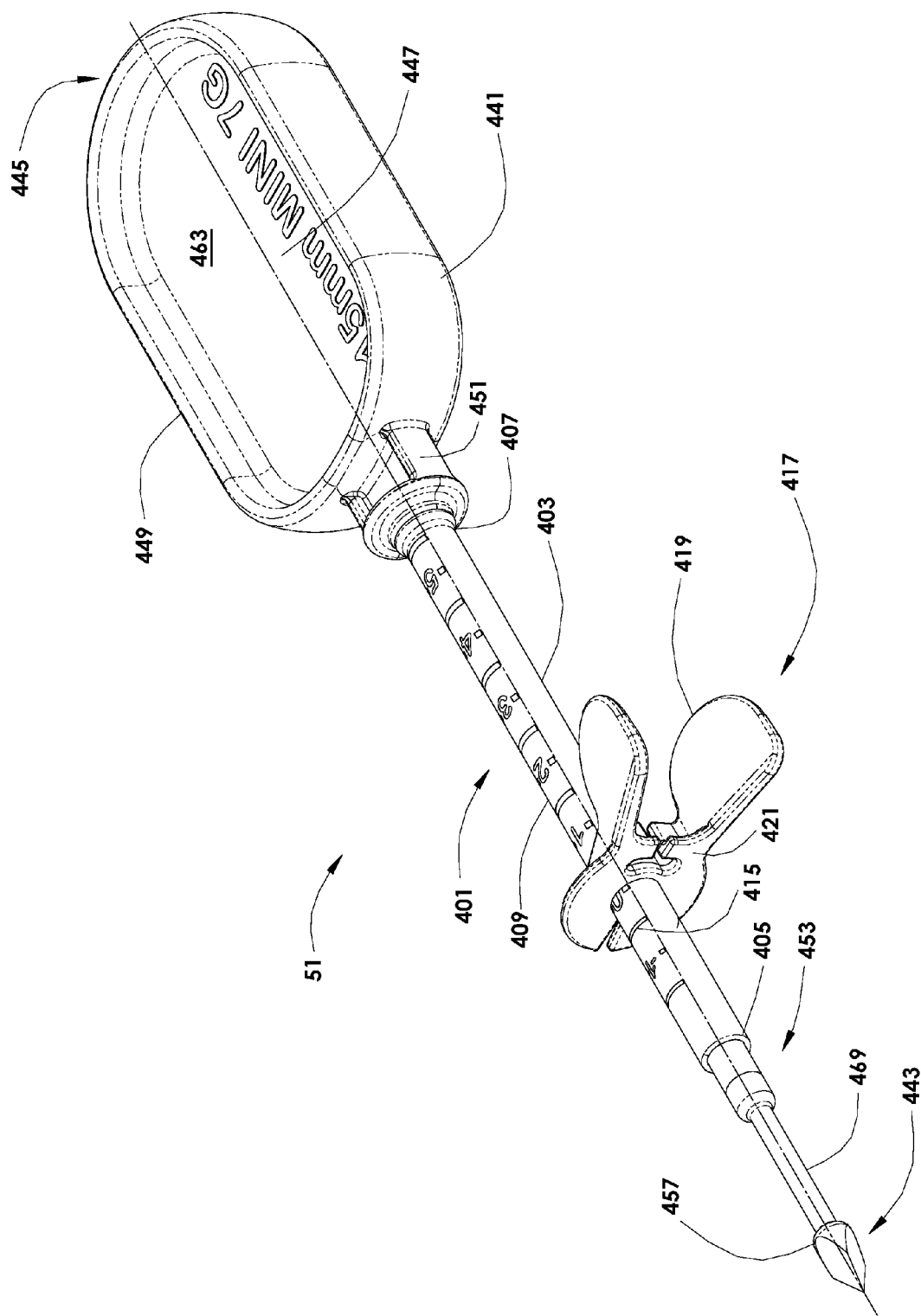
FIG. 45 is a front side perspective view of an exemplary introducer.
Figure 46:
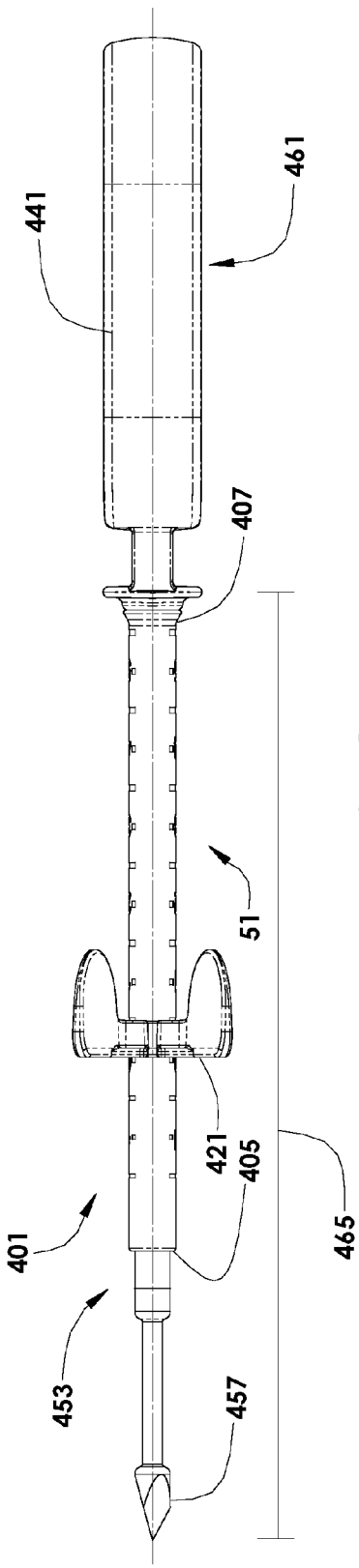
FIG. 46 is a side elevation view of the introducer of FIG. 45.
Figure 47:
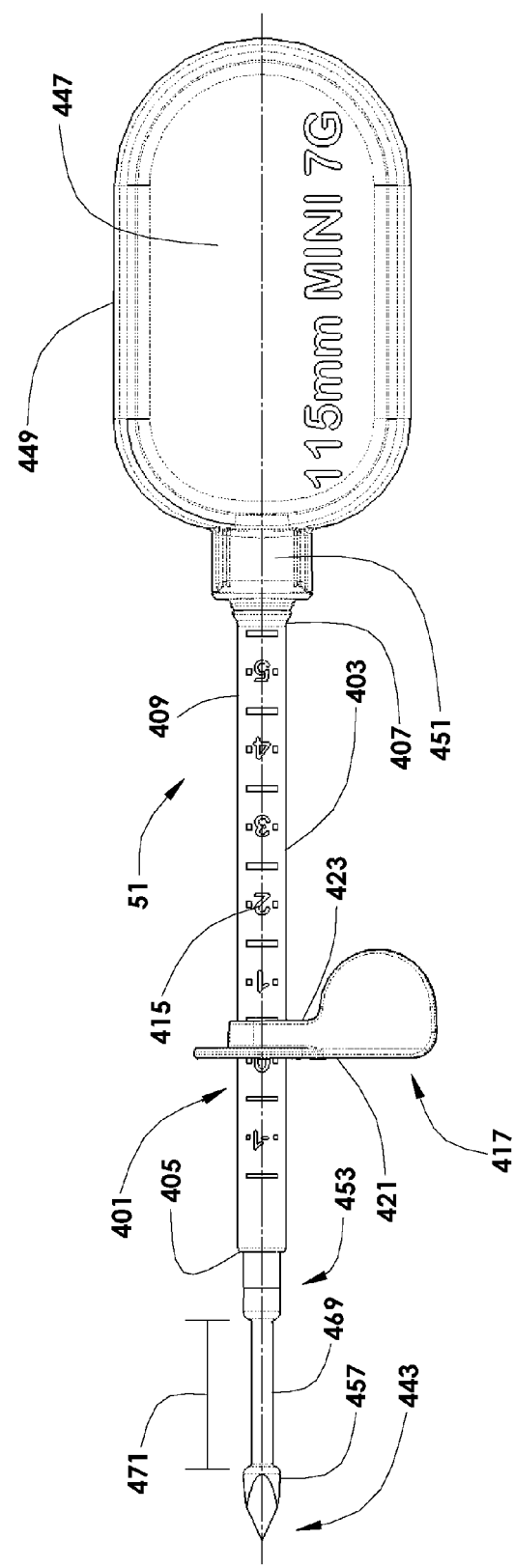
FIG. 47 is a top side plan view of the introducer of FIG. 45.
Figure 48:
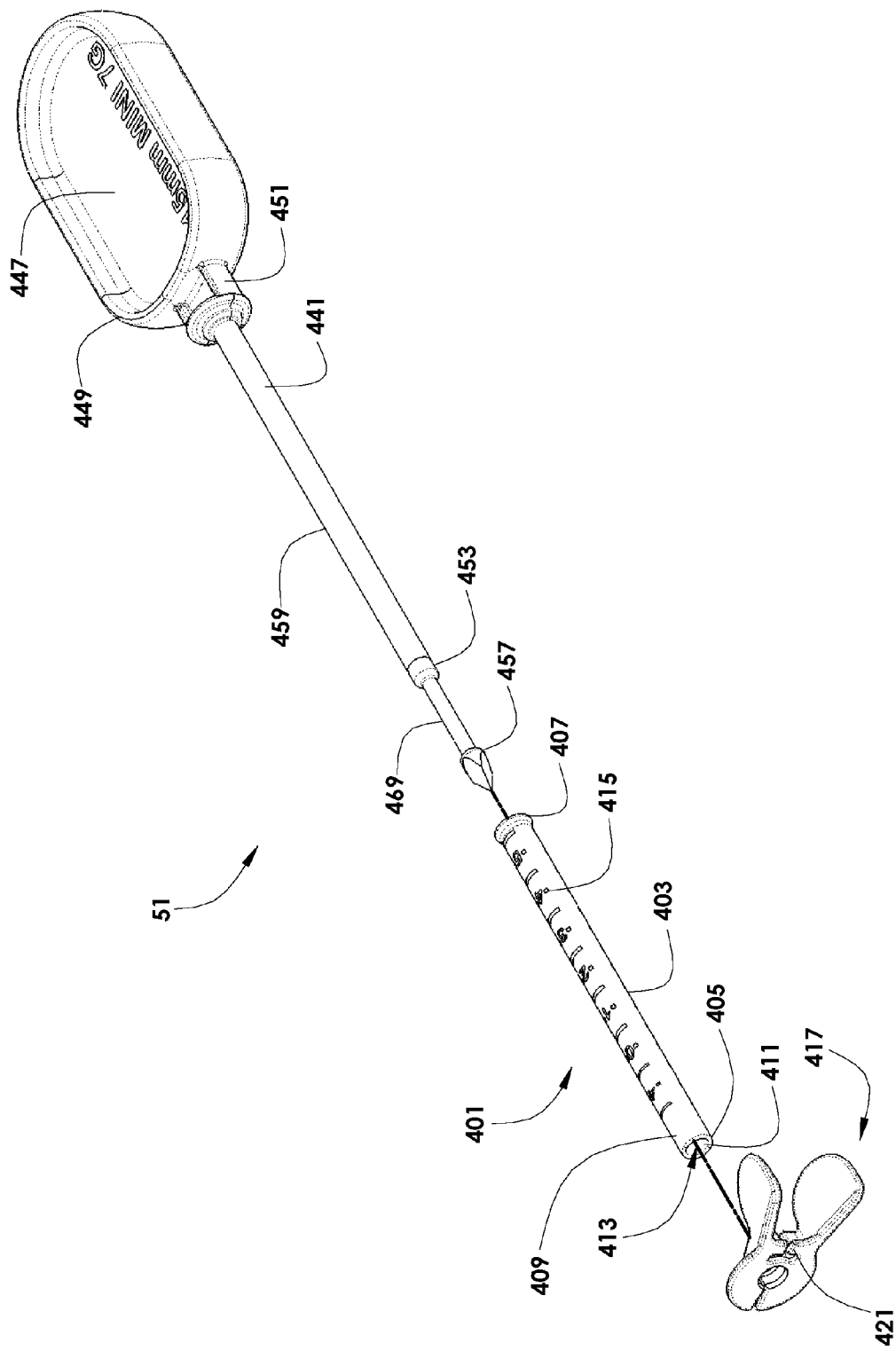
FIG. 48 is an exploded view of the introducer of FIG. 45.

Referring to FIGS. 40, 40A and 41, a delay mechanism may optionally be provided to facilitate ejection of tissue sample 59 from tissue-receiving cavity 42. Exemplary delay mechanism is a type of timing device which coordinates operation of tissue cutting mechanism 15 with operation of vacuum generating mechanism 17 so that retraction of cutter 127 is interrupted, thereby permitting air to be forced from vacuum chamber 121 before complete retraction of cutter 127. Interruption of cutter 127 retraction provides a further opportunity for the pulse of air from vacuum generating mechanism 17 to positively eject tissue sample 59 from tissue-receiving cavity 42 and tissue-receiving aperture 53.

Referring again FIGS. 40-41, exemplary delay mechanism comprises a pair of stops 351, 353 on cutter carrier 251 which extend away from cutter carrier 251 and inward facing stop surfaces 355, 357 on sears 321, 323 which extend into slot 359 through which charging handles 301, 303 extend through sears 321, 323 and out of housing 11. If provided, stop surfaces 355, 357 are contacted by stops 351, 353 during retraction of cutter carrier 251 in the direction of arrow 199 when charging handles 301, 303 are pulled rearward toward housing rear side 23 with a user's fingers.

Cutter carrier 251 stops 351, 353 contact stop surfaces 355, 357 which momentarily increase resistance to retracting movement of cutter carrier 251. This momentary increase in resistance to cutter carrier 251 movement causes the user to increase force applied to handle 201 push surface 219 with the user's thumb to allow handle 201 to be preferentially moved in the direction of arrow 221 relative to retraction of cutter carrier 251 and cutter 127 in the direction of arrow 199. The resistance to cutter carrier 251 retraction provided by stops 351, 353 and stop surfaces 355, 357 is useful to overcome the spring force of first spring 125 which may be relatively greater than the spring force of second spring 315 in embodiments.

The delay mechanism interrupts retraction of cutter carrier 251 momentarily so that cutter 127 partially obstructs tissue-receiving aperture 53 during generation of the air pulse by vacuum generating mechanism 17. Partial obstruction of tissue-receiving aperture 53 by cutter 127 as air is delivered to tissue-receiving cavity 42 may increase the force of the positive air pressure and further serves to direct tissue sample 59 out of optional widened portion 55 of tissue-receiving aperture 53 which provides less resistance to ejection of tissue sample 59.

Force applied by the user against charging handles 301, 303 quickly overcomes the frictional force resisting cutter carrier 251 retraction spreading stop surfaces 355, 377 in the directions of arrows 379, 381 (FIG. 41) enabling cutter carrier 251 to retract until cutter carrier 251 proximal wall 295 contacts cam base 287. Advancement of cutter carrier 251 can then be stopped by engagement of carrier stop surfaces 325, 327 (or stop surfaces 347, 349) with a respective sear stop surface 328 so that cutter carrier 251 is held in the charged state of each biopsy device 10, 10' awaiting a further operational cycle.

Exemplary Depth Guide

Referring to FIGS. 42-48 and 51-56, biopsy devices 10, 10' may optionally be used in conjunction with various accessory devices. Such accessory devices may enhance operation of biopsy devices 10, 10', thereby providing further opportunities for improved patient care.

For example, and as shown in FIGS. 45-48, biopsy devices 10, 10' may optionally be used with a depth guide 401 which is useful to position tissue-receiving aperture 53 at the precise depth proximate the lesion, tumor or other targeted tissue 48 to be acquired as determined, for example, by visualization techniques such as MRI, x-ray imaging or ultrasound imaging. Depth guide 401 is also useful when seeking to reproducibly position tissue-receiving aperture 53 at an identical location in tissue 47 for purposes of acquiring plural tissue samples 59 around cannula 13, for example by rotation of cannula support 29 to locate tissue-receiving aperture 53 at one or more different indexed angular positions relative to housing 11 as illustrated in FIGS. 44A-44D and described previously.

Exemplary depth guide 401 preferably comprises a sleeve which is coaxial with axis 19 and concentric with and around cannula 13 when in use. Exemplary depth guide 401 comprises a tubular body 403, first and second opposed ends 405, 407, an outer surface 409 and an inner surface 411 defining a cylindrical passageway 413. First end 405 may be considered a distal end because it is furthest from the user during use while second end 407 may be considered a proximal end. Exemplary cylindrical passageway 413 is sized to permit depth guide 401 to be received by an introducer 51, 51' or a cannula 13, both when cannula 13 initially receives depth guide 401 and when cannula 13 must be reinserted into depth guide 401 left in tissue 47 for purposes of acquiring a multiple tissue samples 59 from the same lesion, tumor or other targeted tissue 48. Depth guide 401 has a length dimension which preferably does not obstruct tissue-receiving aperture 53. Contact between biopsy device 10, 10' neck 35 and depth guide 401 second, or proximal, end 407 permits biopsy devices 10, 10' to be located in depth guide 401 in a reproducible, and identical position relative to depth guide 401. Depth guide 401 second, or proximal, end 407 may be widened to prevent depth guide indicator 417 from sliding off depth guide 401. Widening of proximal end 407 may also provide more positive contact with neck 35 of biopsy device 10 or with introducer 51, 51' as force is applied by the user during insertion of the biopsy device 10 and depth guide 401 or during insertion of introducer 51, 51' and depth guide 401 into tissue 47.

Tubular body 403 outer surface may include a scale 415 comprising a series of marks along outer surface 409 at determinate distances for purposes of depth measurement. The marks of scale 415 may, for example, be spaced apart at 1 centimeter increments. Indicia, such as a number associated with each mark, may be included as part of scale 415 as illustrated in FIGS. 48-50 and 54-59.

Referring now to FIGS. 45-48, 50-51 and 54-59, a depth guide indicator 417 may be used with depth guide 401 to positively indicate the desired insertion depth of an introducer 51, 51 ' and a biopsy device 10, 10' and to provide a positive stop limiting insertion of a biopsy device 10, 10' into tissue 47 past the desired depth. Referring specifically to FIGS. 50-51, depth guide indicator 417 comprises a unitary body 419, distal and proximal sides 421, 423, a clamp 425 defining an aperture 427 for attachment around depth guide 401 and a clamp opening 429, internal spring 431, spreaders 433, 435 and stops 437, 439. Unitary body 419 is preferably a single piece of material. Plastic is a preferred material due to material properties and cost considerations.

Depth guide indicator 417 is positioned on depth guide 401 by pressing spreaders 433, 435 together with the user's fingers. Contact between stops 437, 439 prevents excessive travel of spreaders 433, 435 which could damage internal spring 431. Spreaders 433, 435 may have a butterfly-type design with wide surface contact areas for finger pushing as illustrated in FIGS. 50-51 and 54-59. Clamp 425 is widened increasing the size of clamp opening 429 by pushing together of spreaders 433, 435 so that depth guide 401 can be received in clamp aperture 427. Aperture 427 is undersized relative to depth guide 401 tubular body 403 to permit clamp 425 to securely attach depth guide indicator to depth guide tubular body 403 through force applied by internal spring 431 when spreaders 433, 435 are released.

Pressing together of spreaders 433, 435 causes internal spring 431 to deflect, thereby loading internal spring 431. Internal spring 431 exerts a spring force as it attempts to return to its original unloaded position following deflection. The spring force causes clamp 425 to exert a force on depth guide 401 tubular body 403 securing depth guide indicator 417 to depth guide 401. Depth guide indicator 417 can be easily positioned on depth guide 401 by pressing spreaders 433, 435 together to release the force applied by clamp 425 and spring 431 followed by sliding depth guide indicator 417 to the desired position on depth guide 401. Preferably, distal side 421 of depth guide indicator 417 faces tissue 47. Distal side 421 may be planar to permit precise alignment of planar distal side 421 with scale 415. Distal side 421 contacts an external surface of tissue 47 to stop further movement of depth guide into tissue 47 thereby correspondingly controlling the insertion depth of a cannula 13 received in depth guide 401 to accurately locate tissue-receiving aperture 53 proximate the same lesion, tumor or other targeted tissue 48.

Exemplary Introducers

Referring next to FIGS. 45-49 and 56-59, introducers 51, 51' are preferably used with depth guide 401 for purposes of achieving the desired depth of tissue-receiving aperture 53 as described above. Exemplary introducers 51, 51' share the same structure and operation, except as noted herein. For convenience and brevity, common reference numbers are used to identify like parts and features of introducers 51, 51'. Introducers 51, 51' are not required to be used with depth guide 401. Introducers 51, 51' are used to make a tunnel 49 in the tissue 47 before insertion of cannula 13. The cannula 13 is then inserted more easily into tunnel 49 to position tissue-receiving aperture 53 adjacent the tissue 47 to be acquired. Introducers 51, 51' are preferably used with blunt tip end 45' biopsy device 10' which is not intended for self-tunneling as is biopsy device 10 with its sharp tip end 45.

An application for introducers 51, 51' is in connection with visualization techniques using a visualization modality to position cannula 13 and tissue-receiving aperture 53 in tissue 47. For example, introducers 51, 51' for use with MRI may be made of non-magnetic metal materials and plastics. Persons of skill in the art will appreciate that ferrous and magnetically-attracted metals cannot be used with MRI due to the strong magnetic field created during MRI procedures. Once the introducer 51, 51' is properly positioned using MRI visualization, the introducer 51, 51' is removed and the biopsy procedure performed, preferably using biopsy device 10' outside the MRI machine bore. Therefore, introducers 51, 51' offer an opportunity to avoid adverse consequences should a biopsy device including materials attracted to a magnet be used in conjunction with MRI visualization.

Referring to FIGS. 45-49, introducers 51, 51' have a body 441, distal and proximal ends 443, 445, a handle 447 having a gripping rib 449, a neck 451 extending distally from handle 447 and a lance 453 extending distally from neck 451 and defining an axis 455. In the examples, lance 453 may terminate in a sharp end tip element 457, 457' which may be a trocar-type end element 457, 457' as illustrated or another type of end element capable of self-tunneling of lance 453 into tissue 47. Tip element 457, 457' may be joined to lance shank 459 by threaded engagement, adhesive, over molding as described previously, or other suitable means known to persons of skill in the art.

Exemplary handle 447 has first and second sides 461, 463. Gripping rib 449 extends away from each side 461, 463 around a periphery of handle 447 as an aid in gripping of handle 447 by the user. Exemplary handle 447, neck 451 and lance shank 459 may be a unitary part which may be of, for example, plastic material. Sharp end tip element 457, 457' should be of a material which is not attracted to a magnet in applications in which introducer 51, 51' is to be used with MRI.

Figure 58:
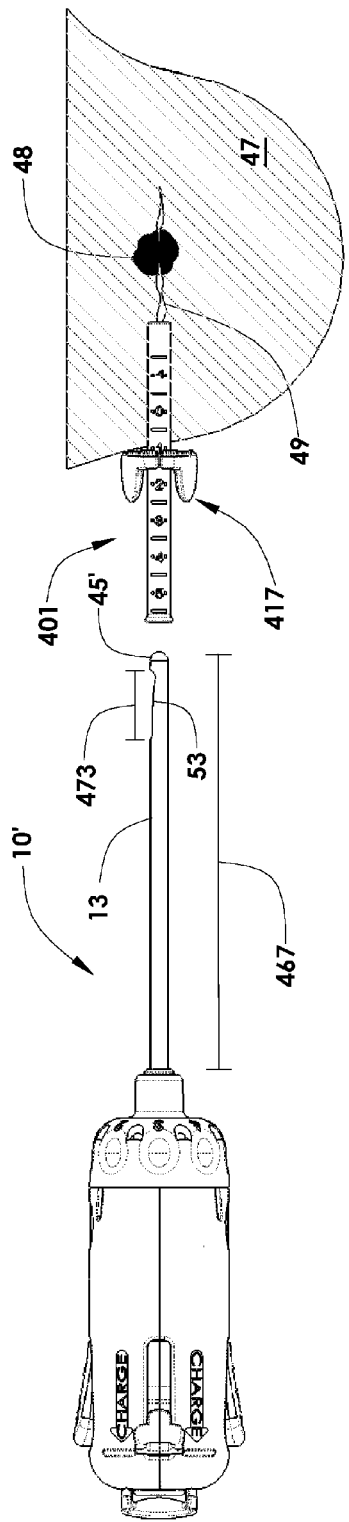
FIG. 58 is a schematic illustration of the biopsy device of FIG. 11, before insertion into tissue, which is shown as breast tissue.
Figure 59:
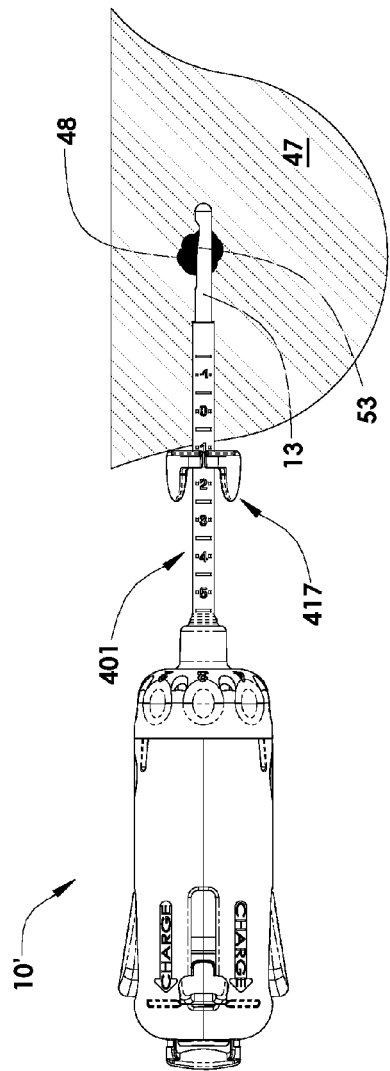
FIG. 59 is a schematic illustration of the biopsy device of FIG. 11, after insertion into the tissue.

Introducer 51, 51' is preferably sized for use with a correspondingly sized biopsy device 10' (or biopsy device 10) so that cannula 13 can be positioned in tissue 47 at a location identical to that of introducer 51, 51'. In such embodiments, lance 453 preferably has a length dimension 465 (FIG. 46) from neck 451 to distal end 443 which is identical to a length dimension 467 of cannula 13 from neck 35 to distal end 31 (FIG. 58). Further, exemplary sharp tip element 457, 457' may comprise a locator region 469 (FIG. 47) proximal distal end 443 which has a length dimension 471 which is identical to a length dimension 473 (FIG. 58) of tissue-receiving aperture 53 of cannula 13 and is located at a position along lance 453 which is identical to the position of tissue-receiving aperture 53 on cannula 13.

Figure 49:
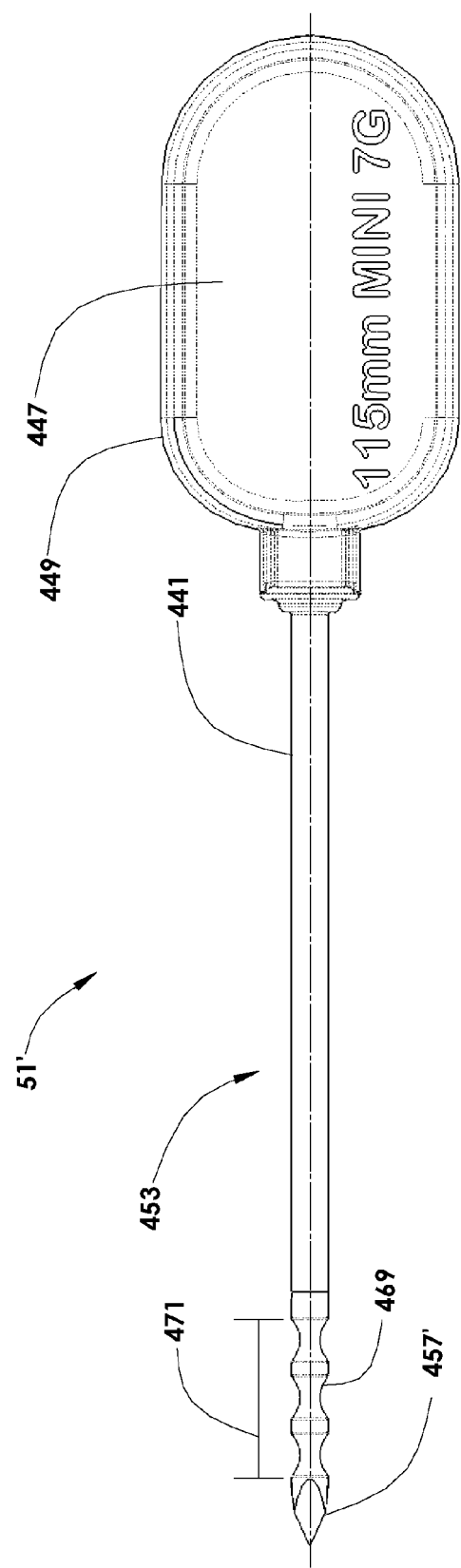
FIG. 49 is a top side plan view of a further exemplary introducer.

Locator region 469 preferably comprises a geometric shape or other marker rendering locator region 469 capable of being visualized by means of an MRI or other visualization procedure. By way of example only, locator region 469 may comprise a narrowed portion of lance 453 tip element 457, 457' as illustrated in the examples of FIGS. 45-48 or a wave-form portion of lance 453 comprising a series of concentric grooves that would correspond to the distal 55, medial 56, proximal 57 locations of tissue-receiving aperture 53 (FIG. 20A) as illustrated in the example of FIG. 49.

Therefore, and by way of example only, a 115 mm introducer lance 443 would be used in biopsy procedures with a 115 mm cannula 13 and the use of an identical length lance 443 and cannula 13 would enable locator region 469 and tissue-receiving aperture 53 to be located at the identical position within tissue 47. Persons of skill in the art will recognize that introducer lance 443, cannula 13, locator region 469 and tissue-receiving aperture 53 may be of other dimensions.

Figure 56:
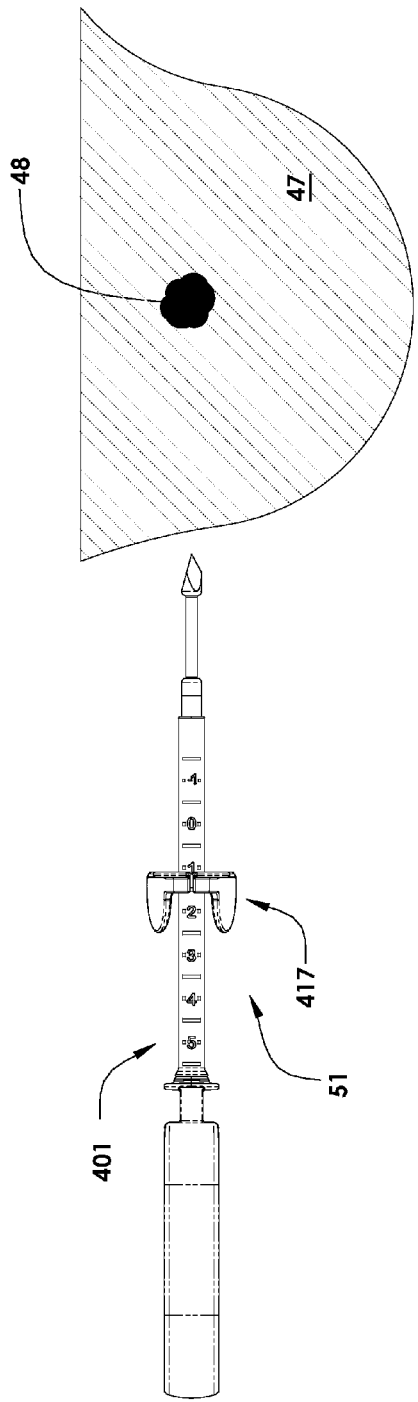
FIG. 56 is a schematic illustration of the introducer of FIG. 45, before insertion into tissue, which is shown as breast tissue.
Figure 57:
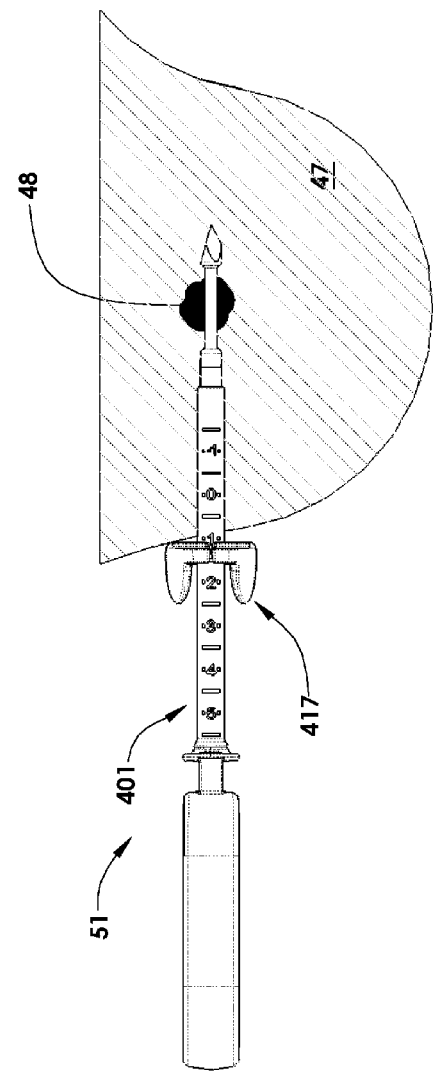
FIG. 57 is a schematic illustration of the introducer of FIG. 45, after insertion into the tissue.

As shown in FIGS. 45-48 and 56-59, introducers 51, 51' are preferably used with depth guide 401 as previously described and as illustrated in connection with biopsy device 10. Exemplary depth guide 401 cylindrical passageway 413 is sized to permit depth guide 401 to be received by lance 453 and by cannula 13 once lance 453 is removed from depth guide 401. Depth guide 401 second, or proximal, end 407 contacts introducer 51, 51' neck 451 in the same manner as depth guide 401 second end 407 contacts neck 35 of a biopsy device 10, 10'. Depth guide 401 is carried with lance 453 as lance 453 is inserted into tissue 47 to the site of the lesion, tumor or other targeted tissue 48 to be acquired as illustrated in FIGS. 57-58. Introducer 51, 51' is then removed leaving depth guide 401 in tissue 47. Cannula 13 is then inserted through depth guide 401. As previously described, cannula 13 and lance 443 have an identical length and tissue-receiving aperture 53 and locator region have an identical length and position along a respective cannula 13 or lance 443. Therefore, insertion of cannula 13 into depth guide 401 in tissue 47 will locate tissue-receiving aperture 53 in a position identical to that of introducer 51, 51' locator region 469 for purpose of tissue 47 acquisition.

Further, and as illustrated in FIGS. 54-57, introducer 51, 51' may be used with both depth guide 401 and depth guide indicator 417 in the same manner as previously described. Depth guide indicator 417 is particularly useful if depth guide 401 remains in tissue 47 after withdrawal of introducer 51, 51' because depth guide indicator 417 assists in keeping depth guide 401 in place in tissue 47 without movement.

Exemplary Operation of the Biopsy Devices

Operation of exemplary biopsy devices 10, 10' will now be described. As noted above, biopsy device 10 includes a self-tunneling sharp end tip element 45 which may be inserted into tissue 47 and used to cut, sever, shear and acquire a tissue sample 59 without first making a tunnel 49 in the tissue 47 with an introducer, such as introducer 51, 51' (FIGS. 45-49). Also as noted above, biopsy device 10 is well-suited for use in biopsy procedures in which biopsy device 10 is guided with assisted visualization, such as by means of ultrasound imaging, x-ray imaging or the like, to position tissue-receiving aperture 53 adjacent the lesion, tumor or other targeted tissue 48 to be acquired.

As further noted above, biopsy device 10' is most preferably used in combination with an introducer, such as introducers 51, 51'. Introducers 51, 51' may be made of materials which are not attracted to a magnet enabling use with assisted visualization procedures such as MRI. Biopsy device 10' may also be guided by means of ultrasound imaging, x-ray imaging or the like. Also as previously noted, it is expected that each of exemplary biopsy devices 10, 10' may be used in connection with assisted visualization procedures which will exist as technology advances.

Biopsy devices 10, 10' of the preferred embodiments shown and described herein represent manually actuated, spring powered devices. Manual actuation of exemplary dual trigger mechanisms 93, 95 (simultaneously or consecutively) causes sequential operation of spring 125 to power vacuum generating mechanism 17 followed by automatic operation of spring 315 to power tissue cutting mechanism 15. Tissue 47 drawn by vacuum generating mechanism 17 into tissue-receiving aperture 53 and tissue-receiving cavity 42 within cannula 13 lumen 41 is cut, severed and sheared by tissue cutting mechanism 15 resulting in acquisition of a tissue sample 59.

In the examples, spring-driven operation of vacuum generating device 17 and tissue cutting mechanism 15 can be very rapid depending on the type of biasing device and biopsy device design. This arrangement permits implementation of biopsy device 10, 10' embodiments which acquire the tissue sample 59 in an almost instantaneously manner. Rapid tissue acquisition is an advantage relative to biopsy devices which are required to operate in a relatively slower manner.

Further, biopsy device 10, 10' embodiments acquire a histologically significant tissue sample 59 in each operational cycle, potentially reducing the number of biopsy procedures needed and improving the quality of patient care. An adequate tissue sample 59 can be obtained because of the strong vacuum provided by vacuum generating mechanism 17 and the positive cutting, severing and shearing action provided by tissue cutting mechanism 15.

In examples of operation, biopsy devices 10, 10' may be provided to the user in either a charged or discharged (i.e., uncharged) state. In certain circumstances, it may be desirable to supply biopsy device 10, 10' sterilized in a charged state and ready for use. For example, biopsy device 10, 10' may be sterilized and provided in a sealed container, such as a sealed bag (not shown), charged and ready for use. By way of further example, biopsy devices 10, 10' could be provided in a sealed container in an discharged state.

As previously noted, exemplary biopsy devices 10, 10' are illustrated in the charged state ready for use in FIGS. 4-5, 7, 22-25, 52-55 and 58-59. The charged state of biopsy devices 10, 10' is visually apparent because tissue-receiving aperture 53 is fully or partially open, charging handles 301, 303 are retracted toward rear end 23 of housing 11 and handle 201 is advanced within housing 11 such that runners 207, 209 are largely within housing 11 and push surface 219 is near rear end 23 of housing 11.

Also as previously noted and as illustrated in FIGS. 23-24A, spring 125 powering vacuum generating mechanism 15 is compressed and applies a force in the direction of arrow 199 against spring seat 181 of piston carrier 161 biasing piston carrier 161 in the direction of arrow 199 and toward housing 11 rear end 23. Sears 101, 103 contact and retain piston carrier 161 against the force of spring 125, specifically by contact between sear 101, 103 distal end 117 bearing against spring seat 181 proximal side 193 in the examples (FIGS. 23-23A). In such position, piston 123 of piston carrier 161 is advanced distally into vacuum chamber 121 such that piston face 157 is near proximal end 147 of seal retainer 139 while annular seal 163 forms an air-tight seal between piston 123 and inner wall 131 of vacuum chamber 121 (FIGS. 24-24A).

At distal end 143 of seal retainer 139, annular seal 137 forms an air-tight seal preventing air from passing into cannula 13 lumen 41 through gap 159 between cannula 13 inner surface 39 and cutter 127 outer surface 153 and sealing the distal end of vacuum chamber 121. Vacuum chamber 121 is further sealed by annular seal 163 seated on piston 123 and by annular seal 179 between piston stem 165 and seal cap 178 bearing against cutter outer surface 153. Lastly, vacuum chamber 121 is sealed by purge valve 129 in its closed state (FIG. 24B) in which annular seal 265 forms an air-tight seal against stripper pin 231 preventing air from moving through purge port 256 and into cutter 127 lumen 261 within the gap 283 between cutter 127 inner surface 259 and stripper pin 231. Seal 265 therefore prevents air from entering vacuum chamber 121 through cutter 127.

Also in the exemplary charged state and as illustrated in FIGS. 22-23A, spring 315 powering tissue cutting mechanism 15 is compressed and applies a force in the direction of arrow 221 against spring seat 313 of cutter carrier 251 biasing cutter carrier 251 in the direction of arrow 221 and toward housing 11 front end 21. Sears 321, 323 contact and retain cutter carrier 251 against the force applied by spring 315, specifically by contact between sear 321, 323 stop surface 328 and cutter carrier stop surfaces 325, 327 (FIGS. 22, 26-26A) or cutter carrier stop surfaces 347, 349 (FIGS. 42-43). In such position, cutter 127 is retracted within cannula lumen 41 so that tissue-receiving aperture 53 is fully or partially unobstructed by cutter 127 outer surface 153, cutter distal end 253 or optional inscribed edge 262 of cutter 127. Rotatable follower 229 is fully meshed with cam 247 with followers 243 in spiral cam track 245. Stripper pin 207 extends through cutter 127 lumen 261 as previously described.

Figure 52:
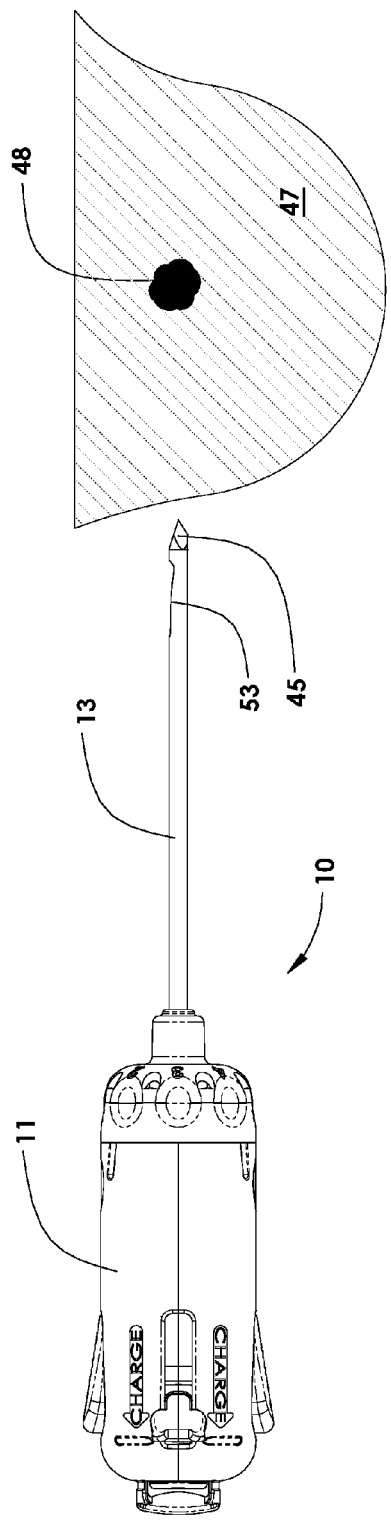
FIG. 52 is a schematic illustration of the biopsy device of FIG. 1, before insertion into tissue, which is shown as breast tissue.
Figure 53:
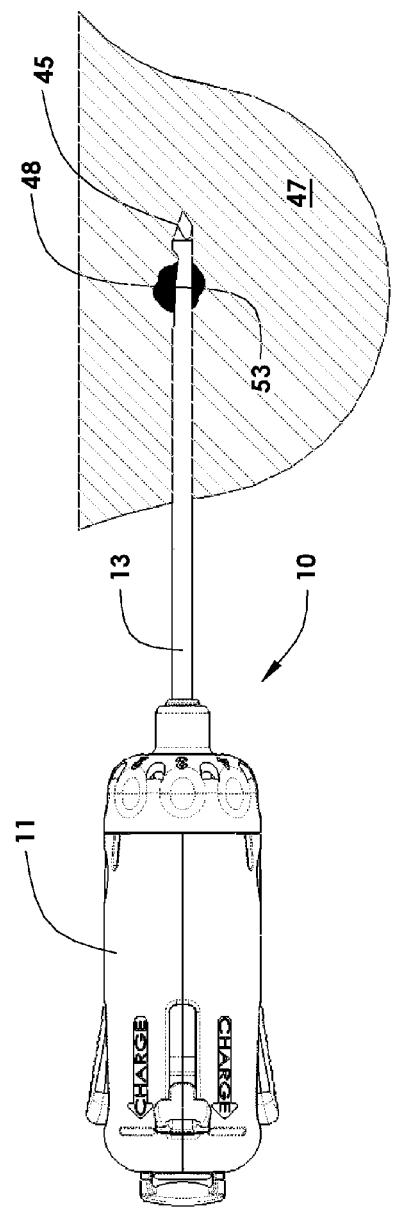
FIG. 53 is a schematic illustration of the biopsy device of FIG. 1, after insertion into the tissue.

For biopsy device 10 and as shown in the schematic illustrations of FIGS. 52-53, the user inserts the sharp tip end 45 into tissue 47 (e.g., breast or other tissue) so that tissue-receiving aperture 53 is adjacent the lesion, tumor or other targeted tissue 48 to be acquired. If multiple tissue 47 samples (e.g., sample 59) are to be taken from the same insertion site, cannula support 29 may optionally be rotated to an indexed position indicated by indicia 81 with the user's fingers against optional grips 83 (e.g., FIGS. 44A-44D) before a subsequent insertion or insertions into tissue 47.

Biopsy device 10 may be used with depth guide 401 and depth guide indicator 471 as illustrated schematically in FIGS. 54-55 should it be necessary to acquire multiple tissue samples (e.g., sample 59) from the same site. Use of depth guide 401 and depth guide indicator 471 assist the user in reproducibly positioning cannula 13 at an identical position within tissue 47 so that tissue-receiving aperture 53 can be returned to the identical position or indexed to a different position for tissue 47 acquisition as previously described.

For biopsy device 10' and as shown in the schematic illustrations of FIGS. 56-57, the user first locates the introducer 51, 51', depth guide 401 and depth guide indicator 417 so that locator region 469 is adjacent to the lesion, tumor or other targeted tissue 48 to be acquired. The introducer 51, 51' is then removed leaving the depth guide 401 in place within tissue 47. Next, cannula 13 may be inserted through depth guide 401 with tissue-receiving aperture 53 adjacent the lesion, tumor or other targeted tissue 48 to be acquired.

Biopsy devices 10, 10' are now in position ready for use.

FIGS. 60A-60L schematically illustrate tissue 47 acquisition with blunt tip end 45' cannula variant of biopsy device 10'. However, the operations indicated by FIGS. 60A-60L apply equally with respect to the sharp tip end 45 cannula 13 variant illustrated in connection with biopsy device 10 and such figures and the exemplary explanation of operation are incorporated by reference with respect to exemplary biopsy device 10.

Figure 60A:
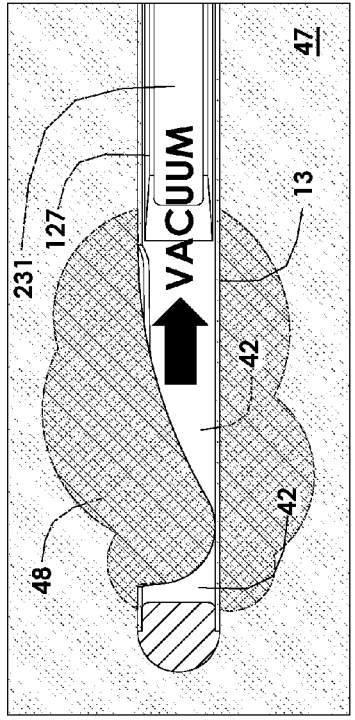
FIG. 60A is schematic illustration showing portions of the exemplary biopsy device of FIG. 11 inserted into tissue, before discharge of the biopsy device.
Figure 60B:
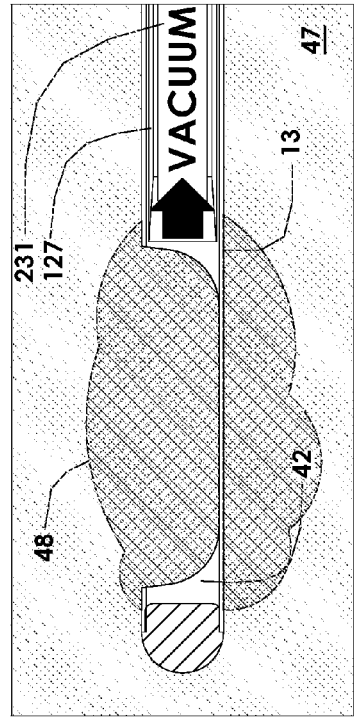
FIGS. 60B-60F are schematic illustrations showing the exemplary biopsy device of FIG. 11 during discharge and tissue acquisition.
Figure 60C:
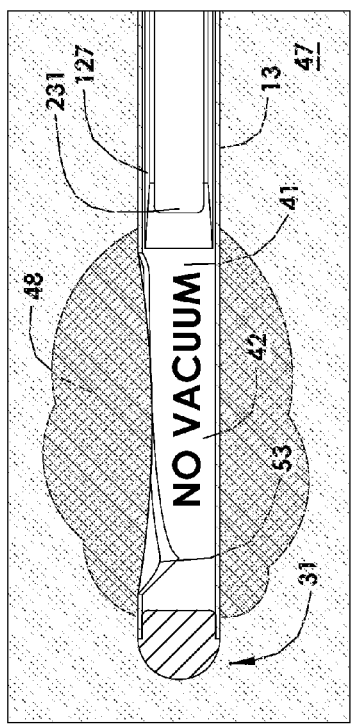
Figure 60D:
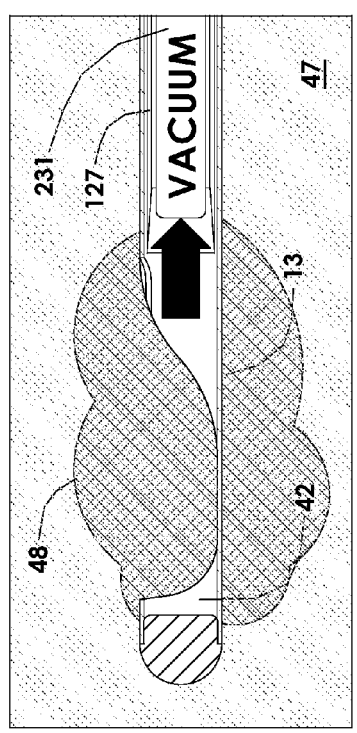
Figure 60E:
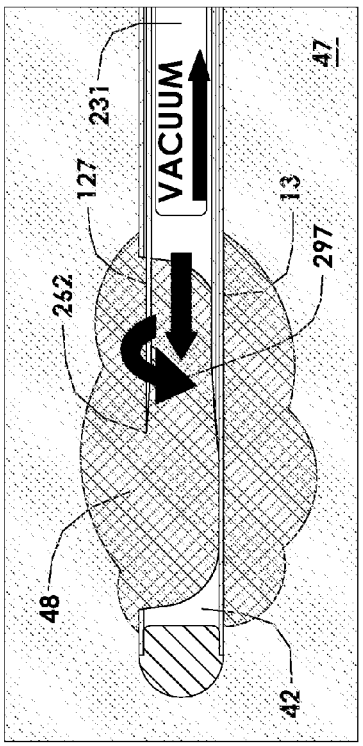

Referring first to FIG. 60A, such figure represents the position of cannula 13 inserted into tissue 47 before operation and discharge of each exemplary biopsy device 10, 10'.

Next and illustrated by FIGS. 23-23A, 26, 27 and 28A, operation of biopsy devices 10, 10' begins by pressing trigger buttons 97, 99. Pressing trigger buttons 97, 99 moves sear 101, 103 proximal end 109 inward (e.g., FIG. 23A direction of arrow 111 for proximal end 109 of sear 101) moving each sear 101, 103 distal end 117 outward and out of contact with spring seat 181 proximal side 193. Movement of each sear distal end 117 out of contact with spring seat proximal side 193 triggers operation of vacuum generating mechanism 17.

As shown in FIGS. 26, 27 and 28-28B, vacuum generating mechanism 17 operates to produce a vacuum as spring 125 retracts piston carrier 161 axially in the direction of arrow 199. In the examples, piston carrier 161 is moved very rapidly by spring 125 once sears 101, 103 release piston carrier 161. Piston 123 on piston carrier 161 retracts axially toward housing 11 rear end 23 within vacuum chamber 121 drawing air into vacuum chamber from cannula lumen 41 producing a vacuum across tissue-receiving aperture 53 and tissue-receiving cavity 42 as air is drawn through cutter 127 lumen 261 around stripper pin 231, through air-flow ports 225 and into expanding vacuum chamber 221 with purge valve 129 closed. In the examples, a vacuum sufficiently strong to draw tissue 47 into tissue-receiving cavity 42 is produced by the rapid spring-driven 125 movement of piston 123 within vacuum chamber 121.

The air flow directional arrows of FIGS. 28-28B indicate the locations and directions of air movement toward and into vacuum chamber 121 caused by retraction of piston 123 in the direction of arrow 199 toward housing rear side 23. Purge valve 129 annular seal 265 blocks air flow through purge port 256 of cutter 127. Air between annular seal 265 and vacuum chamber 121 is drawn toward vacuum chamber 121 as indicated by the air flow directional arrows. Tissue 47, such as the lesion, tumor or other targeted tissue 48 to be acquired, is inducted by the vacuum into tissue-receiving aperture 53 and into tissue-receiving cavity 42 as illustrated schematically in FIGS. 60B-60E.

If provided, tapered tissue-receiving aperture 53 illustrated in FIG. 20A provides an opportunity to acquire a more uniform and substantial tissue sample 59 by preferentially inducting tissue 47, 48 through widened proximal end 55 of tissue-receiving aperture 53. As described, this limits possible obstruction of cannula 13 lumen 41 proximate tissue-receiving aperture 53 narrowed proximal end 57 which could interfere with production of the vacuum across tissue-receiving aperture 53 resulting in an inadequate tissue sample 59 and disadvantageously requiring additional biopsy procedures.

As the vacuum is produced by vacuum generating mechanism 17, piston carrier 161 continues movement toward housing 11 rear end 23 in the direction of arrow 199. As illustrated by comparison of FIGS. 22 and 26 with FIGS. 32-32A, this retraction of piston carrier 161 in the direction of arrow 199 causes attached handle 201 to extend further out of housing 11 rear end 23 and further causes each cam surface 333 of cam posts 183-189 to approach and contact a respective sear 321, 323 proximal end 331. Contact between each cam surface 333 and a respective sear proximal end 331 moves each sear 321, 323 proximal end 331 outward and further moves sear distal end 329 and stop surface 328 inward and out of contact with cutter carrier stop surfaces 325, 327 (FIGS. 32-32A) or stop surfaces 347, 349 (FIGS. 42-42A). Movement of each sear stop surface 328 out of contact with the respective cutter carrier 251 stop surface 325, 327 or 347, 349 in turn triggers operation of tissue cutting mechanism 15.

Figure 60F:
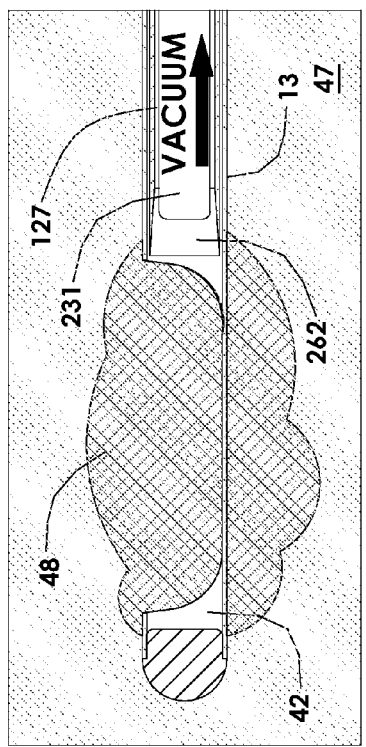
Figure 60G:
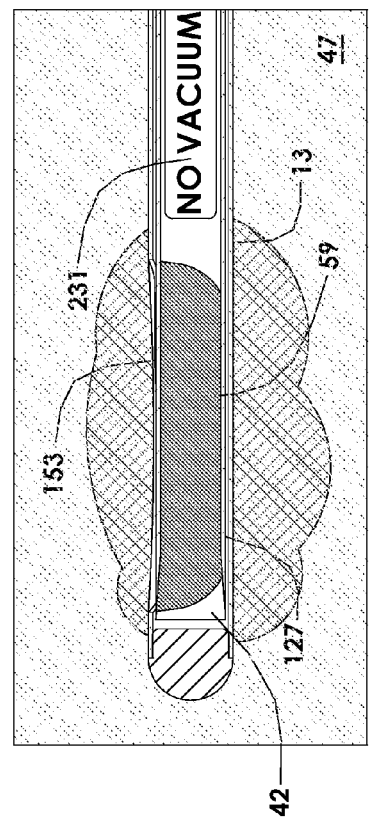
FIG. 60G is a schematic illustration showing the exemplary biopsy device of FIG. 11 after discharge and tissue acquisition.

As shown in FIGS. 32-36 tissue cutting mechanism 15 operates as spring 315 moves cutter carrier 251 axially in the direction of arrow 221. In the examples, cutter carrier 251 and cutter 127 and follower 229 supported thereby are moved very rapidly by spring 125 once sears 321, 323 release cutter carrier 251. Charging handles 301, 303 advance in slots 305, 307 as cutter carrier 251 is advanced by spring 315. The advancement stroke of cutter 127 and cutter carrier 251 preferably commences as vacuum continues to be generated by vacuum generating mechanism 17 as illustrated in FIG. 60F.

Cutter 127 is advanced in the direction of arrow 221 across tissue-receiving aperture 53 while being rotated in the direction of rotational arrow 297 by simultaneous co-action of axial movement of cutter carrier 251, rotatable follower 229 and spiral cam 247 as previously described. In the examples, advancement and rotation of cutter 127 by spring 315 is sufficiently powerful to cut, sever and shear tissue 47 inducted into cannula 13 lumen 41 and tissue-receiving cavity 42 through tissue-receiving aperture 53. Annular seals 137, 163 and 265 continue to maintain an air-tight seal, sealing vacuum chamber 121 as cutter carrier 127 begins to be advanced and rotated. Purge valve 129 annular seal 265 continues to maintain an air-tight seal of vacuum chamber 121 as rotatable follower 229 rotates within cutter carrier 251 cradle 289 and annular seal 265 carried by seal trap 263 is advanced and rotated while maintaining sealing contact with stripper pin 207.

Full cutter 127 advancement occurs when axial movement of cutter carrier 251 is stopped by stops 344, 345 (FIGS. 2-3). Tissue sample 59 is cut, severed and sheared by cutter 127 and the preferred inscribed edge 262. In the examples, the acquired tissue sample 59 would fill cutter 127 lumen 261 providing a substantial sample for purposes of histological evaluation. Stripper pin 231 stop surface 279 blocks movement of tissue sample 59 within lumen 261 past stop surface 279, preventing tissue sample 59 from being pulled through lumen 261 past stripper pin stop surface 279 and proximally into cutter 127 where tissue sample 59 would become inaccessible.

As previously described, the vacuum created by vacuum generating mechanism 17 can create forces which hold tissue 47 surrounding cannula 13 tightly against cannula 13 outer surface 37, particularly at the junction of tissue-receiving aperture 53 and cutter 127 outer surface 153. These forces can exist even though tissue sample 59 has been acquired and is separated from surrounding tissue 47.

As shown in FIGS. 34-34A, in the advanced position of cutter 127, air-flow ports 225 straddle annular seal 137 and purge valve 129 annular seal 265 carried by follower 229 becomes aligned with annular notch 281 around stripper pin 231 to automatically open purge valve 129 permitting pressure equalization within biopsy devices 10, 10'. Purge valve 129 is open because annular seal 265 no longer contacts stripper pin 207, thereby breaking the air-tight seal. With purge valve 129 open, ambient air in housing 11 immediately rushes through purge port 256 between annular seal 265 and stripper pin 231 and through the gap 261 between cutter 127 and stripper pin 231. Air further rushes into vacuum chamber 121 to immediately purge vacuum therein and provide pressure equalization, as indicated by the air flow directional arrows (FIGS. 34, 34A, 34B).

Also as indicated by the air flow directional arrows in FIGS. 34-34A, air rushes through air-flow ports 225 on the distal side of annular seal 137 to purge the vacuum within cannula 13 lumen 41 in the gap 159 between cannula 13 and cutter 127 and the gap 283 between cutter 127 and stripper pin 231, and at tissue-receiving aperture 53 at the junction of cannula 13 and cutter 127 outer surface 153. This pressure equalization automatically releases any forces holding tissue 47 against cannula 13 at the region proximate tissue-receiving aperture 53. This release of forces enables a biopsy device 10, 10' to be easily removed from the patient's body with no tearing of tissue 47 surrounding cannula 13 so that patient discomfort is minimized and so that sample 59 can be ejected from cannula lumen 41 and out through tissue-receiving aperture 53 during subsequent operation.

Biopsy device 10, 10' is then withdrawn from the tissue 47. Tissue sample 59 can now be ejected from biopsy device 10, 10'.

FIGS. 37-40 illustrate biopsy devices 10, 10' during tissue sample 59 ejection and FIGS. 60H-60L illustrate a tissue sample 59 during ejection. While holding cannula support 29 with one hand, the user pulls the charging handles 301, 303 proximally toward housing rear end 23 with fingers of the user's other hand while simultaneously pressing against the push surface 219, preferably with the user's thumb. Provision of a spring 315 with a lower spring rate than spring 125 enables cutter 127 to open tissue-receiving aperture 53 before vacuum generating mechanism 17 generates the air pulse at tissue-receiving cavity 42.

If a delay mechanism (FIGS. 40-41) is provided, stops 351, 353 and stop surfaces 355, 357 would momentarily delay retracting movement of cutter carrier 251 in the direction of arrow 199, preferentially permitting advancement of handle 201 in the direction of arrow 221. As a result of such exemplary sequential operation of cutter carrier 251 and piston carrier 161, cutter 127 remains partially across tissue-receiving aperture 53 as tissue sample 59 ejection begins as illustrated schematically in FIGS. 60H-60J during the retraction stroke. This facilitates generation of the positive air pressure which ejects tissue sample 59 as described below.

Advancement of piston carrier 161 and piston 123 in the direction of arrow 221 by user pushing of handle 201 push surface 219 causes vacuum generating mechanism 17 to generate a positive air pressure at tissue-receiving aperture 53 and tissue-receiving cavity 42. Vacuum generating mechanism 17 generates the positive pressure as piston 123 advances toward housing front 21 in the direction of arrow 221 to provide positive air pressure through air-flow ports 225 which are now within vacuum chamber 121 as a result of cutter 127 retraction rearward in the direction of arrow 199 toward housing rear side 23 during the retraction stroke. Positive pressure forces air through air-flow ports 225 and into cutter carrier lumen 261 in the gap 283 between cutter inner surface 259 and stripper pin 231 and into tissue-receiving aperture 53 and tissue-receiving cavity 42 as indicated schematically in FIGS. 60J-60L and by the air flow directional arrows in FIGS. 39-39B.

Preferably, this positive air pressure is delivered from vacuum generating mechanism 17 while tissue-receiving aperture 53 remains partially obstructed by cutter distal end 253 and cutter 127 outer surface 153 assisted by operation of the delay mechanism as illustrated schematically in FIGS. 60J-60L. If tissue-receiving aperture 53 remains partially obstructed by cutter distal end 253 and cutter 127 outer surface 153, then tissue sample 59 is preferentially ejected commencing with a proximal end of tissue sample 59. Positive air pressure pushes tissue sample 59 distally within tissue-receiving cavity 42 and out of cutter 127 lumen 261 and cannula 13 through tissue-receiving aperture 53 for histological assessment or other use, completing the exemplary biopsy procedure.

The biopsy process may be repeated from the same site. Depth guide 401 facilitates tissue sample 59 acquisition from the same site by providing a consistent platform for insertion of cannula 13. With cannula 13 at a repeatable depth, utilization of cannula support 29 to rotate cannula 13 and tissue-receiving aperture 53 to an indexed position (FIGS. 44A-44D) enables repeatable tissue 47, 48 acquisition from selected positions about the cannula 13.

Persons of skill in the art will appreciate that biopsy devices 10, 10' will have structure and methods of use other than as described above. By way of example only, biopsy devices 10, 10' and variations thereof may be used in types of surgical procedures other than those described herein, including in conjunction with automated surgical procedures. Also by way of example, various components and subassemblies may have application in biopsy devices other than as shown and described herein. For example, components and subassemblies may have application in automated biopsy devices which may include devices having components external to the biopsy device.

Embodiments of the present invention may be designed for disposal after a single use or may be designed for reuse following cleaning and sterilization. By way of example only, single use embodiments may include components made of relatively less expensive plastic materials thereby providing an opportunity to reduce cost consistent with a disposable device. By way of further example, reusable embodiments may include components capable of repeated cleaning, sterilization, repair and replacement consistent with a more durable device suitable for use in multiple procedures.

While the principles of this invention have been described in connection with specific embodiments, it should be understood clearly that these descriptions are made only by way of example and are not intended to limit the scope of the invention.

What is claimed is:

1. A biopsy device comprising:
   a housing;
   an outer cannula defining an axis and including a tissue-receiving cavity, the outer cannula extending to a tip distal from the housing and being in a fixed axial relationship with respect to the housing;
   a cutter cannula at least partially within the outer cannula, the cutter cannula being movable along the axis relative to the outer cannula and the tissue-receiving cavity;
   a vacuum generating mechanism in air-flow communication with the cutter cannula, the outer cannula and the tissue-receiving cavity, the vacuum generating mechanism including a vacuum chamber concentric with the cutter cannula, and a piston in the chamber in air-sealing relationship with the chamber and around at least a portion of the cutter cannula such that the piston and cutter cannula are enabled to move independent of the other while maintaining the seal;

a first biasing device which moves the piston over the cutter cannula axially away from the tissue-receiving cavity to produce a vacuum in the tissue-receiving cavity; and a second biasing device which advances the cutter cannula through the piston and across the tissue-receiving cavity, whereby the first biasing device operates the vacuum generating mechanism to draw tissue into the tissue-receiving cavity before the second biasing device advances the cutter cannula to cut the tissue.

2. The biopsy device of claim 1 wherein the piston is concentric with the vacuum chamber.

3. The biopsy device of claim 1 wherein the first and second biasing devices are coaxial with the cutter cannula.

4. The biopsy device of claim 1 wherein the cutter cannula includes at least one air-flow port therethrough within the vacuum chamber and the at least one air-flow port and vacuum are between the piston and the tissue-receiving cavity during the entirety of production of the vacuum, the at least one air-flow port being in air-flow communication with the outer cannula and tissue-receiving cavity for drawing air therefrom into the vacuum chamber to produce the vacuum in the tissue-receiving cavity.

5. The biopsy device of claim 4 further comprising a purge valve which automatically purges the vacuum once the cutter cannula advances across the tissue-receiving cavity.

6. The biopsy device of claim 5 wherein the purge valve includes a seal concentric with the cutter cannula, the purge valve operating between a closed position during the vacuum production in which the seal prevents vacuum purging and an open position in which the seal allows ambient air flow through the cutter cannula to purge the vacuum in the tissue-receiving cavity after the cutter cannula begins movement across the tissue-receiving cavity.

7. The biopsy device of claim 6 wherein the seal moves with the cutter cannula along the axis.

8. The biopsy device of claim 7 wherein:

the purge valve further includes an elongate member which is in a fixed position within and concentric with the cutter cannula and has a notch therein; and when in the closed position, the seal is in air-sealing relationship around the elongate member and an open proximal end of the cutter cannula and, when in the open position, the seal is aligned with the notch allowing the ambient air flow between the elongate member and seal and into the open end of the cutter cannula.

9. The biopsy device of claim 8 wherein, when in the open position, the at least one air-flow port of the cutter cannula allows ambient air flow into the outer cannula to purge the vacuum about the outer cannula at the tissue-receiving cavity to facilitate withdrawal of the biopsy device with a tissue sample therein.

10. The biopsy device of claim 8 wherein the elongate member has a distal end stop surface proximate the tissue-receiving cavity which partially fills the cutter cannula to limit movement of a tissue sample into the cutter cannula.

11. The biopsy device of claim 3 wherein the first and second biasing devices are springs.

\* \* \* \* \*